US009180120B2

(12) United States Patent
Fürstner et al.

(10) Patent No.: US 9,180,120 B2
(45) Date of Patent: *Nov. 10, 2015

(54) SUBSTITUTED N-PHENETHYLTRIAZOLONEACETAMIDES AND USE THEREOF

(75) Inventors: Chantal Fürstner, Mülheim/Ruhr (DE); Joerg Keldenich, Wuppertal (DE); Martina Delbeck, Heiligenhaus (DE); Peter Kolkhof, Wuppertal (DE); Axel Kretschmer, Wuppertal (DE); Elisabeth Pook, Wuppertal (DE); Carsten Schmeck, Mülheim (DE); Hubert Trübel, Wuppertal (DE)

(73) Assignee: Bayer Intellectual Property GmbH, Mcnheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/818,337

(22) PCT Filed: Aug. 31, 2011

(86) PCT No.: PCT/EP2011/065000
§ 371 (c)(1),
(2), (4) Date: Apr. 5, 2013

(87) PCT Pub. No.: WO2012/028644
PCT Pub. Date: Mar. 8, 2012

(65) Prior Publication Data
US 2013/0225646 A1 Aug. 29, 2013

(30) Foreign Application Priority Data
Sep. 2, 2010 (DE) .......................... 10 2010 040 187

(51) Int. Cl.
A61K 31/41 (2006.01)
A61K 31/4196 (2006.01)
C07D 249/12 (2006.01)
C07D 409/04 (2006.01)
A61K 45/06 (2006.01)

(52) U.S. Cl.
CPC ............. A61K 31/4196 (2013.01); A61K 45/06 (2013.01); C07D 249/12 (2013.01); C07D 409/04 (2013.01)

(58) Field of Classification Search
CPC . A61K 31/4196; A61K 31/41; C07D 409/04; C07D 249/12
USPC ....................................................... 514/384
See application file for complete search history.

(56) References Cited

U.S. PATENT DOCUMENTS

| 5,276,049 | A | 1/1994 | Himmelsbach et al. |
| 5,281,614 | A | 1/1994 | Ashton et al. |
| 5,326,776 | A | 7/1994 | Winn et al. |
| 5,468,448 | A | 11/1995 | Nicolson et al. |
| 5,585,394 | A | 12/1996 | Di Malta et al. |
| 5,681,841 | A | 10/1997 | Himmelsbach et al. |
| 6,469,012 | B1 | 10/2002 | Ellis et al. |
| 6,531,142 | B1 | 3/2003 | Rabe et al. |
| 6,693,102 | B2 | 2/2004 | Stasch et al. |
| 6,743,798 | B1 | 6/2004 | Straub et al. |
| 6,746,989 | B1 | 6/2004 | Müller et al. |
| 6,762,152 | B1 | 7/2004 | Müller et al. |
| 6,833,364 | B1 | 12/2004 | Straub et al. |
| 6,838,415 | B1 | 1/2005 | Müller et al. |
| 6,864,287 | B1 | 3/2005 | Alonso-Alija et al. |
| 6,924,251 | B1 | 8/2005 | Schwarz et al. |
| 6,969,697 | B2 | 11/2005 | Muller et al. |
| 7,080,644 | B2 | 7/2006 | Gumaste |
| 7,173,037 | B2 | 2/2007 | Alonso-Alija et al. |
| 7,279,444 | B2 | 10/2007 | Muller et al. |
| 7,642,275 | B2 | 1/2010 | Bressi et al. |
| 7,674,825 | B2 | 3/2010 | Alonso-Alija et al. |
| 8,084,481 | B2 | 12/2011 | Meier et al. |
| 8,202,895 | B2 * | 6/2012 | Bruggemeier et al. ....... 514/376 |
| 2001/0020100 | A1 | 9/2001 | Manning et al. |
| 2002/0045651 | A1 | 4/2002 | Brenner et al. |
| 2002/0172644 | A1 | 11/2002 | Haslwanter et al. |
| 2003/0161790 | A1 | 8/2003 | Wahi et al. |
| 2004/0071757 | A1 | 4/2004 | Rolf |
| 2004/0082798 | A1 | 4/2004 | Alonso-Alija et al. |
| 2004/0176446 | A1 | 9/2004 | Alonso-Alija et al. |

(Continued)

FOREIGN PATENT DOCUMENTS

| EP | 0051829 | 5/1982 |
| EP | 0412594 | 7/1990 |

(Continued)

OTHER PUBLICATIONS

Bronson, et al.,:"Discovery of the First Antibactrial Small Molecule Inhibitors of MurB," Bioorganic & Medicinal Chemistry Letters, 2003, 13: 873-875.
DeLuca, et al.,:"Hyponatremia in Paitents with Heart Failure,"Am. J. Cardiol., 2005, vol. 96 (suppl.), 19L-23L.
Francis, et al.:"Comparison of Neuroendocrine Activation in Patients with Left Ventricular Dysfunction with and without Congestive Heart Failure," Circulation, Nov. 1990, 82(5): 1724-1729.
Lemmens-Gruber, et al.:"Vasopressin Antagonists," Cell. Mol. Life Sci., 2006, 63:1766-1779.
Palm, et al.:"Vasopressin Antagonists as Aquaretic Agents for the Treatment of Hyponatremia," Am. J. Med., 2006, 119(7A): S87-S92.
Saghi, et al.:"Vasopressin Antagonism: A Future Treatment Option in Heart Failure," Europ. Heart J., 2005, 26: 538-543.

(Continued)

Primary Examiner — Jeffrey S Lundgren
Assistant Examiner — Chris Simmons
(74) Attorney, Agent, or Firm — Karen B. King

(57) ABSTRACT

The present application relates to novel substituted N-phenethyltriazoloneacetamides, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

3 Claims, No Drawings

(56) References Cited

U.S. PATENT DOCUMENTS

| | | |
|---|---|---|
| 2006/0148779 A1 | 7/2006 | Bell et al. |
| 2007/0225333 A1 | 9/2007 | Bryans et al. |
| 2007/0281937 A1 | 12/2007 | Zelle et al. |
| 2008/0058314 A1 | 3/2008 | Kabra et al. |
| 2008/0139560 A1 | 6/2008 | Zelle et al. |
| 2009/0312381 A1* | 12/2009 | Meier et al. ............... 514/384 |
| 2010/0261771 A1 | 10/2010 | Bruggemeier et al. |
| 2011/0245308 A1 | 10/2011 | Bruggemeier et al. |
| 2012/0208852 A1 | 8/2012 | Furstner et al. |

FOREIGN PATENT DOCUMENTS

| | | |
|---|---|---|
| EP | 0533276 | 3/1993 |
| WO | 9931099 | 6/1999 |
| WO | 0100595 | 1/2001 |
| WO | 0119355 | 3/2001 |
| WO | 02066447 | 8/2002 |
| WO | 2006117657 | 11/2006 |
| WO | 2011104322 | 9/2011 |

OTHER PUBLICATIONS

Schrier, et al.:"Hormones and Hemodynamics in Heart Failure," New Engl. J. Med., Aug. 19, 1999, 341(8): 577-585.

Tang, et al.:"Vasopressin Receptor Antagonists in the Management of Acute Heart Failure," Expert Opin. Investig. Drugs, 2005, 14(5): 593-600.

Hassan et al., "Aryl-Aryl Bond Formation One Century after the Discovery of the Ulmann Reaction," Chem Rev 2002, 102:1359-1469.

Arnswald, et al., "Unconventional Regiospecific Synthesis of Aromatic Carbonamides and Thiocarbonamides by Means of Tin-Mediated Friedel-Crafts Reactions." J. Org. Chem., 1993 58(25): 7022-7028.

Papadopoulos et al.,"Friedel-Crafts Thioacylation with Ethoxycarbonyl Isothiocyanate: A One-Step Synthesis of Aromatic Thioamides," J. Org. Chem 1976, 41(6): 962-965.

U.S. Appl. No. 12/301,616, filed Jun. 15, 2009.

U.S. Appl. No. 13/132,897, filed Jun. 15, 2009.

U.S. Appl. No. 13/255,515, filed Aug. 9, 2011.

U.S. Appl. No. 13/819,885, filed Feb. 28, 2013.

U.S. Appl. No. 13/426,444, filed Mar. 21, 2012.

Chang et al., "Triazolinones as Nonpeptide Angiotensin II Antagonists. 1. Synthesis and Evaluation of Potent 2, 4, 5-Trisubstituted Triazoloinones," J. Med. Chem. 1993, 36(17):2558-2568.

Dobosz et al., "Synthesis and Some Pharmacological Properties of 3-(4-phenyl-5-oxo-1,2,4-triazolin-1-ylmethyl)-1,2,-triazolin-5-thione Derivatives," Acta Polomiae Pharmaceutica 2002, 59(4):281-290.

Finley, et al., "Arginine Vasopressin Antagonists for the Treatment of Heart Failure and Hyponatremia," Circulation 2008, 118:410-421.

Gines, P. et al., "Effects of stavaptan, a selective vasopressin V2 receptor antagonist, on ascites and serum sodium cirrhosis with hyponatremia," Hepatology, 2008, 48(1):204-212.

Goldsmith, et al., "Current treatments and novel pharmacologic treatments for hyponatremia in congestive heart failure," Am. J. Cardiol, 2005, 95(suppl):14B-23B.

Patani, et al., "Bioisosterism: A Rational Approach in Drug Design," Chem. Rev., 1996, 96:3147-3176.

Schrier, Robert W., "The sea within us: Disorders of body water homeostasis," Current Opinion in Investigational Drugs, 2007, 8(4):304-311.

Verbalis, J.G., "AVP receptor antagonists as aquaretics: Review and assessment of clinical data," Cleveland Clinic Journal of Medicine, Sep. 2009, 73:S24-S33.

\* cited by examiner

SUBSTITUTED N-PHENETHYLTRIAZOLONEACETAMIDES AND USE THEREOF

The present application relates to novel substituted N-phenethyltriazoloneacetamides, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

The liquid content of the human body is subject to various physiological control mechanisms whose purpose is to keep it constant (volume homeostasis). In the process, both the volume filling of the vascular system and also the osmolarity of the plasma are continuously recorded by appropriate sensors (baroreceptors and osmoreceptors). The information which these sensors supply to the relevant centres in the brain regulates drinking behaviour and controls fluid excretion via the kidneys by means of humoral and neural signals. The peptide hormone vasopressin is of central importance in this [Schrier R. W., Abraham, W. T., *New Engl. J. Med.* 341, 577-585 (1999)].

Vasopressin is produced in specialized endocrine neurons in the nucleus supraopticus and n. para-ventricularis in the wall of the third ventricle (hypothalamus) and transported from there along its neural processes into the posterior lobes of the hypophysis (neurohypophysis). There the hormone is released into the bloodstream according to stimulus. A loss of volume, e.g. as a result of acute bleeding, heavy sweating, prolonged thirst or diarrhoea, is a stimulus for intensified outpouring of the hormone. Conversely, the secretion of vasopressin is inhibited by an increase in the intravascular volume, e.g. as result of increased fluid intake.

Vasopressin exerts its action mainly via binding to three receptors, which are classified as V1a, V1b and V2 receptors and belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this clinical picture excrete up to 20 liters of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Logically, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that by means of V2 antagonist drugs, volume homeostasis can be restored, without in the process affecting electrolyte homeostasis. Hence drugs with V2 antagonist activity appear particularly suitable for the treatment of all disease conditions which are associated with an overloading of the body with water, without the electrolytes being effectively increased in parallel. A significant electrolyte abnormality is measurable in clinical chemistry as hyponatraemia (sodium concentration<135 mmol/L); it is the most important electrolyte abnormality in hospital patients, with an incidence of about 5% or 250 000 cases per year in the USA alone. If the plasma sodium concentration falls below 115 mmol/L, comatose states and death are imminent.

Depending on the underlying cause, a distinction is made between hypovolaemic, euvolaemic and hypervolaemic hyponatraemia. The forms of hypervolaemia with oedema formation are clinically significant. Typical examples of this are the syndrome of inappropriate ADH/vasopressin secretion (SIAD) (e.g. after craniocerebral trauma or as paraneoplasia in carcinomas) and hypervolaemic hyponatraemia in liver cirrhosis, various renal diseases and heart failure [De Luca L. et al., *Am. J. Cardiol.* 96 (suppl.), 19L-23L (2005)]. In particular, patients with heart failure, in spite of their relative hyponatraemia and hypervolaemia, often display elevated vasopressin levels, which is seen as the consequence of generally disturbed neurohumoral regulation in heart failure [Francis G. S. et al., *Circulation* 82, 1724-1729 (1990)].

The disturbed neurohumoral regulation essentially manifests itself in an elevation of the sympathetic tone and inappropriate activation of the renin-angiotensin-aldosterone system. While the inhibition of these components by beta-receptor blockers on the one hand and by ACE inhibitors or angiotensin-receptor blockers on the other is now an inherent part of the pharmacological treatment of heart failure, the inappropriate elevation of vasopressin secretion in advanced heart failure is at present still not adequately treatable. Apart from the retention of water mediated by V2 receptors and the unfavourable haemodynamic consequences associated therewith in terms of increased backload, the emptying of the left ventricle, the pressure in the pulmonary blood vessels and cardiac output are also adversely affected by V1a-mediated vasoconstriction. Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, substances which inhibit the action of vasopressin on the V2 and/or on the V1a receptor appear suitable for the treatment of heart failure. In particular, compounds with combined activity on both vasopressin receptors (V1a and V2) should both have desirable renal and also haemodynamic effects and thus offer an especially ideal profile for the treatment of patients with heart failure. The provision of such combined vasopressin antagonists also appears to make sense inasmuch as a volume diminution mediated solely via V2 receptor blockade can entail the stimulation of osmoreceptors and as a result a further compensatory increase in vasopressin release. As a result, in the absence of a component simultaneously blocking the V1a receptor, the harmful effects of the vasopressin, such as for example vasoconstriction and heart muscle hypertrophy, could be further intensified [Saghi P. et al., *Europ. Heart J.* 26, 538-543 (2005)].

It was therefore an object of the present invention to provide novel compounds which act as potent selective V1a, V2 or dual V1a/V2 receptor antagonists and as such are suitable for the treatment and/or prevention of diseases, more particularly for the treatment and/or prevention of cardiovascular disorders.

WO 99/31099-A1 discloses variously substituted 1,2,4-triazolones as therapeutically useful integrin receptor antagonists. The use of 5-aryl-1,2,4-triazolones as medicaments having neuroprotective action was claimed in WO 99/54315-A2, and WO 2006/117657-A1 describes 4,5-diaryltriazolone derivatives as anti-inflammatory agents. WO 2005/105779-A1 discloses 3-heterocyclyl-4-phenyltriazoles as inhibitors of the vasopressin V1A receptor, and WO 2007/134862-A1 discloses amidically linked 5-aryl-1,2,4-triazolones as dual vasopressin antagonists.

The present invention provides compounds of the general formula (I)

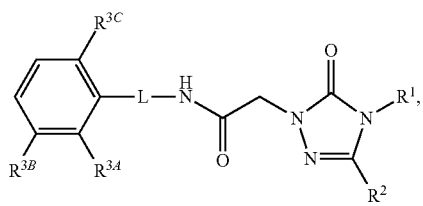

in which
$R^1$ represents $(C_1-C_6)$-alkyl, $(C_2-C_6)$-alkenyl or $(C_2-C_6)$-alkynyl, each of which may be mono- or disubstituted by identical or different radicals selected from the group consisting of fluorine, chlorine, cyano, difluoromethyl, trifluoromethyl, oxo, hydroxy, difluoromethoxy, trifluoromethoxy, $(C_1-C_4)$-alkoxy, $(C_3-C_6)$-cycloalkyl and phenyl,
  where $(C_3-C_6)$-cycloalkyl may be substituted up to two times by identical or different radicals selected from the group consisting of fluorine, trifluoromethyl, $(C_1-C_4)$-alkyl, oxo, hydroxy, trifluoromethoxy and $(C_1-C_4)$-alkoxy and
  where phenyl may be substituted up to three times by identical or different radicals selected from the group consisting of halogen, cyano, difluoromethyl, trifluoromethyl, $(C_1-C_4)$-alkyl, hydroxy, hydroxymethyl, difluoromethoxy, trifluoromethoxy, $(C_1-C_4)$-alkoxy, $(C_1-C_4)$-alkoxymethyl, hydroxycarbonyl, $(C_1-C_4)$-alkoxycarbonyl, amino-carbonyl, mono-$(C_1-C_4)$-alkylaminocarbonyl and di-$(C_1-C_4)$-alkylaminocarbonyl, or
  represents $(C_3-C_6)$-cycloalkyl which may be mono- or disubstituted by identical or different radicals selected from the group consisting of fluorine, trifluoromethyl, $(C_1-C_4)$-alkyl, oxo, hydroxy, trifluoromethoxy and $(C_1-C_4)$-alkoxy,
$R^2$ represents phenyl or thienyl which may be mono- or disubstituted by identical or different radicals selected from the group consisting of halogen, cyano, difluoromethyl, trifluoromethyl, $(C_1-C_4)$-alkyl, hydroxy, trifluoromethoxy and $(C_1-C_4)$-alkoxy,
$R^{3A}$, $R^{3B}$ and $R^{3C}$ independently of one another represent hydrogen, fluorine, chlorine, difluoromethyl, trifluoromethyl, $(C_1-C_4)$-alkyl, difluoromethoxy, trifluoromethoxy or $(C_1-C_4)$-alkoxy,
  but where at least one of the radicals $R^{3A}$, $R^{3B}$, $R^{3C}$ is different from hydrogen, and L represents a group of the formula

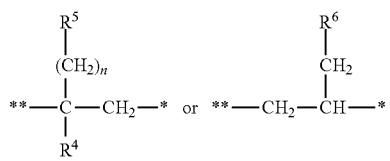

in which
* represents the point of attachment to the adjacent nitrogen atom and
** represents the point of attachment to the phenyl ring,
n represents the number 0, 1 or 2,
$R^4$ represents hydrogen or methyl,
$R^5$ represents a group of the formula —O—C(=O)—NR$^{7A}$R$^{7B}$, —NR$^8$—C(=O)—NR$^{7A}$R$^{7B}$, —NR$^8$—SO$_2$—NR$^{7A}$R$^{7B}$, —NR$^8$—C(=O)—R$^9$, —NR$^8$—SO$_2$—R$^{10}$ or —NR$^8$—C(=O)—OR$^{10}$ in which
  $R^{7A}$ and $R^{7B}$ independently of one another represent hydrogen, $(C_1-C_6)$-alkyl or $(C_3-C_6)$-cycloalkyl or together with the nitrogen atom to which both are attached form a 4- to 6-membered heterocycle which may contain a further ring heteroatom from the group consisting of N, O and S and which may be mono- or disubstituted by identical or different radicals selected from the group consisting of fluorine, trifluoromethyl, $(C_1-C_4)$-alkyl, hydroxy and oxo,
  $R^8$ represents hydrogen or $(C_1-C_4)$-alkyl,
  $R^9$ represents hydrogen, $(C_1-C_6)$-alkyl or $(C_3-C_6)$-cycloalkyl, and
  $R^{10}$ represents $(C_1-C_6)$-alkyl or $(C_3-C_6)$-cycloalkyl, and
$R^6$ has the meaning of $R^5$ given above or represents hydroxy,
and their salts, solvates and solvates of the salts.

Compounds according to the invention are the compounds of the formula (I) and their salts, solvates, and solvates of the salts; the compounds of the below-specified formulae embraced by formula (I), and their salts, solvates, and solvates of the salts; and also the compounds specified below as working examples and embraced by formula (I), and their salts, solvates, and solvates of the salts; in so far as the below-specified compounds embraced by formula (I) are not already salts, solvates, and solvates of the salts.

Preferred salts in the context of the present invention are physiologically acceptable salts of the compounds according to the invention. Salts which are not themselves suitable for pharmaceutical uses but can be used, for example, for isolation, purification or storage of the compounds according to the invention are also included.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalene-disulphonic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, N,N-diisopropylethylamine, monoethanol-amine, diethanolamine, triethanolamine, dimethylaminoethanol, diethylaminoethanol, procaine, dicyclohexylamine, dibenzylamine, N-methylpiperidine, N-methylmorpholine, arginine, lysine and 1,2-ethylenediamine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The compounds according to the invention can exist in different stereoisomeric forms depending on their structure, i.e. in the form of configuration isomers or optionally also as conformation isomers (enantiomers and/or diastereomers, including those in the case of atropisomers). The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention includes all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally used processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

In the context of the present invention, the substituents have the following meaning, unless specified otherwise:

In the context of the invention, ($C_1$-$C_6$)-alkyl and ($C_1$-$C_4$)-alkyl represent a straight-chain or branched alkyl radical having 1 to 6 and 1 to 4 carbon atoms, respectively. Preference is given to a straight-chain or branched alkyl radical having 1 to 4 carbon atoms. The following may be mentioned by way of example and by way of preference: methyl, ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

In the context of the invention, ($C_2$-$C_6$)-alkenyl and ($C_2$-$C_4$)-alkenyl represent a straight-chain or branched alkenyl radical having 2 to 6 and 2 to 4 carbon atoms, respectively, and a double bond. Preference is given to a straight-chain alkenyl radical having 2 to 4 carbon atoms. The following may be mentioned by way of example and by way of preference: vinyl, n-prop-1-en-1-yl, allyl, iso-propenyl, 2-methyl-2-propen-1-yl, n-but-1-en-1-yl, n-but-2-en-1-yl, n-but-3-en-1-yl, n-pent-1-en-1-yl, n-pent-2-en-1-yl, n-pent-3-en-1-yl, n-pent-4-en-1-yl, 3-methylbut-2-en-1-yl and 4-methylpent-3-en-1-yl.

In the context of the invention, ($C_2$-$C_6$)-alkynyl represents a straight-chain or branched alkynyl radical having 2 to 6 carbon atoms and a triple bond. Preference is given to a straight-chain or branched alkynyl radical having 3 to 6 carbon atoms. The following may be mentioned by way of example and by way of preference: ethynyl, n-prop-1-yn-1-yl, n-prop-2-yn-1-yl, n-but-2-yn-1-yl, n-but-3-yn-1-yl, n-pent-2-yn-1-yl, n-pent-3-yn-1-yl and n-pent-4-yn-1-yl.

In the context of the invention, ($C_1$-$C_4$)-alkoxy represents a straight-chain or branched alkoxy radical having 1 to 4 carbon atoms. The following may be mentioned by way of example and by way of preference: methoxy, ethoxy, n-propoxy, isopropoxy, n-butoxy, isobutoxy, sec-butoxy and tert-butoxy.

In the context of the invention, ($C_1$-$C_4$)-alkoxymethyl represents a straight-chain or branched alkoxy radical having 1 to 4 carbon atoms which is attached to the remainder of the molecule via a methylene group [—$CH_2$—] attached to the oxygen atom. The following may be mentioned by way of example and by way of preference: methoxymethyl, ethoxymethyl, n-propoxymethyl, iso-propoxymethyl, n-butoxymethyl and tert-butoxymethyl.

In the context of the invention, ($C_1$-$C_4$)-alkoxycarbonyl represents a straight-chain or branched alkoxy radical having 1 to 4 carbon atoms which is attached to the remainder of the molecule via a carbonyl group [—C(=O)—] attached to the oxygen atom. The following may be mentioned by way of example and by way of preference: methoxycarbonyl, ethoxycarbonyl, n-propoxycarbonyl, iso-propoxycarbonyl, n-butoxycarbonyl and tert-butoxycarbonyl.

In the context of the invention, mono-($C_1$-$C_4$)-alkylamino represents an amino group having a straight-chain or branched alkyl substituent having 1 to 4 carbon atoms. The following may be mentioned by way of example and by way of preference: methylamino, ethylamino, n-propylamino, isopropylamino, n-butylamino and tert-butylamino.

In the context of the invention, di-($C_1$-$C_4$)-alkylamino represents an amino group having two identical or different straight-chain or branched alkyl substituents each having 1 to 4 carbon atoms. The following may be mentioned by way of example and by way of preference: N,N-dimethylamino, N,N-diethylamino, N-ethyl-N-methylamino, N-methyl-N-n-propylamino, N-isopropyl-N-methylamino, N-isopropyl-N- n-propylamino, N,N-diisopropylamino, N-n-butyl-N-methylamino, N,N-di-n-butylamino and N-tert-butyl-N-methylamino.

In the context of the invention, mono- and di-$(C_1-C_4)$-alkylaminocarbonyl represent amino groups which are attached to the remainder of the molecule via a carbonyl group [—C(=O)—] and which have, respectively, one straight-chain or branched and two identical or different straight-chain or branched N-alkyl substituents each having 1 to 4 carbon atoms. The following may be mentioned by way of example and by way of preference: methylaminocarbonyl, ethylaminocarbonyl, n-propylaminocarbonyl, isopropylaminocarbonyl, n-butylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N,N-diisopropylaminocarbonyl, N-n-butyl-N-methylamino-carbonyl and N-tert-butyl-N-methylaminocarbonyl.

In the context of the invention, $(C_3-C_6)$-cycloalkyl and $(C_3-C_5)$-cycloalkyl represent monocyclic, saturated cycloalkyl groups having 3 to 6 and 3 to 5 carbon atoms, respectively. The following may be mentioned by way of example and by way of preference: cyclopropyl, cyclobutyl, cyclopentyl and cyclohexyl.

In the context of the invention, a 4- to 6-membered heterocycle represents a monocyclic, saturated heterocycle having a total of 4 to 6 ring atoms which contains a ring nitrogen atom linking it to the remainder of the molecule and which may additionally contain a further ring heteroatom from the group consisting of N, O and S. The following may be mentioned by way of example and by way of preference: azetidinyl, pyrrolidinyl, pyrazolidinyl, 1,3-oxazolidinyl, 1,3-thiazolidinyl, piperidinyl, piperazinyl, morpholinyl and thiomorpholinyl. Preference is given to azetidinyl, pyrrolidinyl, piperidinyl and morpholinyl.

In the context of the invention, halogen includes fluorine, chlorine, bromine and iodine. Preference is given to chlorine, fluorine or bromine, particularly preferably fluorine or chlorine.

In the context of the invention, an oxo substituent represents an oxygen atom which is attached to a carbon atom via a double bond.

In the context of the present invention, all radicals which occur more than once are defined independently of one another. If radicals in the compounds according to the invention are substituted, the radicals may be mono- or polysubstituted, unless specified otherwise. Substitution by one, two or three identical or different substituents is preferred. Particular preference is given to substitution by one or two identical or different substituents. Very particular preference is given to substitution by one substituent.

A preferred embodiment of the present invention embraces compounds of the formula (I) in which
$R^1$ represents $(C_1-C_4)$-alkyl or $(C_2-C_4)$-alkenyl, each of which may be mono- or disubstituted by identical or different radicals selected from the group consisting of fluorine, tri-fluoromethyl, hydroxy, trifluoromethoxy and $(C_1-C_4)$-alkoxy, or
represents benzyl which may be mono- or disubstituted in the phenyl ring by identical or different radicals selected from the group consisting of fluorine, chlorine, trifluoromethyl, $(C_1-C_4)$-alkyl, trifluoromethoxy and $(C_1-C_4)$-alkoxy, or
represents $(C_3-C_5)$-cycloalkyl,
and their salts, solvates and solvates of the salts.

An equally preferred embodiment of the present invention embraces compounds of the formula (I) in which $R^2$ represents phenyl or thienyl which are substituted by a radical selected from the group consisting of fluorine, chlorine, cyano, methyl, difluoromethyl, trifluoromethyl, methoxy and trifluoromethoxy,
and their salts, solvates and solvates of the salts.

A further preferred embodiment of the present invention embraces compounds of the formula (I) in which
$R^{3A}$, $R^{3B}$ and $R^{3C}$ independently of one another represent hydrogen, fluorine, chlorine, methyl, difluoromethyl, trifluoromethyl, methoxy or trifluoromethoxy,
but where at least one of the radicals $R^{3A}$, $R^{3B}$, $R^3$ is different from hydrogen,
and their salts, solvates and solvates of the salts.

A further preferred embodiment of the present invention embraces compounds of the formula (I) in which
$R^{3C}$ represents hydrogen,
and their salts, solvates and solvates of the salts.

A further preferred embodiment of the present invention embraces compounds of the formula (I) in which
L represents a group of the formula

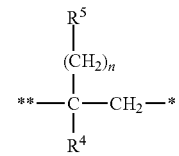

in which
* represents the point of attachment to the adjacent nitrogen atom and
** represents the point of attachment to the phenyl ring,
n represents the number 0 or 1,
$R^4$ represents hydrogen or methyl, and
$R^5$ represents a group of the formula —O—C(=O)—$NR^{7A}R^{7B}$, —NH—C(=O)—$NR^{7A}R^{7B}$, —NH—C(=O)—$R^9$, —NH—$SO_2$—$R^{10}$ or —NH—C(=O)—$OR^{10}$ in which
$R^{7A}$ and $R^{7B}$ independently of one another represent hydrogen or $(C_1-C_4)$-alkyl,
$R^9$ represents hydrogen or $(C_1-C_4)$-alkyl, and
$R^{10}$ represents $(C_1-C_4)$-alkyl,
and their salts, solvates and solvates of the salts.

A further preferred embodiment of the present invention embraces compounds of the formula (I) in which
L represents a group of the formula

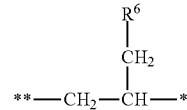

in which
* represents the point of attachment to the adjacent nitrogen atom and
** represents the point of attachment to the phenyl ring, and
$R^6$ represents hydroxy or a group of the formula —O—C(=O)—$NR^{7A}R^{7B}$ in which
$R^{7A}$ and $R^{7B}$ independently of one another represent hydrogen or $(C_1-C_4)$-alkyl, and their salts, solvates and solvates of the salts.

Particular preference in the context of the present invention is given to compounds of the formula (I) in which $R^1$ represents $(C_1\text{-}C_4)$-alkyl or $(C_2\text{-}C_4)$-alkenyl, each of which may be mono- or disubstituted by identical or different radicals selected from the group consisting of fluorine, tri-fluoromethyl, hydroxy, methoxy and ethoxy, or
represents benzyl which may be substituted in the phenyl ring by a radical selected from the group consisting of fluorine, chlorine, methyl, trifluoromethyl and methoxy, or
represents cyclopropyl,
$R^2$ represents phenyl or thienyl which are substituted by a radical selected from the group consisting of fluorine and chlorine,
$R^{3A}$ and $R^{3B}$ independently of one another represent hydrogen, fluorine, chlorine, methyl, tri-fluoromethyl, methoxy or trifluoromethoxy,
but where at least one of the radicals $R^{3A}$ and $R^{3B}$ is different from hydrogen,
$R^{3C}$ represents hydrogen, and
L represents a group of the formula

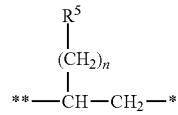

in which
* represents the point of attachment to the adjacent nitrogen atom and
** represents the point of attachment to the phenyl ring,
n represents the number 0 or 1, and
$R^5$ represents a group of the formula —O—C(=O)—NHR$^{7B}$, —NH—C(=O)—NHR$^{7B}$, —NH—C(=O)—R$^9$, —NH—SO$_2$—R$^{10}$ or —NH—C(=O)—OR$^{10}$ in which
$R^{7B}$ represents hydrogen or $(C_1\text{-}C_4)$-alkyl,
$R^9$ represents hydrogen or $(C_1\text{-}C_4)$-alkyl, and
$R^{10}$ represents $(C_1\text{-}C_4)$-alkyl,
and their salts, solvates and solvates of the salts.

Very particular preference in the context of the present invention is given to compounds of the formula (I) in which
$R^1$ represents 3,3,3-trifluoro-2-hydroxypropyl, 3,3,3-trifluoropropyl or 3,3,3-trifluoroprop-1-en-1-yl,
$R^2$ represents p-chlorophenyl,
$R^{3A}$ and $R^{3B}$ independently of one another represent hydrogen, chlorine or trifluoromethyl,
but where at least one of the radicals $R^{3A}$ and $R^{3B}$ is different from hydrogen,
$R^{3C}$ represents hydrogen, and
L represents a group of the formula

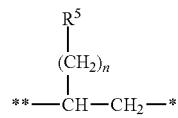

in which
* represents the point of attachment to the adjacent nitrogen atom and
** represents the point of attachment to the phenyl ring,
n represents the number 0 or 1, and
$R^5$ represents a group of the formula —O—C(=O)—NH$_2$, —NH—C(=O)—NH$_2$ or —NH—SO$_2$—R$^{10}$ in which
$R^{10}$ represents methyl or ethyl,
and their salts, solvates and solvates of the salts.

The definitions of radicals indicated specifically in the respective combinations or preferred combinations of radicals are replaced as desired irrespective of the particular combinations indicated for the radicals also by definitions of radicals of other combinations. Combinations of two or more of the abovementioned preferred ranges are particularly preferred.

The invention furthermore provides a process for preparing the compounds of the formula (I) according to the invention, characterized in that a compound of the formula (II)

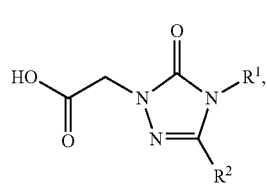

in which $R^1$ and $R^2$ have the meanings given above,
is coupled in an inert solvent with activation of the carboxylic acid function with a compound of the formula (III)

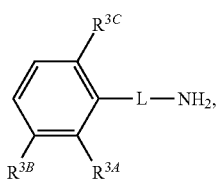

in which L, $R^{3A}$, $R^{3B}$ and $R^{3C}$ have the meanings given above, and the resulting compounds of the formula (I) are optionally separated into their enantiomers and/or diastereomers and/or converted with the appropriate (i) solvents and/or (ii) acids or bases into their solvates, salts and/or solvates of the salts.

Inert solvents for the process step (II)+(III)→(I) are, for example, ethers such as diethyl ether, diisopropyl ether, tert-butyl methyl ether, tetrahydrofuran, 1,4-dioxane, 1,2-dimethoxyethane or bis(2-methoxyethyl)ether, hydrocarbons such as benzene, toluene, xylene, pentane, hexane, heptane, cyclohexane or mineral oil fractions, halogenated hydrocarbons such as dichloromethane, trichloromethane, carbon tetrachloride, 1,2-dichloroethane, trichloroethylene or chlorobenzene, or dipolar aprotic solvents such as acetone, methyl ethyl ketone, ethyl acetate, acetonitrile, pyridine, dimethyl sulphoxide (DMSO), N,N-dimethylformamide (DMF), N,N-dimethylacetamide (DMA), N,N'-dimethylpropyleneurea (DMPU) or N-methylpyrrolidinone (NMP). It is also possible to use mixtures of such solvents. Preference is given to acetonitrile, dichloromethane, dimethylformamide or mixtures of these solvents.

Suitable activating/condensing agents for the coupling reaction (II)+(III)→(I) are, for example, carbodiimides such as N,N'-diethyl-, N,N'-dipropyl-, N,N'-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl-5-methyl-isoxazolium perchlorate, acylamino compounds such as 2-ethoxy-1-ethoxycarbonyl-1,2-dihydro-quinoline, α-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl)-phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate, or tertiary amine bases such as triethylamine, N-methylmorpholine, N-methylpiperidine, N,N-diisopropylethylamine, pyridine or 4-N,N-dimethylaminopyridine. Preference is given to using EDC in combination with HOBt and N,N-diisopropylethylamine.

The coupling (II)+(III)→(I) is generally carried out in a temperature range of from −20° C. to +60° C., preferably at from 0° C. to +40° C. The reaction can be carried out at atmospheric, at elevated or at reduced pressure (for example from 0.5 to 5 bar). In general, the reaction is carried out at atmospheric pressure.

The preparation of the compounds according to the invention can be illustrated by the synthesis scheme below:

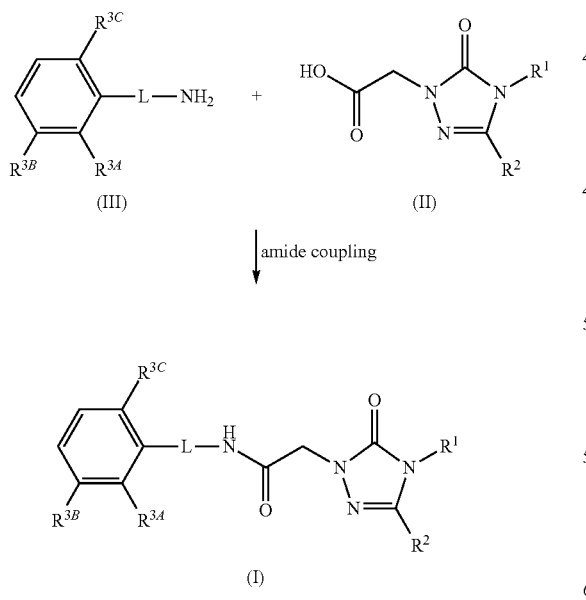

For their part, the compounds of the formula (II) can be obtained by base-induced alkylation of 2,4-dihydro-3H-1,2,4-triazol-3-ones of the formula (IV) with a haloacetic ester of the formula (V) to give the $N^2$-substituted compounds of the formula (VI) and subsequent ester hydrolysis (see Scheme 2):

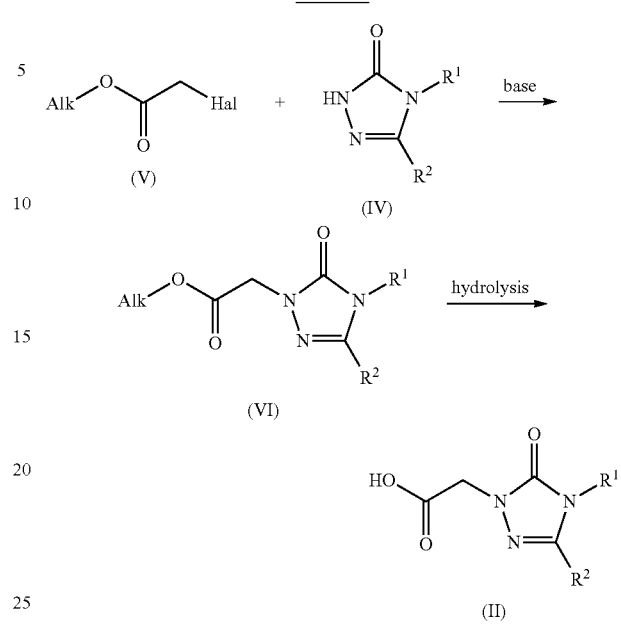

[Alk = alkyl, Hal = halogen].

By an alternative route, the compounds of the formula (VI) can also be prepared from N-(alkoxy-carbonyl)arylthioamides of the formula (VIII) known from the literature [see, for example, M. Arnswald, W. P. Neumann, *J. Org. Chem.* 58 (25), 7022-7028 (1993); E. P. Papadopoulos, *J. Org. Chem.* 41 (6), 962-965 (1976)] by reaction with a hydrazinoacetic ester of the formula (VII) and subsequent derivatization at N-4 of the triazolone (IX) (see Scheme 3):

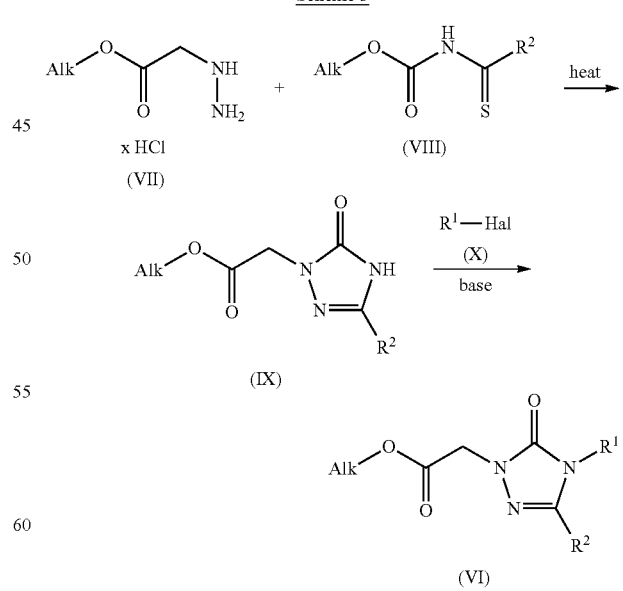

The compounds of the formula (IV) can be prepared starting with carboxylic acid hydrazides of the formula (XI) by reaction with isocyanates of the formula (XII) or nitrophenyl carbamates of the formula (XIII) and subsequent base-induced cyclization of the hydrazinecarboxamide intermediates (XIV) (see Scheme 4):

Scheme 4

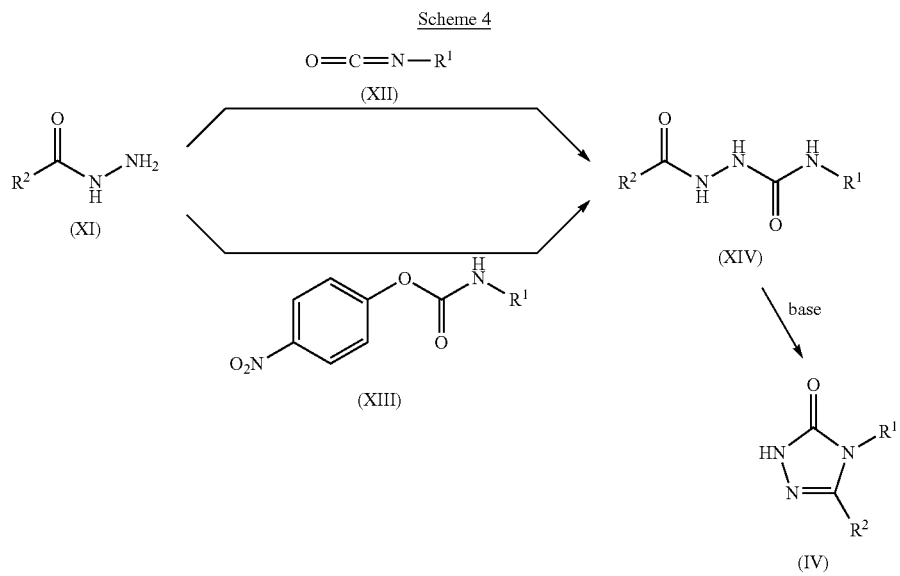

Here, introduction and removal of the protective group PG is carried out using methods customary in the literature [see, for example, T. W. Greene and P. G. M. Wuts, *Protective Groups in Organic Synthesis*, Wiley, New York, 1999]. Thus, the allyl group is preferably removed with the aid of formic acid in the presence of the tetrakis(triphenylphosphine)palladium(0) catalyst and an amine base such as triethylamine. The removal of the p-methoxybenzyl protective group is preferably carried out with the aid of strong acids such as trifluoroacetic acid, or oxidatively, for example by treatment with 2,3-dichloro-5,6-dicyano-1,4-benzoquinone (DDQ) or ammonium cerium(IV) nitrate.

Analogous transformations PG→$R^1$ can optionally also be carried out at other stages of the process.

According to a particular process variant, compounds of the formula (VI) can, if appropriate, also be prepared by employing, in the processes described in Schemes 2 and 4, instead of the radical $R^1$ initially a temporary protective group (PG), for example allyl or 4-methoxybenzyl; after its removal, giving compounds of the formula (IX), the desired compounds of the formula (VI) can then be obtained by appropriate $N^4$-alkylation (see Scheme 5):

Scheme 5

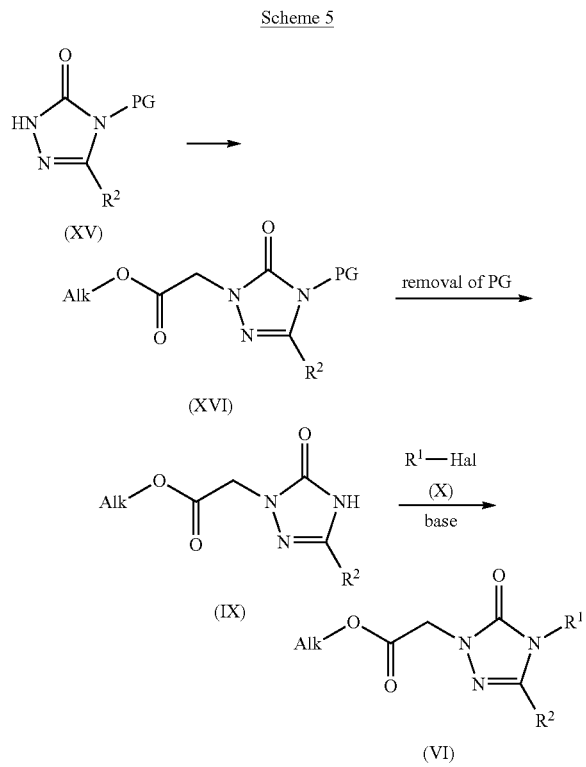

[PG = protective group, for example allyl or 4-methoxybenzyl].

Further compounds of the formula (I) according to the invention can, if appropriate, also be prepared by converting functional groups of individual substituents, in particular those listed under $R^1$, $R^2$, $R^5$ and $R^6$, starting with other compounds of the formula (I) obtained by the above processes or precursors thereof. These conversions are carried out by customary methods known to the person skilled in the art and include, for example, reactions such as nucleophilic and electrophilic substitution reactions, nucleophilic or electrophilic addition reactions, elimination reactions, oxidation, reduction, hydrogenation, alkylation, acylation, sulphonylation, amination, hydroxylation, etherification, esterification, ether cleavage and hydrolysis, in particular the formation of carboxamides, sulphonamides, carbamates, ureas and sulphuric acid diamides, and also the introduction and removal of temporary protective groups [cf. also the preparation of the Working Examples described in detail in the Experimental Part below].

Separation of the compounds according to the invention into the corresponding enantiomers and/or diastereomers can take place, depending on expediency, even at the stage of individual intermediates, as listed above, which are then reacted further in separated form in accordance with the above-described process steps. Such a separation of the stereoisomers can be carried out by conventional methods known to the person skilled in the art. Preference is given to using chromatographic methods, in particular HPLC chromatography on an achiral or chiral phase.

The compounds of the formulae (III), (V), (VII), (VIII), (X), (XI), (XII) and (XIII) are either commercially available or described as such in the literature, or they can be prepared, starting from commercially available compounds, by generally customary methods known from the literature. Numerous detailed procedures and literature references for preparing these substances can also be found in the Experimental Part below in the section on the preparation of the starting compounds and intermediates.

The compounds according to the invention possess valuable pharmacological properties and can be used for the prevention and/or treatment of various diseases and disease-induced states in humans and in mammals in general.

The compounds according to the invention are potent selective V1a, V2 or dual V1a/V2 receptor antagonists, which inhibit vasopressin activity in vitro and in vivo. In addition, the compounds according to the invention also act as antagonists at the related oxytocin receptor.

The compounds according to the invention are particularly suitable for the prevention and/or treatment of cardiovascular diseases. In this connection, the following may be mentioned by way of example and by way of preference as target indications: acute and chronic heart failure, arterial hypertension, coronary heart disease, stable and unstable angina pectoris, myocardial ischaemia, myocardial infarction, shock, arteriosclerosis, atrial and ventricular arrhythmias, transitory and ischaemic attacks, stroke, inflammatory cardiovascular diseases, peripheral and cardiac vascular diseases, peripheral circulation disorders, arterial pulmonary hypertension, spasms of the coronary arteries and peripheral arteries, thromboses, thromboembolic diseases, oedema formation such as for example pulmonary oedema, cerebral oedema, renal oedema or heart failure-related oedema, and restenoses for example after thrombolysis treatments, percutaneous-transluminal angioplasties (PTA), transluminal coronary angioplasties (PTCA), heart transplants and bypass operations.

In the sense of the present invention, the term heart failure also includes more specific or related disease forms such as right heart failure, left heart failure, global insufficiency, ischaemic cardiomyopathy, dilatative cardiomyopathy, congenital heart defects, heart valve defects, heart failure with heart valve defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined heart valve defects, heart muscle inflammation (myocarditis), chronic myocarditis, acute myocarditis, viral myocarditis, diabetic heart failure, alcohol-toxic cardiomyopathy, cardiac storage diseases, diastolic heart failure and systolic heart failure.

Furthermore, the compounds according to the invention are suitable for use as a diuretic for the treatment of oedemas and in electrolyte disorders, in particular in hypervolaemic and euvolaemic hyponatraemia.

The compounds according to the invention are also suitable for the prevention and/or treatment of polycystic kidney disease (PCKD) and the syndrome of inadequate ADH secretion (SIADH).

In addition, the compounds according to the invention can be used for the prevention and/or treatment of liver cirrhosis, ascites, diabetes mellitus and diabetic complications such as for example neuropathy and nephropathy, acute and chronic kidney failure and chronic renal insufficiency.

Further, the compounds according to the invention are suitable for the prevention and/or treatment of central nervous disorders such as anxiety states and depression, of glaucoma and of cancer, in particular of pulmonary tumours.

In addition, the compounds according to the invention can be used for the prevention and/or treatment of inflammatory diseases, asthmatic diseases, chronic-obstructive respiratory tract diseases (COPD), pain conditions, prostatic hypertrophy, incontinence, bladder inflammation, hyperactive bladder, diseases of the adrenals such as for example pheochromocytoma and adrenal apoplexy, diseases of the intestine such as for example Crohn's disease and diarrhoea, or of menstrual disorders such as for example dysmenorrhoea or of endometriosis.

By virtue of their activity profile, the compounds according to the invention are suitable in particular for the treatment and/or prevention of acute and chronic heart failure, hypervolaemic and euvolaemic hyponatraemia, liver cirrhosis, ascites, oedemas, and the syndrome of inadequate ADH secretion (SIADH).

A further object of the present invention is the use of the compounds according to the invention for the treatment and/or prevention of diseases, in particular of the diseases mentioned above.

A further object of the present invention is the use of the compounds according to the invention for the production of a medicament for the treatment and/or prevention of diseases, in particular of the diseases mentioned above.

A further object of the present invention is the use of the compounds according to the invention in a method for the treatment and/or prevention of diseases, in particular of the diseases mentioned above.

A further object of the present invention is a method for the treatment and/or prevention of diseases, in particular of the diseases mentioned above, with the use of an effective quantity of at least one of the compounds according to the invention.

The compounds according to the invention can be used alone or if necessary in combination with other active substances. A further object of the present invention are medicaments which contain at least one of the compounds according to the invention and one or more other active substances, in particular for the treatment and/or prevention of the diseases mentioned above. As combination active substances suitable for this, the following may be mentioned by way of example and by way of preference:

organic nitrates and NO donors, such as for example sodium nitroprusside, nitroglycerine, isosorbide mononitrate, isosorbide dinitrate, molsidomine or SIN-1, and inhalational NO;

diuretics, in particular loop diuretics and thiazides and thiazide-like diuretics;

positive-inotropically active compounds, such as for example cardiac glycosides (digoxin), and beta-adrenergic and dopaminergic agonists such as isoproterenol, adrenalin, noradrenalin, dopamine and dobutamine;

compounds which inhibit the degradation of cyclic guanosine monophosphate (cGMP) and/or cyclic adenosine monophosphate (cAMP), such as for example inhibitors of phosphodiesterases (PDE) 1, 2, 3, 4 and/or 5, in particular PDE 5 inhibitors such as sildenafil, vardenafil and tadalafil, and PDE 3 inhibitors such as aminone and milrinone;

natriuretic peptides such as for example "atrial natriuretic peptide" (ANP, anaritide), "B-type natriuretic peptide" or "brain natriuretic peptide" (BNP, nesiritide), "C-type natriuretic peptide" (CNP) and urodilatin;

calcium sensitizers, such as for example and preferably levosimendan;

NO- and haem-independent activators of guanylate cyclase, such as in particular cinaciguat and also the compounds described in WO 01/19355, WO 01/19776, WO 01/19778, WO 01/19780, WO 02/070462 and WO 02/070510;

NO-independent, but haem-dependent stimulators of guanylate cyclase, such as in particular riociguat and also the compounds described in WO 00/06568, WO 00/06569, WO 02/42301 and WO 03/095451;

inhibitors of human neutrophil elastase (HNE), such as for example sivelestat or DX-890 (reltran);

compounds inhibiting the signal transduction cascade, such as for example tyrosine kinase inhibitors, in particular sorafenib, imatinib, gefitinib and erlotinib;

compounds influencing the energy metabolism of the heart, such as for example and preferably etomoxir, dichloroacetate, ranolazine or trimetazidine;

agents with antithrombotic action, for example and preferably from the group of the thrombocyte aggregation inhibitors, anticoagulants or profibrinolytic substances;

blood pressure-lowering active substances, for example and preferably from the group of the calcium antagonists, angiotensin AII antagonists, ACE inhibitors, vasopeptidase inhibitors, inhibitors of neutral endopeptidase, endothelin antagonists, renin inhibitors, alpha-receptor blockers, beta-receptor blockers, mineralocorticoid receptor antagonists and rho-kinase inhibitors; and/or active substances modifying the fat metabolism, for example and preferably from the group of the thyroid receptor agonists, cholesterol synthesis inhibitors such as for example and preferably HMG-CoA reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

In a preferred embodiment of the invention, the compounds according to the invention are administered in combination with a diuretic, such as for example and preferably furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerine, isosorbide, mannitol, amiloride or triamterene.

Agents with antithrombotic action are understood preferably to mean compounds from the group of the thrombocyte aggregation inhibitors, anticoagulants or profibrinolytic substances.

In a preferred embodiment of the invention, the compounds according to the invention are administered in combination with a thrombocyte aggregation inhibitor, such as for example and preferably aspirin, clopidogrel, ticlopidine or dipyridamole.

In a preferred embodiment of the invention, the compounds according to the invention are administered in combination with a thrombin inhibitor, such as for example and preferably ximelagatran, melagatran, dabigatran, bivalirudin or clexane.

In a preferred embodiment of the invention, the compounds according to the invention are administered in combination with a GPIIb/IIIa antagonist, such as for example and preferably tirofiban or abciximab.

In a preferred embodiment of the invention, the compounds according to the invention are administered in combination with a factor Xa inhibitor, such as for example and preferably riva-roxaban, DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as for example and preferably coumarin.

Blood pressure-lowering agents are understood preferably to mean compounds from the group of the calcium antagonists, angiotensin AII antagonists, ACE inhibitors, vasopeptidase inhibitors, inhibitors of neutral endopeptidase, endothelin antagonists, renin inhibitors, alpha-receptor blockers, beta-receptor blockers, mineralocorticoid receptor antagonists, rho-kinase inhibitors and diuretics.

In a preferred embodiment of the invention, the compounds according to the invention are administered in combination with a calcium antagonist, such as for example and preferably nifedipine, amlodipine, verapamil or diltiazem.

In a preferred embodiment of the invention, the compounds according to the invention are administered in combination with an angiotensin AII antagonist, such as for example and preferably losartan, candesartan, valsartan, telmisartan or embusartan.

In a preferred embodiment of the invention, the compounds according to the invention are administered in combination with an ACE inhibitor, such as for example and preferably enalapril, captopril, lisinopril, ramipril, delapril, fosinopril, quinopril, perindopril or trandopril.

In a preferred embodiment of the invention, the compounds according to the invention are administered in combination with a vasopeptidase inhibitor or inhibitor of neutral endopeptidase (NEP), such as for example and preferably omapatrilat or AVE-7688.

In a preferred embodiment of the invention, the compounds according to the invention are administered in combination with an endothelin antagonist, such as for example and preferably bosentan, darusentan, ambrisentan or sitaxsentan.

In a preferred embodiment of the invention, the compounds according to the invention are administered in combination with a renin inhibitor, such as for example and preferably aliskiren, SPP-600 or SPP-800.

In a preferred embodiment of the invention, the compounds according to the invention are administered in combination with an alpha-1 receptor blocker, such as for example and preferably prazosin.

In a preferred embodiment of the invention, the compounds according to the invention are administered in combination with a beta-receptor blocker, such as for example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a mineralocorticoid receptor antagonist, such as for example and preferably spironolactone, eplerenone, canrenone or potassium canrenoate.

In a preferred embodiment of the invention, the compounds according to the invention are administered in combination with a rho-kinase inhibitor, such as for example and preferably fasudil, Y-27632, SLx-2119, BF-66851, BF-66852, BF-66853, KI-23095 or BA-1049.

Fat metabolism-modifying agents are understood preferably to mean compounds from the group of the CETP inhibitors, thyroid receptor agonists, cholesterol synthesis inhibitors such as HMG-CoA reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein(a) antagonists.

In a preferred embodiment of the invention, the compounds according to the invention are administered in combination with a CETP inhibitor, such as for example and preferably torcetrapib, dalcetrapib, anacetrapib BAY 60-5521, or CETP-vaccine (CETi-1).

In a preferred embodiment of the invention, the compounds according to the invention are administered in combination with a thyroid receptor agonist, such as for example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of the statins, such as for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, such as for example and preferably BMS-188494 or TAK-475.

In a preferred embodiment of the invention, the compounds according to the invention are administered in combination with an ACAT inhibitor, such as for example and preferably avasimibe, melinamide, pactimibe, eflucimibe or SMP-797.

In a preferred embodiment of the invention, the compounds according to the invention are administered in combination with an MTP inhibitor, such as for example and preferably implitapide, BMS-201038, R-103757 or JTT-130.

In a preferred embodiment of the invention, the compounds according to the invention are administered in combination with a PPAR-gamma agonist, such as for example and preferably pio-glitazone or rosiglitazone.

In a preferred embodiment of the invention, the compounds according to the invention are administered in combination with a PPAR-delta agonist, such as for example and preferably GW-501516 or BAY 68-5042.

In a preferred embodiment of the invention, the compounds according to the invention are administered in combination with a cholesterol absorption inhibitor, such as for example and preferably ezetimibe, tiqueside or pamaqueside.

In a preferred embodiment of the invention, the compounds according to the invention are administered in combination with a lipase inhibitor, such as for example and preferably orlistat.

In a preferred embodiment of the invention, the compounds according to the invention are administered in combination with a polymeric bile acid adsorber, such as for example and preferably cholestyramine, colestipol, colesolvam, cholestagel or colestimide.

In a preferred embodiment of the invention, the compounds according to the invention are administered in combination with a bile acid reabsorption inhibitor, such as for example and preferably ASBT (=IBAT) inhibitors such as for example AZD-7806, S-8921, AK-105, BARI-1741, SC-435 or SC-635.

In a preferred embodiment of the invention, the compounds according to the invention are administered in combination with a lipoprotein(a) antagonist, such as for example and preferably gemcabene calcium (CI-1027) or nicotinic acid.

A further object of the present invention are medicaments which contain at least one compound according to the invention, usually together with one or more inert, non-toxic, pharmaceutically suitable auxiliaries, and the use thereof for the aforesaid purposes.

The compounds according to the invention can act systemically and/or locally. For this purpose, they can be administered in a suitable manner, such as for example by the oral, parenteral, pulmonary, nasal, sublingual, lingual, buccal, rectal, dermal, transdermal, conjunctival or otic routes or as an implant or stent.

For these administration routes, the compounds according to the invention can be administered in suitable administration forms.

For oral administration, administration forms which function according to the state of the art, and release the compounds according to the invention rapidly and/or in a modified manner, which contain the compounds according to the invention in crystalline and/or amorphized and/or dissolved form, such as for example tablets (uncoated or coated tablets, for example with gastric juice-resistant or delayed dissolution or insoluble coatings, which control the release of the compound according to the invention), tablets rapidly disintegrating in the oral cavity or films/wafers, films/lyophilizates, capsules (for example hard or soft gelatine capsules), sugar-coated tablets, granules, pellets, powders, emulsions, suspensions, aerosols or solutions are suitable.

Parenteral administration can be effected by omitting an absorption step (e.g. intravenous, intra-arterial, intracardial, intraspinal or intralumbar administration) or by involving absorption (e.g. intra-muscular, subcutaneous, intracutaneous, percutaneous or intraperitoneal administration). Suitable administration forms for parenteral administration include injection and infusion preparations in the form of solutions, suspensions, emulsions, lyophilizates or sterile powders.

For the other administration routes, for example inhalation formulations (including powder inhalers and nebulizers), nasal drops, solutions or sprays, tablets for lingual, sublingual or buccal administration, tablets, films/wafers or capsules, suppositories, aural or ophthalmic preparations, vaginal capsules, aqueous suspensions (lotions, shakeable mixtures), lipophilic suspensions, ointments, creams, transdermal therapeutic systems (e.g. plasters), milk, pastes, foams, dusting powders, implants or stents are suitable.

Oral or parenteral administration, in particular oral and intravenous administration, are preferred.

The compounds according to the invention can be converted into the stated administration forms. This can be effected in a manner known per se by mixing with inert, non-toxic, pharmaceutically suitable auxiliaries. These auxiliaries include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as for example ascorbic acid), colourants (e.g. inorganic pigments such as for example iron oxides) and flavour and/or odour correctors.

In general, to achieve effective results in parenteral administration it has been found advantageous to administer quantities of about 0.001 to 10 mg/kg, preferably about 0.01 to 1 mg/kg body weight. In oral administration, the dosage is about 0.01 to 100 mg/kg, preferably about 0.01 to 20 mg/kg and quite especially preferably 0.1 to 10 mg/kg body weight.

Nonetheless it can sometimes be necessary to deviate from said quantities, namely depending on body weight, administration route, individual response to the active substance, nature of the preparation and time or interval at which the administration takes place. Thus in some cases it can be sufficient to manage with less than the aforesaid minimum quantity, while in other cases the stated upper limit must be exceeded. In the event of administration of larger quantities, it may be advisable to divide these into several individual administrations throughout the day.

The following working examples illustrate the invention. The invention is not limited to the examples.

Unless otherwise stated, the percentages stated in the following tests and examples are percent by weight, parts are parts by weight, and solvent ratios, dilution ratios and concentration information about liquid/liquid solutions are each based on volume.

A. EXAMPLES

Abbreviations and Acronyms
Ac acetyl
Alk alkyl
Boc tert-butoxycarbonyl
CI chemical ionization (in MS)
DCI direct chemical ionization (in MS)
DME 1,2-dimethoxyethane
DMF N,N-dimethylformamide
DMPU 1,3-dimethyltetrahydro-2(1H)-pyrimidinone
DMSO dimethyl sulphoxide
EDC N'-(3-dimethylaminopropyl)-N-ethylcarbodiimide hydrochloride
ee enantiomeric excess
eq. equivalent(s)
ESI electrospray ionization (in MS)
h hour(s)
Hal halogen
HOBt 1-hydroxy-1H-benzotriazole hydrate
HPLC high pressure, high performance liquid chromatography
conc. concentrated
LC/MS liquid chromatography-coupled mass spectrometry
LDA lithium diisopropylamide
LiHMDS lithium hexamethyldisilazane
min minute(s)
MS mass spectrometry
MTBE methyl tert-butyl ether
NMR nuclear magnetic resonance spectrometry
OAc acetate
p para
Ph phenyl
quant. quantitative (yield)
rac racemic/racemate
RT room temperature
$R_t$ retention time (in HPLC)
THF tetrahydrofuran
UV ultraviolet spectrometry
v/v ratio by volume (of a solution)
tog. together
LC/MS and HPLC Methods:
Method 1 (LC/MS):
 MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 2 (LC/MS):
 Instrument: Micromass Quattro Micro MS with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 3 (LC/MS):
 Instrument: Micromass QuattroPremier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient 0.0 min 90% A→0.1 min 90% A→1.5 min 10% A→2.2 min 10% A; flow rate: 0.33 ml/min; oven: 50° C.; UV detection: 210 nm.

Method 4 (LC/MS):
 Instrument: Waters Acquity SQD UPLC System; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.

Method 5 (Chiral Preparative HPLC):
 Chiral stationary silica gel phase based on the selector poly(N-methacryloyl-L-leucine-(+)-3-pinanemethylamide); column: 600 mm×30 mm; temperature: 24° C.; UV detection: 265 nm; flow rate: 80 ml/min; mobile phase:
  Method 5a: 0-13.1 min isohexane/ethyl acetate 25:75 (v/v), 13.11-19.1 min 100% ethyl acetate, 19.11-23.5 min isohexane/ethyl acetate 25:75 (v/v);
  Method 5b: 100% ethyl acetate.

Method 6 (Chiral Analytical HPLC):
 Chiral stationary silica gel phase based on the selector poly(N-methacryloyl-L-leucine-(+)-3-pinanemethylamide); column: 250 mm×4.6 mm; temperature: 24° C.; UV detection: 265 nm; flow rate: 2 ml/min; mobile phase:
  Method 6a: isohexane/ethyl acetate 1:4 (v/v);
  Method 6b: 100% ethyl acetate.

Method 7 (Preparative HPLC):
 Column: YMC ODS C18, 10 μm, 250 mm×30 mm; mobile phase A: 0.1% formic acid in water, mobile phase B: acetonitrile; flow rate: 50 ml/min; program: 0-6 min 10% B, 6-27 min gradient to 95% B, 27-43 min 95% B, 43-45 min gradient to 10% B, 45-50 min 10% B.

Method 8 (Preparative HPLC):
 Column: Grom-Sil 120 ODS-4HE, 10 μm, 250 mm×30 mm; mobile phase A: 0.1% formic acid in water, mobile phase B: acetonitrile; flow rate: 50 ml/min; program: 0-3 min 10% B, 3-27 min gradient to 95% B, 27-34 min 95% B, 34-38 min 10% B.

Method 9 (Preparative HPLC):
 Column: Grom-Sil 120 ODS-4HE, 10 μm, 250 mm×30 mm; mobile phase A: 0.1% formic acid in water, mobile phase B: acetonitrile; flow rate: 50 ml/min; program: 0-6 min 5% B, 6-34 min gradient to 95% B, 34-38 min 95% B, 38-45 min 5% B.

Method 10 (Chiral Preparative HPLC):
 Chiral stationary silica gel phase based on the selector poly(N-methacryloyl-D-leucine-dicyclopropylmethylamide); column: 670 mm×40 mm; flow rate: 80 ml/min; temperature: 24° C.; UV detection: 260 nm; mobile phase:
  Method 10a: isohexane/ethyl acetate 20:80 (v/v);
  Method 10b: isohexane/ethyl acetate 15:85 (v/v).
Method 11 (Chiral Analytical HPLC):
  Chiral stationary silica gel phase based on the selector poly(N-methacryloyl-D-leucine-dicyclopropylmethylamide); column: 250 mm×4.6 mm; mobile phase: 100% ethyl acetate; flow rate: 2 ml/min; temperature: 24° C.; UV detection: 265 nm.
Method 12 (Preparative HPLC):
  Column: Grom-Sil 120 ODS-4HE, 10 µm, 250 mm×30 mm; mobile phase A: 0.1% formic acid in water, mobile phase B: methanol; flow rate: 50 ml/min; program: 0-6 min 20% B, 6-27 min gradient to 98% B, 27-53 min 98% B, 53-54 min gradient to 20% B, 54-61 min 20% B.
Method 13 (Chiral Preparative HPLC):
  Stationary phase: Daicel Chiralpak AS-H, 5 µm; column: 250 mm×20 mm; mobile phase: isohexane/methanol/n-propanol 95:2.5:2.5 (v/v/v); flow rate: 20 ml/min; temperature: RT; UV detection: 230 nm.
Method 14 (Chiral Analytical HPLC):
  Stationary phase: Daicel Chiralpak AS-H, 5 µm; column: 250 mm×4 mm; mobile phase: isohexane/methanol/ethanol 92:4:4 (v/v/v); flow rate 1 ml/min; UV detection: 220 nm.
Method 15 (Chiral Preparative HPLC):
  Chiral stationary mercapto silica gel phase based on the selector poly(N-methacryloyl-L-isoleucine-3-pentylamide); column: 430 mm×40 mm; mobile phase: 100% ethyl acetate; flow rate: 80 ml/min; temperature: 24° C.; UV detection: 265 nm.
Method 16 (Chiral Analytical HPLC):
  Chiral stationary mercapto silica gel phase based on the selector poly(N-methacryloyl-L-isoleucine-3-pentylamide); column: 250 mm×4.6 mm; mobile phase: 100% ethyl acetate; flow rate: 2 ml/min; temperature: 24° C.; UV detection: 265 nm.
Method 17 (Chiral Preparative HPLC):
  Stationary phase: Daicel Chiralpak AD-H, 10 µm; column: 250 mm×20 mm; temperature: RT; UV detection: 230 nm; flow rate: 20 ml/min; mobile phase:
  Method 17a: isohexane/isopropanol 60:40 (v/v);
  Method 17b: isohexane/isopropanol 70:30 (v/v);
  Method 17c: isohexane/ethanol 75:25 (v/v).
Method 18 (Chiral Analytical HPLC):
  Stationary phase: Daicel Chiralpak AD-H, 5 µm; column: 250 mm×4.6 mm; temperature: 30° C.; UV detection: 230 nm; flow rate: 1.0 ml/min; mobile phase:
  Method 18a: isohexane/isopropanol 50:50 (v/v);
  Method 18b: isohexane/ethanol 70:30 (v/v).
Method 19 (Preparative HPLC):
  Column: Reprosil C18, 10 µm, 250 mm×30 mm; mobile phase A: 0.1% formic acid in water, mobile phase B: methanol; flow rate: 50 ml/min; program: 0-6 min 30% B, 6-33 min gradient to 95% B, 33-42 min 95% B, 42-43 min gradient to 30% B, 43-50 min 30% B.
Method 20 (Preparative HPLC):
  Column: Reprosil C18, 10 µm, 250 mm×40 mm; mobile phase A: 0.1% formic acid in water, mobile phase B: acetonitrile; flow rate: 50 ml/min; program: 0-6 min 10% B, 6-40 min gradient to 95% B, 40-53 min 95% B, 53-54 min gradient to 10% B, 54-57 min 10% B.
Method 21 (LC/MS):
  MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.
Method 22 (LC/MS):
  MS instrument type: Micromass ZQ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 23 (Preparative HPLC):
  Column: Reprosil C18, 10 µm, 250 mm×30 mm; mobile phase A: 0.1% formic acid in water, mobile phase B: acetonitrile; flow rate: 50 ml/min; program: 0-6 min 10% B, 6-27 min gradient to 95% B, 27-38 min 95% B, 38-39 min gradient to 10% B, 39-40 min 10% B.

Starting Compounds and Intermediates

Example 1A

Ethyl N-({2-[(4-chlorophenyl)carbonyl]hydrazinyl}carbonyl)glycinate

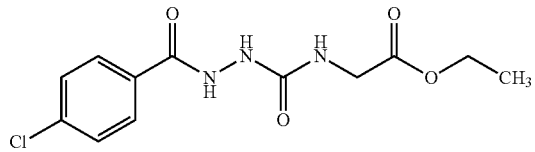 [SMILES: CCOC(=O)CNC(=O)NNC(=O)c1ccc(Cl)cc1]

A suspension of 12.95 g (75.9 mmol) of 4-chlorobenzohydrazide in 50 ml of dry THF was initially charged at 50° C., and a solution of 10.0 g (77.5 mmol) of ethyl 2-isocyanatoacetate in 100 ml of dry THF was added dropwise. Initially, a solution was formed, and then a precipitate. After the addition had ended, the mixture was stirred at 50° C. for a further 2 h and then allowed to stand at RT overnight. The crystals were isolated by filtration, washed with a little diethyl ether and dried under high vacuum. This gave 21.43 g (89% of theory) of the title compound.

LC/MS [Method 1]: $R_t$=1.13 min; m/z=300 (M+H)$^+$ $^1$H NMR (DMSO-d$_6$, 400 MHz): δ=1.19 (t, 3H), 3.77 (d, 2H), 4.09 (q, 2H), 6.88 (br. s, 1H), 7.57 (d, 2H), 7.91 (d, 2H), 8.21 (s, 1H), 10.29 (s, 1H).

Example 2A

[3-(4-Chlorophenyl)-5-oxo-1,5-dihydro-4H-1,2,4-triazol-4-yl]acetic acid

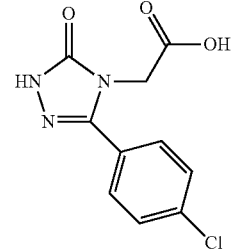 [SMILES: O=C(O)Cn1c(-c2ccc(Cl)cc2)n[nH]c1=O]

91 ml of a 3N aqueous sodium hydroxide solution were added to 21.43 g (67.9 mmol) of the compound of Example 1A, and the mixture was heated at reflux overnight. After cooling to RT, the mixture was adjusted to pH 1 by slow addition of about 20% strength hydrochloric acid. The precipitated solid was isolated by filtration, washed with water and dried under reduced pressure at 60° C. This gave 17.55 g of the title compound in a purity of about 88% (90% of theory).

LC/MS [Method 1]: $R_t$=0.94 min; m/z=254 (M+H)$^+$ $^1$H NMR (DMSO-d$_6$, 400 MHz): δ=4.45 (s, 2H), 7.65-7.56 (m, 4H), 12.09 (s, 1H), 13.25 (br. s, 1H).

Example 3A 5-(4-Chlorophenyl)-4-(3,3,3-trifluoro-2-oxopropyl)-2,4-dihydro-3H-1,2,4-triazol-3-one (Ketone Form) or 5-(4-chlorophenyl)-4-(3,3,3-trifluoro-2,2-dihydroxypropyl)-2,4-dihydro-3H-1,2,4-triazol-3-one (Hydrate Form)

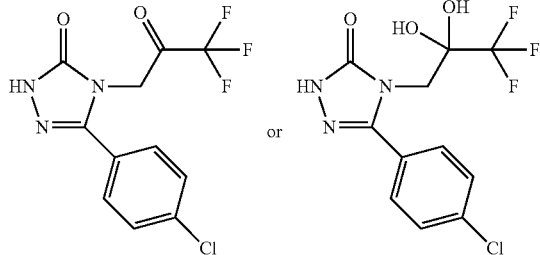 [SMILES: O=C(Cn1c(-c2ccc(Cl)cc2)n[nH]c1=O)C(F)(F)F ; O=c1[nH]nc(-c2ccc(Cl)cc2)n1CC(O)(O)C(F)(F)F]

Under argon, 5.0 g (16.36 mmol) of the compound of Example 2A were dissolved in 200 ml of pyridine, and 17.18 g (81.8 mmol) of trifluoroacetic anhydride were then added. During the addition, the temperature increased to about 35° C. After 30 min, the pyridine was removed on a rotary evaporator and 1.5 l of 0.5N hydrochloric acid were added to the residue. This mixture was heated to 70° C. and then filtered whilst still hot. The solid was washed with a little water. The entire filtrate was extracted three times with ethyl acetate. The combined organic phases were washed with water, then with a saturated sodium bicarbonate solution, then with a saturated sodium chloride solution, dried over sodium sulphate and freed from the solvent on a rotary evaporator. The residue was dried under high vacuum. This gave 3.56 g (68% of theory) of the title compound in hydrate form.

LC/MS [Method 1]: $R_t$=1.51 min; m/z=306 (M+H)$^+$ and 324 (M+H)$^+$ (ketone or hydrate form)

$^1$H NMR (DMSO-d$_6$, 400 MHz): δ=3.98 (s, 2H), 7.61 (d, 2H), 7.68 (br. s, 2H), 7.72 (d, 2H), 12.44 (s, 1H).

Example 4A 5-(4-Chlorophenyl)-4-(3,3,3-trifluoro-2-hydroxypropyl)-2,4-dihydro-3H-1,2,4-triazol-3-one

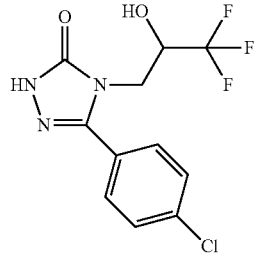 [SMILES: O=c1[nH]nc(-c2ccc(Cl)cc2)n1CC(O)C(F)(F)F]

3.56 g (11.0 mmol) of the compound of Example 3A were dissolved in 100 ml of methanol, and 3.75 g (99.5 mmol) of sodium borohydride were added with ice cooling. After 1.5 h, 200 ml of 1M hydrochloric acid were added slowly. The methanol was removed on a rotary evaporator, and the residue was diluted with 500 ml of water and extracted three times with ethyl acetate. The combined organic phases were washed with a saturated sodium bicarbonate solution and then with a saturated sodium chloride solution, dried over sodium sulphate and freed from the solvent on a rotary evaporator. The residue was dried under high vacuum. This gave 3.04 g (90% of theory) of the title compound.

LC/MS [Method 2]: $R_t$=1.80 min; m/z=308 (M+H)$^+$ $^1$H NMR (DMSO-d$_6$, 400 MHz): δ=3.77 (dd, 1H), 3.92 (dd, 1H), 4.34-4.23 (m, 1H), 6.85 (d, 1H), 7.62 (d, 2H), 7.75 (d, 2H), 12.11 (s, 1H).

Example 5A

Methyl {3-(4-chlorophenyl)-5-oxo-4-(3,3,3-trifluoro-2-hydroxypropyl)-4,5-dihydro-1H-1,2,4-triazol-1-yl}acetate (Racemate)

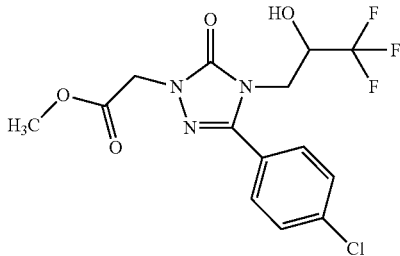 [SMILES: COC(=O)Cn1nc(-c2ccc(Cl)cc2)n(CC(O)C(F)(F)F)c1=O]

3.04 g (9.9 mmol) of the compound of Example 4A were dissolved in 100 ml of acetonitrile, and 1.07 g (9.9 mmol) of methyl chloroacetate, 2.73 g (19.8 mmol) of potassium carbonate and a small spatula tip of potassium iodide were added. The reaction mixture was heated at reflux for 1 h, allowed to cool to RT and filtered. The filtrate was freed from the volatile components on a rotary evaporator and the residue was dried under high vacuum. This gave 3.70 g of the title compound in a purity of about 90% (89% of theory).

LC/MS [Method 3]: $R_t$=1.10 min; m/z=380 (M+H)$^+$ $^1$H NMR (DMSO-d$_6$, 400 MHz): δ=3.70 (s, 3H), 3.84 (dd, 1H), 3.99 (dd, 1H), 4.16-4.35 (m, 1H), 4.72 (s, 2H), 6.91 (d, 1H), 7.64 (d, 2H), 7.78 (d, 2H).

The racemic compound of Example 5A was separated by preparative HPLC on a chiral phase into the enantiomers [sample preparation: 3.6 g of racemate dissolved in 54 ml of ethyl acetate/iso-hexane (1:1 v/v), separated in three portions on the column; column: chiral silica gel phase based on the selector poly(N-methacryloyl-L-isoleucine-3-pentylamide), 430 mm×40 mm; mobile phase: stepped gradient isohexane/ethyl acetate 1:1→ethyl acetate→isohexane/ethyl acetate 1:1; flow rate: 50 ml/min; temperature: 24° C.; UV detection: 260 nm]. In this manner, 1.6 g of the first-eluting enantiomer 1 (Example 6A) and 1.6 g of the later-eluting enantiomer 2 (Example 7A) were obtained:

Example 6A

Methyl {3-(4-chlorophenyl)-5-oxo-4-[(2 S)-3,3,3-trifluoro-2-hydroxypropyl]-4,5-dihydro-1H-1,2,4-triazol-1-yl}acetate) (Enantiomer 1)

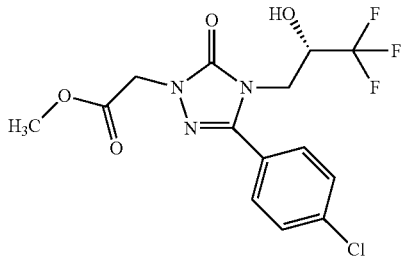 [SMILES: COC(=O)Cn1nc(-c2ccc(Cl)cc2)n(C[C@H](O)C(F)(F)F)c1=O]

First-eluting enantiomer from the racemate separation of Example 5A.

$R_t$=3.21 min [column: chiral silica gel phase based on the selector poly(N-methacryloyl-L-isoleucine-3-pentylamide), 250 mm×4.6 mm; mobile phase: isohexane/ethyl acetate 1:1; flow rate: 1 ml/min; UV detection: 260 nm].

Example 7A

Methyl {3-(4-chlorophenyl)-5-oxo-4-[(2R)-3,3,3-trifluoro-2-hydroxypropyl]-4,5-dihydro-1H-1,2,4-triazol-1-yl}acetate (Enantiomer 2)

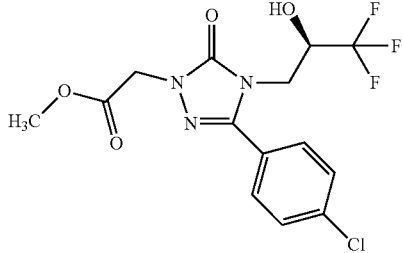 [SMILES: COC(=O)Cn1nc(-c2ccc(Cl)cc2)n(C[C@@H](O)C(F)(F)F)c1=O]

Last-eluting enantiomer from the racemate separation of Example 5A.

$R_t$=4.48 min [column: chiral silica gel phase based on the selector poly(N-methacryloyl-L-isoleucine-3-pentylamide), 250 mm×4.6 mm; mobile phase: isohexane/ethyl acetate 1:1; flow rate: 1 ml/min; UV detection: 260 nm].

Example 8A

{3-(4-Chlorophenyl)-5-oxo-4-[(2S)-3,3,3-trifluoro-2-hydroxypropyl]-4,5-dihydro-1H-1,2,4-triazol-1-yl}acetic acid

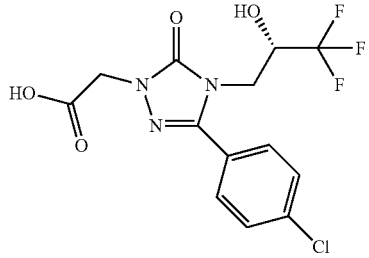 [SMILES: O=C(O)Cn1nc(-c2ccc(Cl)cc2)n(C[C@H](O)C(F)(F)F)c1=O]

The enantiomerically pure compound of Example 6A (1.6 g, 4.21 mmol) was dissolved in 77 ml of methanol, and 17 ml of a 1M solution of lithium hydroxide in water were added. The mixture was stirred at RT for 1 h and then concentrated on a rotary evaporator. The residue was diluted with 100 ml of water and acidified to pH 1-2 with 1 N hydrochloric acid. The precipitated product was filtered off, washed successively with water and cyclohexane and sucked dry. Further drying under high vacuum gave 1.1 g (71% of theory) of the title compound.

$[\alpha]_D^{20}$=+3.4° (methanol, c=0.37 g/100 ml)

LC/MS [Method 1]: $R_t$=1.51 min; m/z=366 (M+H)$^+$ $^1$H NMR (400 MHz, DMSO-d$_6$): δ=3.84 (dd, 1H), 4.00 (dd, 1H), 4.25 (m, 1H), 4.58 (s, 2H), 6.91 (d, 1H), 7.63 (d, 2H), 7.78 (d, 2H), 13.20 (br. s, 1H).

Example 9A

{3-(4-Chlorophenyl)-5-oxo-4-[(2R)-3,3,3-trifluoro-2-hydroxypropyl]-4,5-dihydro-1H-1,2,4-triazol-1-yl}acetic acid

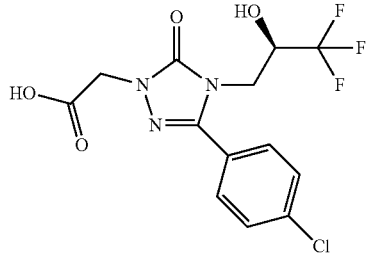 [SMILES: O=C(O)Cn1nc(-c2ccc(Cl)cc2)n(C[C@@H](O)C(F)(F)F)c1=O]

The title compound was obtained analogously to Example 8A starting with Example 7A.

$[\alpha]_D^{20}$=−4.6° (methanol, c=0.44 g/100 ml)

LC/MS [Method 1]: $R_t$=1.53 min; m/z=366 (M+H)$^+$ $^1$H NMR (400 MHz, DMSO-d$_6$): δ=3.84 (dd, 1H), 4.00 (dd, 1H), 4.25 (m, 1H), 4.58 (s, 2H), 6.91 (d, 1H), 7.63 (d, 2H), 7.78 (d, 2H), 13.20 (br. s, 1H).

Example 10A

Ethyl 3-amino-2-[2-(trifluoromethyl)phenyl]propanoate

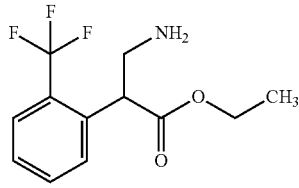 [SMILES: CCOC(=O)C(CN)c1ccccc1C(F)(F)F]

1.035 g (2.54 mmol) of ethyl 3-{[(benzyloxy)carbonyl]amino}-2-[2-(trifluoromethyl)phenyl]propanoate [for the preparation see Example 193A in WO 2007/134862] were dissolved in 24 ml of ethanol and hydrogenated in the presence of 100 mg of 10% palladium on carbon for 3 h at atmospheric pressure. The catalyst was then filtered off and the filtrate was freed from the solvent on a rotary evaporator. The residue corresponded to the title compound.

Yield: 700 mg (96% of theory, 91% pure according to LC/MS)

LC/MS [Method 3]: $R_t$=0.72 min; m/z=262 (M+H)$^+$ $^1$H NMR (400 MHz, DMSO-$d_6$): δ [ppm]=1.12 (t, 3H), 1.73 (br. s, 2H), 2.82 (dd, 1H), 3.14 (dd, 1H), 3.94 (dd, 1H), 4.01-4.16 (m, 2H), 7.49 (t, 1H), 7.58 (d, 1H), 7.67 (t, 1H), 7.73 (d, 1H).

Example 11A

3-Amino-2-[2-(trifluoromethyl)phenyl]propan-1-ol hydrochloride

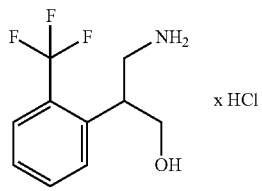 [SMILES: NCC(CO)c1ccccc1C(F)(F)F]

A solution of 700 mg (2.44 mmol) of ethyl 3-amino-2-[2-(trifluoromethyl)phenyl]propanoate (Example 10A) in 10 ml of diethyl ether was slowly added dropwise to a lithium aluminium hydride solution (1 M in diethyl ether, 3.9 ml, 3.9 mmol) which had been pre-cooled to 0° C. After the addition had ended, the reaction mixture was heated under reflux for 1 h and then once more cooled to 0° C. A few drops of water were added until the evolution of hydrogen had ceased. The reaction mixture was then filtered and 1 ml of a 4 N solution of hydrogen chloride in dioxane was added to the filtrate. The precipitated solid was isolated by filtration, washed with a little diethyl ether and dried under high vacuum. This gave 390 mg (63% of theory) of the title compound.

LC/MS [Method 2]: $R_t$=0.91 min; m/z=220 (M+H)$^+$ $^1$H NMR (400 MHz, DMSO-$d_6$): δ [ppm]=3.08 (br. t, 1H), 3.33-3.44 (m, 2H), 3.57-3.69 (m, 2H), 5.34 (t, 1H), 7.46-7.55 (m, 1H), 7.64-7.71 (m, 2H), 7.73 (d, 1H), 7.93 (br. s, 3H).

Example 12A tert-Butyl {3-hydroxy-2-[2-(trifluoromethyl)phenyl]propyl}carbamate

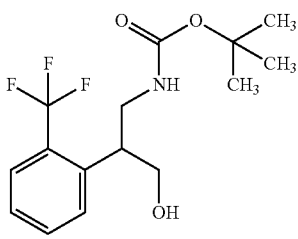 [SMILES: CC(C)(C)OC(=O)NCC(CO)c1ccccc1C(F)(F)F]

265 mg (1.21 mmol) of di-tert-butyl dicarbonate were added to a mixture of 310 mg (1.21 mmol) of the compound of Example 11A in 9.3 ml of dioxane and 9.3 ml of a 5% strength aqueous sodium bicarbonate solution, and the solution was stirred at RT until the reaction had gone to completion. The mixture was then extracted three times with ethyl acetate. The combined organic phases were dried over sodium sulphate and freed from the solvent on a rotary evaporator. The residue (440 mg) corresponded to the title compound and was used without further purification for the next reaction.

LC/MS [Method 3]: $R_t$=1.16 min; m/z=342 (M+Na)$^+$.

Example 13A

3-Amino-2-[2-(trifluoromethyl)phenyl]propylcarbamate hydrochloride

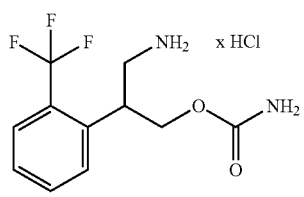 [SMILES: NCC(COC(N)=O)c1ccccc1C(F)(F)F]

A solution of 387 mg (1.21 mmol) of the compound of Example 12A in 19.3 ml of acetonitrile was cooled to −15° C., and 148 μl (1.70 mmol) of chlorosulphonyl isocyanate were added. After 5 min, 10 ml of water were added and stirring of the reaction mixture was continued at 60° C. overnight. After cooling to RT, 10 ml of a saturated aqueous sodium bicarbonate solution were added. The mixture was extracted four times with ethyl acetate. The combined organic phases were dried over sodium sulphate and freed from the solvent on a rotary evaporator. 5 ml of a 4 N solution of hydrogen chloride in dioxane were added to the residue and the mixture was stirred for 5 min Once more, the volatile components were then removed on a rotary evaporator. The residue (300 mg, about 90% pure) corresponded to the title compound and was reacted further without further purification.

LC/MS [Method 4]: $R_t$=0.42 min; m/z=262 (M+H)$^+$ $^1$H NMR (400 MHz, DMSO-$d_6$): δ [ppm]=3.04-3.16 (m, 1H), 3.23-3.34 (m, 1H), 3.53-3.64 (m, 1H), 4.13 (dd, 1H), 4.24 (dd, 1H), 6.41-6.74 (br. s, 2H), 7.53 (t, 1H), 7.66-7.78 (m, 3H), 8.05 (br. s, 3H).

Example 14A tert-Butyl [2-(2-chlorophenyl)-3-hydroxypropyl]carbamate

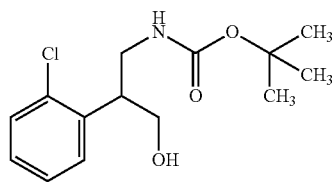 [SMILES: CC(C)(C)OC(=O)NCC(CO)c1ccccc1Cl]

705 mg (3.23 mmol) of di-tert-butyl dicarbonate were added to a solution of 300 mg (1.62 mmol) of 3-amino-2-(2-chlorophenyl)propan-1-ol [for the preparation see Example 9h in *Arch. Pharm.* 1968, 301 (10), 750-762] in 14 ml of dichloromethane, and the mixture was stirred at RT for 3 h. The mixture was then diluted with 100 ml of ethyl acetate and washed successively with 1 M hydrochloric acid (twice), saturated sodium bicarbonate solution and saturated sodium chloride solution. The organic phase was dried over sodium sulphate and freed from the solvent on a rotary evaporator. The residue was purified by preparative HPLC (Method 7). This gave 382 mg (83% of theory) of the title compound as a colourless oil.

LC/MS [Method 4]: $R_t$=0.98 min; m/z=286 (M+H)$^+$.

Example 15A

3-Amino-2-(2-chlorophenyl)propyl carbamate

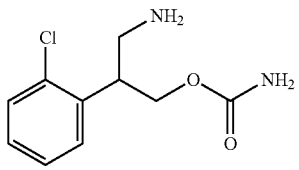 [SMILES: NCC(COC(N)=O)c1ccccc1Cl]

A solution of 344 mg (1.20 mmol) of the compound of Example 14A in 86 ml of acetonitrile was cooled to −15° C., and 314 μl (3.61 mmol) of chlorosulphonyl isocyanate were added. After 5 min, 10 ml of water were added and stirring of the reaction mixture was continued at 60° C. overnight. After cooling to RT, 10 ml of a saturated aqueous sodium bicarbonate solution were added. The mixture was extracted four times with ethyl acetate. The combined organic phases were dried over sodium sulphate and freed from the solvent on a rotary evaporator. The residue (118 mg, about 85% pure, about 37% of theory) corresponded to the title compound and was reacted further without further purification.

LC/MS [Method 2]: $R_t$=0.92 min; m/z=229 (M+H)$^+$ $^1$H NMR (400 MHz, DMSO-d$_6$): δ [ppm]=2.78-2.90 (m, 2H), 3.31 (br. s, 2H), 3.39-3.51 (m, 1H), 4.17 (dd, 1H), 4.24 (dd, 1H), 6.25-6.60 (br. s, 2H), 7.25 (dt, 1H), 7.32 (dt, 1H), 7.39 (dd, 1H), 7.43 (dd, 1H).

Example 16A

Methyl 3-(1,3-dioxo-1,3-dihydro-2H-isoindol-2-yl)-2-[3-(trifluoromethyl)phenyl]propanoate

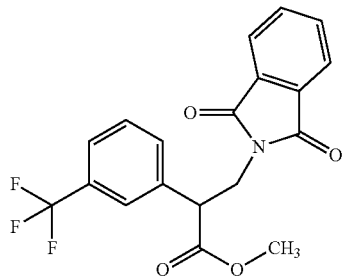 [SMILES: COC(=O)C(CN1C(=O)c2ccccc2C1=O)c1cccc(C(F)(F)F)c1]

Over about 5 min, a solution of n-butyllithium (1.6 M in hexane, 18.75 ml, 30 mmol) was added dropwise to a solution, pre-cooled to −20° C., of 4.91 ml (35 mmol) of diisopropylamine in 50 ml of THF. The LDA solution obtained in this manner was cooled to −78° C., and 15.1 ml of DMPU (1,3-dimethyltetrahydro-2(1H)-pyrimidinone, 125 mmol) were added. After 20 min at −78° C., a solution of 5.45 g (25 mmol) of methyl [3-(trifluoromethyl)phenyl]acetate in 35 ml of THF was slowly added dropwise. After a further 20 min at −78° C., a solution of 7.20 g (30 mmol) of N-bromomethylphthalimide in 50 ml of THF was added dropwise. Stirring of the reaction mixture was continued initially at −78° C. for 1 h, then without cooling bath at RT overnight. After addition of 100 ml of 1 N hydrochloric acid, the mixture was extracted three times with ethyl acetate. The combined organic phases were washed with saturated sodium chloride solution, dried over sodium sulphate and freed from the solvent on a rotary evaporator. The residue was dissolved in 50 ml of DMSO and purified in several portions by preparative HPLC [Method 8]. This gave 2.20 g (22% of theory) of the title compound.

LC/MS [Method 3]: $R_t$=1.32 min; m/z=378 (M+H)$^+$ $^1$H NMR (400 MHz, DMSO-d$_6$): δ [ppm]=3.33 (s, 3H), 4.07 (dd, 1H), 4.19 (dd, 1H), 4.33 (dd, 1H), 7.50-7.57 (m, 1H), 7.58-7.66 (m, 3H), 7.75-7.87 (m, 4H).

Example 17A tert-Butyl {3-hydroxy-2-[3-(trifluoromethyl)phenyl]propyl}carbamate

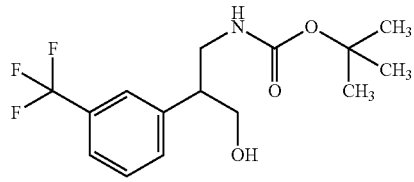 [SMILES: CC(C)(C)OC(=O)NCC(CO)c1cccc(C(F)(F)F)c1]

550 mg (1.46 mmol) of the compound of Example 16A were initially charged in 19 ml of a mixture of 2-propanol and water (6:1 v/v), and 276 mg (7.29 mmol) of sodium borohydride were added. The reaction mixture was stirred at RT overnight and then adjusted to pH 5 by addition of glacial acetic acid. The resulting mixture was heated to 80° C., and stirring was continued at this temperature overnight. An analytical sample showed that, according to LC/MS, the free 3-amino-2-[3-(trifluoromethyl)phenyl]propan-1-ol was the main component [LC/MS (Method 3): $R_t$=1.02 min, m/z=220 (M+H)$^+$]. After slight cooling, the reaction mixture was freed from the volatile components on a rotary evaporator. After two co-evaporations each with methanol and with toluene, the residue was dried under high vacuum. It was then dissolved in 6 ml of a 1:1 mixture of acetonitrile and sodium bicarbonate solution (5% in water), and 402 μl (1.75 mmol) of di-tert-butyl dicarbonate were added. This solution was stirred at RT overnight and then extracted three times with ethyl acetate. The combined organic phases were dried over sodium sulphate and freed from the volatile components on a rotary evaporator. The residue was purified by preparative HPLC [Method 8]. This gave 351 mg (75% of theory) of the title compound.

LC/MS [Method 3]: $R_t$=1.18 min; m/z=220 (M+H—C$_4$H$_8$—CO$_2$)$^+$ $^1$H NMR (400 MHz, DMSO-d$_6$): δ [ppm]=1.30 (s, 9H), 2.94-3.05 (m, 1H), 3.17-3.31 (m, 2H), 3.54-3.66 (m, 2H), 4.68 (t, 1H), 6.77 (t, 1H), 7.49-7.58 (m, 4H).

Example 18A

3-Amino-2-[3-(trifluoromethyl)phenyl]propylcarbamate hydrochloride

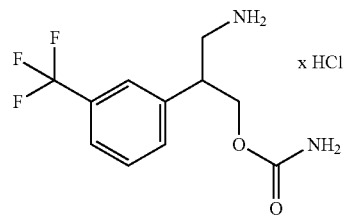 [SMILES: NCC(COC(N)=O)c1cccc(C(F)(F)F)c1]

A solution of 350 mg (1.10 mmol) of the compound of Example 17A in 50 ml of acetonitrile was cooled to −15° C., and a solution of 191 μl (2.19 mmol) of chlorosulphonyl isocyanate in 10 ml of acetonitrile was added dropwise. After 5 min, 50 ml of water were added and the mixture was heated at 60° C. for 4 h. After cooling to RT, 50 ml of a saturated aqueous sodium bicarbonate solution were added and the mixture was extracted three times with ethyl acetate. The combined organic phases were dried over sodium sulphate and freed from the volatile components on a rotary evaporator. 5 ml of a 4 N solution of hydrogen chloride in dioxane were added to the residue, and the mixture was stirred for 5 min Once more, the volatile components were then removed on a rotary evaporator. The residue (385 mg) corresponded to the crude title compound in a purity of about 60% according to LC/MS (about 70% of theory); this material was reacted further without purification.

LC/MS [Method 4]: $R_t$=0.52 min; m/z=263 (M+H)$^+$.

Example 19A

3-[(tert-Butoxycarbonyl)amino]-2-[3-(trifluoromethyl)phenyl]propyl ethylcarbamate

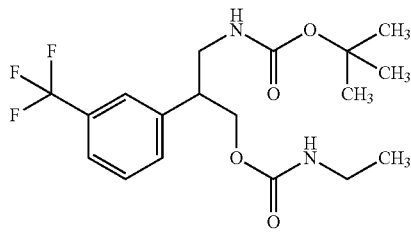 [SMILES: CCNC(=O)OCC(CNC(=O)OC(C)(C)C)c1cccc(C(F)(F)F)c1]

5 mg (42 μmol) of 4-N,N-dimethylaminopyridine and 66 μl (0.84 mmol) of ethyl isocyanate were added to a solution of 134 mg (0.42 mmol) of the compound of Example 17A in 2.5 ml of pyridine. The mixture was stirred at RT overnight. A further 66 μl of ethyl isocyanate were then added, and the mixture was heated at 50° C. for 24 h. After cooling to RT, 0.5 ml of ammonia solution (35% in water) was added. The volatile components were removed on a rotary evaporator. A little acetonitrile and 1 N hydrochloric acid were added to the residue, and the solution was separated by preparative HPLC [Method 9]. This gave 110 mg (67% of theory) of the title compound.

LC/MS [Method 4]: $R_t$=1.15 min; m/z=391 (M+H)$^+$ $^1$H NMR (400 MHz, DMSO-d$_6$): δ [ppm]=0.95 (t, 3H), 1.29 (s, 9H), 2.94 (quin, 2H), 3.17-3.28 (m, 3H), 4.11-4.24 (m, 2H), 6.87 (br. t, 1H), 7.06 (t, 1H), 7.50-7.62 (m, 4H).

Example 20A

3-Amino-2-[3-(trifluoromethyl)phenyl]propyl ethylcarbamate hydrochloride

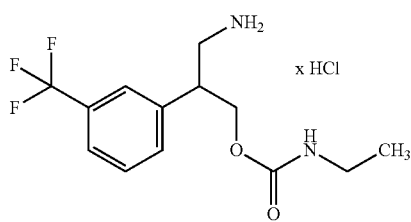 [SMILES: CCNC(=O)OCC(CN)c1cccc(C(F)(F)F)c1]

105 mg (0.27 mmol) of the compound of Example 19A were dissolved in 2 ml of a 4 N solution of hydrogen chloride in dioxane, and the mixture was stirred at 60° C. until the reaction had gone to completion (about 2 h). The volatile components were then removed on a rotary evaporator and the residue was dried under high vacuum. This gave 91 mg of the title compound in a purity of about 83% according to LC/MS (about 86% of theory); this material was reacted further without further purification.

LC/MS [Method 4]: $R_t$=0.65 min; m/z=291 (M+H)$^+$.

Example 21A tert-Butyl [(2,3-dichlorophenyl)(phenylsulphonyl)methyl]carbamate

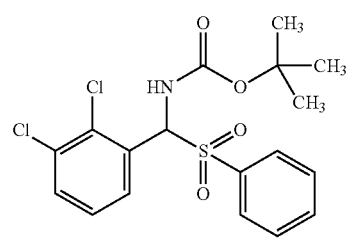 [SMILES: CC(C)(C)OC(=O)NC(c1cccc(Cl)c1Cl)S(=O)(=O)c1ccccc1]

At RT, 2.23 g (19.0 mmol) of tert-butyl carbamate and 6.25 g (38.1 mmol) of benzenesulphinic acid sodium salt were initially charged in 55 ml of methanol/water (1:2), and 5.00 g (28.6 mmol) of 2,3-dichlorobenzaldehyd and then 1.43 ml (37.9 mmol) of formic acid were added. The reaction mixture was stirred at RT for 2 days. The precipitated solid was filtered off with suction and washed with water and twice with diethyl ether. From the ethereal filtrate, 3.47 g of 2,3-dichlorobenzaldehyde were recovered after removal of the solvent on a rotary evaporator. The solid which was filtered off with suction was dried under high vacuum. This gave 2.22 g (19% of theory) of the title compound.

$^1$H NMR (400 MHz, DMSO-d$_6$): δ [ppm]=8.93 (d, 1H), 7.96 (d, 1H), 7.84 (d, 2H), 7.76 (d, 2H), 7.63-7.71 (m, 2H), 7.51 (t, 1H), 6.60 (d, 1H), 1.21 (s, 9H).

Example 22A tert-Butyl [(E)-(2,3-dichlorophenyl)methylidene]carbamate

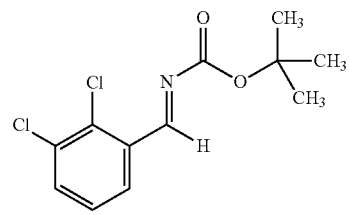 [SMILES: CC(C)(C)OC(=O)/N=C/c1cccc(Cl)c1Cl]

4.42 g (32.0 mmol) of potassium carbonate were dried in the heat under high vacuum and then cooled to RT under an atmosphere of argon. 52 ml of anhydrous THF and 2.22 g (5.33 mmol) of the compound of Example 21A were added. The reaction mixture was then stirred at reflux temperature for 16 h. After cooling to RT, the reaction mixture was filtered through Celite. The solid was washed with a little THF. The combined filtrates were freed from the solvent on a rotary evaporator and the residue was dried under high vacuum. This gave 1.38 g (94% of theory) of the title compound.

MS: m/z=274 (M+H)$^+$ $^1$H NMR (400 MHz, DMSO-d$_6$): δ [ppm]=9.11 (s, 1H), 8.01 (d, 1H), 7.92 (d, 1H), 7.52 (t, 1H), 1.52 (s, 9H).

Example 23A tert-Butyl [1-(2,3-dichlorophenyl)-2-nitroethyl]carbamate

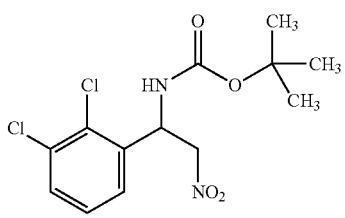 [SMILES: CC(C)(C)OC(=O)NC(C[N+](=O)[O-])c1cccc(Cl)c1Cl]

263 µl (1.51 mmol) of N,N-diisopropylethylamine were added to 10.1 ml (186 mmol) of nitromethane, and the yellow solution was stirred at RT for 1 h. 1.38 g (5.03 mmol) of the compound of Example 22A were then added, and the mixture was stirred at RT overnight. All volatile components were removed on a rotary evaporator. The residue was purified by preparative HPLC [Method 12]. This gave 865 mg (51% of theory) of the title compound.

LC/MS [Method 4]: R$_t$=1.17 min; m/z=333 (M−H)$^−$ $^1$H NMR (400 MHz, DMSO-d$_6$): δ [ppm]=8.07 (d, 1H), 7.64 (d, 1H), 7.50 (d, 1H), 7.44 (t, 1H), 5.74 (t, 1H), 4.87 (d, 1H), 4.62 (t, 1H), 1.34 (s, 9H).

Example 24A tert-Butyl [2-amino-1-(2,3-dichlorophenyl)ethyl]carbamate

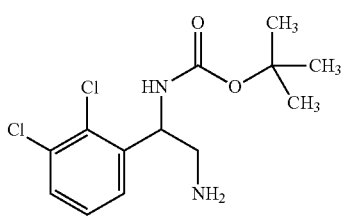 [SMILES: CC(C)(C)OC(=O)NC(CN)c1cccc(Cl)c1Cl]

A solution of 440 mg (1.31 mmol) of the compound of Example 23A in 100 ml of methanol was hydrogenated in a continuous-flow hydrogenation apparatus fitted with a Raney-nickel cartridge (H-Cube from Thales Nano, Budapest, Model HC-2-SS) at a flow rate of 1 ml/min, a temperature of 40° C. and at standard pressure. After the reaction had ended, the solution was freed from the methanol on a rotary evaporator and the residue was dried briefly under high vacuum. This gave 370 mg (91% of theory) of the title compound.

LC/MS [Method 4]: R$_t$=0.76 min; m/z=305 (M+H)$^+$ $^1$H NMR (400 MHz, DMSO-d$_6$): δ [ppm]=7.55 (br. d, 1H), 7.51 (dd, 1H), 7.31-7.39 (m, 2H), 4.81-4.89 (m, 1H), 2.72 (dd, 1H), 2.59 (d, 1H), 1.66 (br. s, 2H), 1.36 (s, 9H).

Example 25A 1-(2-Chlorophenyl)-2-nitroethanamine hydrochloride

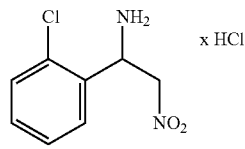

10 ml of a 4 N solution of hydrogen chloride in dioxane were added to a solution of 1.037 g (3.45 mmol) of tert-butyl [1-(2-chlorophenyl)-2-nitroethyl]carbamate [see, for example, *Tetrahedron Lett.* 2009, 50 (9), 1016] in 10 ml of dichloromethane, and the mixture was stirred at RT for 2 h. The volatile components were then removed on a rotary evaporator. 5 ml of dichloromethane were added to the residue, and the mixture was once more freed from the solvent on a rotary evaporator and then dried under high vacuum. This gave 898 mg of the title compound (quant., still contains about 8% dioxane according to $^1$H NMR).

LC/MS [Method 4]: R$_t$=0.34 min; m/z=200 (M+H)$^+$ $^1$H NMR (400 MHz, DMSO-d$_6$): δ [ppm]=5.18 (dd, 1H), 5.31 (dd, 1H), 5.38 (dd, 1H), 7.44-7.53 (m, 2H), 7.56-7.63 (m, 1H), 7.82-7.91 (m, 1H), 9.10 (br. s, 3H).

Example 26A

N-[1-(2-Chlorophenyl)-2-nitroethyl]methanesulphonamide

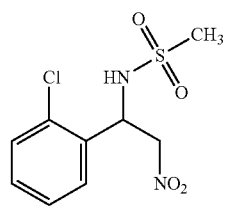 [SMILES: CS(=O)(=O)NC(C[N+](=O)[O-])c1ccccc1Cl]

At RT, 182 µl (2.35 mmol) of methanesulphonyl chloride were added to a solution of 300 mg (about 93% pure, 1.18 mmol) of the compound of Example 25A in 7.2 ml of pyridine, and the mixture was stirred for 1 h. The pyridine was removed on a rotary evaporator and the residue was purified by preparative HPLC [Method 20]. This gave 221 mg (65% of theory) of the title compound.

LC/MS [Method 4]: R$_t$=0.82 min; m/z=279 (M+H)$^+$ $^1$H NMR (400 MHz, DMSO-d$_6$): δ [ppm]=2.68 (s, 3H), 4.68 (dd, 1H), 4.91 (dd, 1H), 5.57 (td, 1H), 7.37-7.48 (m, 2H), 7.52 (dd, 1H), 7.70 (dd, 1H), 8.47 (d, 1H).

Example 27A

N-[2-Amino-1-(2-chlorophenyl)ethyl]methane-sulphonamide

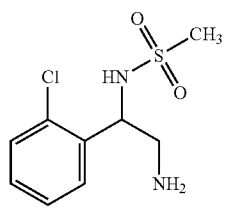

A solution of 221 mg (0.79 mmol) of the compound of Example 26A in 45 ml of methanol was hydrogenated in a continuous-flow hydrogenation apparatus fitted with a Raney-nickel cartridge (H-Cube from Thales Nano, Budapest, Model HC-2-SS) at a flow rate of 1 ml/min, a temperature of 45° C. and at standard pressure. After the reaction had ended, the solution was freed from the methanol on a rotary evaporator and the residue was dried briefly under high vacuum. This gave 186 mg (94% of theory) of the title compound.

LC/MS [Method 4]: $R_t$=0.33 min; m/z=249 (M+H)$^+$ $^1$H NMR (400 MHz, DMSO-$d_6$): δ [ppm]=2.60 (dd, 1H), 2.77 (dd, 1H), 2.81 (s, 3H), 3.50-4.40 (br. s, 3H), 4.69 (dd, 1H), 7.25-7.32 (m, 1H), 7.33-7.44 (m, 2H), 7.54 (dd, 1H).

Example 28A

N-[1-(2-Chlorophenyl)-2-nitroethyl]ethanesulphonamide

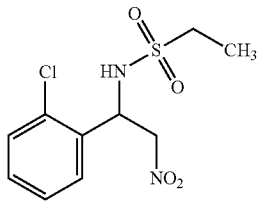 [SMILES: CCS(=O)(=O)NC(C[N+](=O)[O-])c1ccccc1Cl]

At RT, 219 µl (2.31 mmol) of ethanesulphonyl chloride were added to a solution of 295 mg (about 93% pure, 1.16 mmol) of the compound of Example 25A in 7.0 ml of pyridine, and the mixture was stirred for 1 h. The pyridine was then removed on a rotary evaporator and the residue was purified by preparative HPLC [Method 20]. This gave 230 mg (about 90% pure according to LC/MS, 61% of theory) of the title compound.

LC/MS [Method 4]: $R_t$=0.88 min; m/z=293 (M+H)$^+$ $^1$H NMR (400 MHz, DMSO-$d_6$): δ [ppm]=1.02 (t, 3H), 2.68 (dq, 1H), 2.82 (dq, 1H), 4.67 (dd, 1H), 4.89 (dd, 1H), 5.55 (td, 1H), 7.36-7.48 (m, 2H), 7.49-7.53 (m, 1H), 7.69-7.74 (m, 1H), 8.45 (d, 1H).

Example 29A

N-[2-Amino-1-(2-chlorophenyl)ethyl]ethanesulphonamide

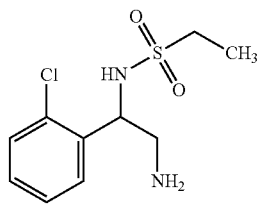 [SMILES: CCS(=O)(=O)NC(CN)c1ccccc1Cl]

Analogously to Example 27A, 230 mg (0.79 mmol) of the compound of Example 28A gave 190 mg (about 90% pure according to LC/MS, 83% of theory) of the title compound.

LC/MS [Method 4]: $R_t$=0.43 min; m/z=263 (M+H)$^+$ $^1$H NMR (400 MHz, DMSO-$d_6$): δ [ppm]=1.11 (t, 3H), 2.62 (dd, 1H), 2.69-2.84 (m, 2H), 2.93 (dq, 1H), about 3.35-4.50 (br. s, 3H), 4.69 (dd, 1H), 7.29 (dt, 1H), 7.33-7.46 (m, 2H), 7.56 (dd, 1H).

Example 30A

1-[1-(2-Chlorophenyl)-2-nitroethyl]urea

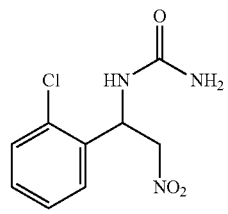 [SMILES: NC(=O)NC(C[N+](=O)[O-])c1ccccc1Cl]

At RT, 300 mg (about 93% pure, 1.18 mmol) of the compound of Example 25A were initially charged in 12 ml of water/methanol (1:1 v/v), and 287 mg (3.53 mmol) of potassium cyanate were added. The reaction mixture was warmed to 40° C. for 1 h. After cooling to RT, the mixture was directly separated into its components by preparative HPLC [Method 8]. This gave 120 mg (41% of theory) of the title compound.

LC/MS [Method 4]: $R_t$=0.67 min; m/z=244 (M+H)$^+$ $^1$H NMR (400 MHz, DMSO-$d_6$): δ [ppm]=4.73 (dd, 1H), 4.88 (dd, 1H), 5.71 (br. s, 2H), 5.77 (dt, 1H), 6.99 (d, 1H), 7.35 (dt, 1H), 7.40 (dt, 1H), 7.48 (dd, 1H), 7.51 (dd, 1H).

Example 31A

1-[2-Amino-1-(2-chlorophenyl)ethyl]urea

Analogously to Example 27A, 120 mg (0.49 mmol) of the compound of Example 30A gave 94 mg (72% of theory) of the title compound.

LC/MS [Method 4]: $R_t$=0.24 min; m/z=214 (M+H)$^+$ $^1$H NMR (400 MHz, DMSO-d$_6$): δ [ppm]=2.64 (dd, 1H), 2.79 (dd, 1H), 3.32 (br. s, 2H), 4.93 (td, 1H), 5.57 (br. s, 2H), 6.70 (d, 1H), 7.21-7.27 (m, 1H), 7.29-7.41 (m, 3H).

Example 32A

Methyl {3-(4-chlorophenyl)-5-oxo-4-[(1E)-3,3,3-trifluoroprop-1-en-1-yl]-4,5-dihydro-1H-1,2,4-triazol-1-yl}acetate

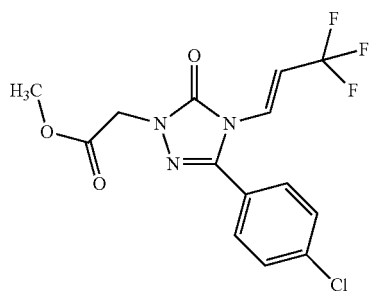 [SMILES: COC(=O)Cn1nc(-c2ccc(Cl)cc2)n(/C=C/C(F)(F)F)c1=O]

At RT, 280 mg (0.74 mmol) of the compound of Example 7A together with 108 mg (0.89 mmol) of 4-N,N-dimethylaminopyridine were initially charged in 5.3 ml of pyridine, 0.31 ml (1.84 mmol) of trifluoromethanesulphonic anhydride were added a little at a time and the mixture was stirred for 12 h. The pyridine was then removed on a rotary evaporator. The residue was taken up in acetonitrile and 1 N hydrochloric acid and purified by preparative HLPC [Method 9]. This gave 230 mg (86% of theory) of the title compound.

LC/MS [Method 4]: $R_t$=1.14 min; m/z=362 (M+H)$^+$ $^1$H NMR (400 MHz, DMSO-d$_6$): δ [ppm]=3.72 (s, 3H), 4.78 (s, 2H), 6.85 (dd, 1H), 7.18 (d, 1H), 7.68 (s, 4H).

Example 33A

{3-(4-Chlorophenyl)-5-oxo-4-[(1E)-3,3,3-trifluoroprop-1-en-1-yl]-4,5-dihydro-1H-1,2,4-triazol-1-yl}acetic acid

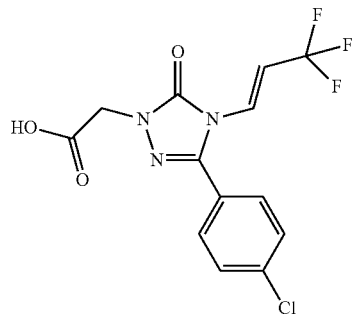 [SMILES: O=C(O)Cn1nc(-c2ccc(Cl)cc2)n(/C=C/C(F)(F)F)c1=O]

260 mg (0.72 mmol) of the compound of Example 32A were dissolved in 5 ml of methanol, and 2.87 ml (2.87 mmol) of a 1 M solution of lithium hydroxide in water were added. The mixture was stirred at RT for 1 h, then acidified with 1 N hydrochloric acid and diluted with DMSO. This solution was then purified directly by preparative HLPC [Method 9]. This gave 215 mg (86% of theory) of the title compound.

LC/MS [Method 4]: $R_t$=1.03 min; m/z=348 (M+H)$^+$ $^1$H NMR (400 MHz, DMSO-d$_6$): δ [ppm]=4.64 (s, 2H), 6.79-6.92 (m, 1H), 7.19 (dd, 1H), 7.68 (s, 4H), 13.31 (br. s, 1H).

Example 34A

2-Amino-2-[3-(trifluoromethyl)phenyl]propanamide

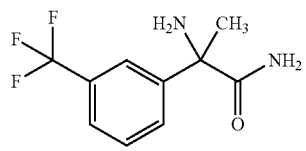 [SMILES: CC(N)(C(N)=O)c1cccc(C(F)(F)F)c1]

138 ml of water, 108 ml of 25% strength aqueous ammonia solution and 173 ml of ethanol were initially charged. 108 g (574 mmol) of 1-[3-(trifluoromethyl)phenyl]ethanone, 30 g (574 mmol) of sodium cyanide and 31 g (631 mmol) of ammonium chloride were added. The mixture was stirred in an autoclave at 70° C. for 20 h. The ethanol was then removed on a rotary evaporator and the residue was extracted four times with in each case 500 ml of diethyl ether. Magnesium sulphate and activated carbon were added to the combined organic phases, and the mixture was filtered off with suction through kieselguhr. The filtrate was concentrated on a rotary evaporator and the residue was purified by chromatography on 2 kg of silica gel 60 (mobile phase: cyclohexane/ethyl acetate 3:1 to 1:1).

With ice cooling, 500 ml of concentrated hydrochloric acid were added slowly to the intermediate 2-amino-2-[3-(trifluoromethyl)phenyl]propionitrile obtained in this manner [56 g, 46% of theory; $^1$H NMR (400 MHz, CDCl$_3$): δ [ppm]=1.78 (s, 3H), 2.14 (br. s, 2H), 7.55 (t, 1H), 7.63 (d, 1H), 7.88 (d, 1H), 7.96 (s, 1H)]. The suspension was stirred at RT overnight. On a rotary evaporator, the volume was then reduced to about 150 ml. 250 ml of acetone were added, and all volatile components were then removed on a rotary evaporator. With ice cooling, 125 ml of concentrated ammonia solution were added to the solid slurry that remained. The mixture was stirred in an ice bath for 30 min. The crystals formed were filtered off with suction, pressed dry and washed twice with in each case 50 ml of ice water and then with pentane. The product was dried under high vacuum. This gave 43 g (32% of theory) of the title compound.

MS (ESIpos): m/z=233 (M+H)$^+$ $^1$H NMR (400 MHz, CDCl$_3$): δ [ppm]=1.82 (s, 3H), 1.85 (br. s, 2H), 5.54 (br. s, 1H), 7.26 (br. s, 1H), 7.48 (t, 1H), 7.55 (d, 2H), 7.75 (d, 1H), 7.83 (s, 1H).

Example 35A

2-[3-(Trifluoromethyl)phenyl]propane-1,2-diamine dihydrochloride

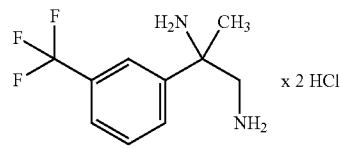

x 2 HCl

A suspension of 500 mg (2.15 mmol) of the compound of Example 34A in 20 ml of diethyl ether was cooled to 0° C., and 3.72 ml of lithium aluminium hydride solution (1 M in diethyl ether, 3.72 mmol) were added slowly. After 15 min, the cooling bath was removed and the reaction mixture was stirred at RT overnight. With ice cooling, 5 ml of a 5% strength aqueous potassium sodium tartrate solution were slowly added dropwise. The mixture was diluted with 40 ml of diethyl ether and 40 ml of 5% strength potassium sodium tartrate solution and then extracted. The aqueous phase was extracted two more times with diethyl ether. The combined organic phases were dried over sodium sulphate, 3 ml of a 4 N solution of hydrogen chloride in dioxane were added and the mixture was then freed from the volatile components on a rotary evaporator. According to LC/MS, the residue (153 mg) contained the title compound in an amount of about 35%, and it was reacted further as such, without further purification.

LC/MS [Method 2]: $R_t$=0.23 min; m/z=219 (M+H)$^+$.

Example 36A tert-Butyl {2-hydroxy-2-[2-(trifluoromethyl)phenyl]ethyl}carbamate

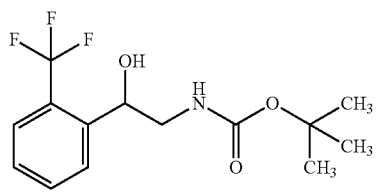 [SMILES: CC(C)(C)OC(=O)NCC(O)c1ccccc1C(F)(F)F]

At RT, 963 µl (4.19 mmol) of di-tert-butyl dicarbonate were added to a solution of 430 mg (2.1 mmol) of 2-hydroxy-2-[(2-trifluoromethyl)phenyl]ethanamine in 20 ml of dichloromethane, and the mixture was stirred for 3 h. The reaction mixture was then diluted with 100 ml of ethyl acetate and washed in each case twice with 1 M hydrochloric acid, saturated sodium bicarbonate solution and saturated sodium chloride solution. The organic phase was dried over sodium sulphate and freed from the solvent on a rotary evaporator. The residue was purified by preparative HPLC [Method 9]. This gave 470 mg (73% of theory) of the title compound.

LC/MS [Method 4]: $R_t$=1.05 min; m/z=306 (M+H)$^+$ $^1$H NMR (400 MHz, DMSO-d$_6$): δ [ppm]=1.31 (s, 9H), 3.04-3.18 (m, 2H), 4.64-4.73 (m, 1H), 5.59 (d, 1H), 6.79 (t, 1H), 7.52-7.65 (m, 4H).

Example 37A

2-Amino-1-[2-(trifluoromethyl)phenyl]ethyl carbamate

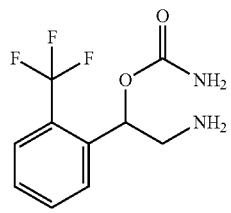 [SMILES: NCC(OC(N)=O)c1ccccc1C(F)(F)F]

A solution of 420 mg (1.38 mmol) of the compound of Example 36A in 100 ml of acetonitrile was cooled to −15° C., and a solution of 168 µl (1.93 mmol) of chlorosulphonyl isocyanate in 10 ml of acetonitrile was added dropwise. After 5 min, 50 ml of water were added and the reaction mixture was stirred further at 60° C. overnight. After cooling to RT, 50 ml of a saturated aqueous sodium bicarbonate solution were added. The mixture was extracted three times with ethyl acetate. The combined organic phases were dried over sodium sulphate and freed from the solvent on a rotary evaporator. The residue (321 mg, about 90% pure, 85% of theory) corresponded to the title compound and was reacted further without additional purification.

LC/MS [Method 4]: $R_t$=0.49 min; m/z=249 (M+H)$^+$.

Example 38A tert-Butyl {2-hydroxy-2-[3-(trifluoromethyl)phenyl]ethyl}carbamate

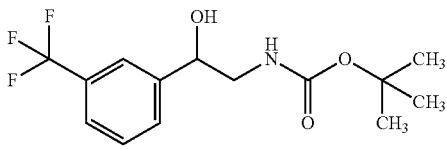 [SMILES: CC(C)(C)OC(=O)NCC(O)c1cccc(C(F)(F)F)c1]

At RT, 3.2 ml of a 5% strength aqueous sodium bicarbonate solution and 91 mg (0.41 mmol) of di-tert-butyl dicarbonate were added to a solution of 85 mg (0.41 mmol) of 2-hydroxy-2-[(3-trifluoromethyl)phenyl]ethanamine [for the preparation see *J. Med. Chem.* 1968, 11, 1258-1262] in 3.2 ml of dioxane, and the mixture was stirred until the reaction had gone to completion. The reaction mixture was then extracted three times with ethyl acetate. The combined organic phases were dried over sodium sulphate and freed from the solvent on a rotary evaporator. The residue (88 mg, 70% of theory) corresponded to the title compound.

LC/MS [Method 4]: $R_t$=1.03 min; m/z=304 (M−H)$^−$ $^1$H NMR (400 MHz, DMSO-d$_6$): δ [ppm]=1.31 (s, 9H), 3.04-3.19 (m, 2H), 4.61-4.74 (m, 1H), 5.59 (d, 1H), 6.79 (t, 1H), 7.50-7.67 (m, 4H).

Example 39A

2-Amino-1-[3-(trifluoromethyl)phenyl]ethyl carbamate hydrochloride

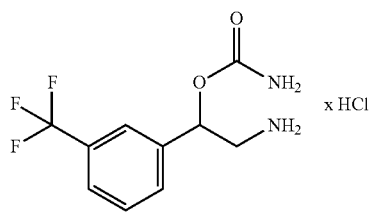 [SMILES: NCC(OC(N)=O)c1cccc(C(F)(F)F)c1]

Analogously to Example 37A, 85 mg (0.28 mmol) of the compound of Example 38A were reacted. The 2-amino-1-[3-(trifluoromethyl)phenyl]ethyl carbamate obtained in this manner was stirred for 5 min with 2 ml of a 4 N solution of hydrogen chloride in dioxane. The volatile components were removed on a rotary evaporator and the residue was dried under high vacuum. This gave 73 mg (85% of theory) of the title compound.

LC/MS [Method 2]: $R_t$=1.08 min; m/z=249 (M+H)$^+$
$^1$H NMR (400 MHz, DMSO-d$_6$): δ [ppm]=3.16-3.29 (m, 2H), 5.82 (dd, 1H), 6.79 (br. s, 2H), 7.63-7.78 (m, 4H), 8.18 (br. s, 3H).

Example 40A

2-Amino-1-(2-chlorophenyl)ethyl carbamate

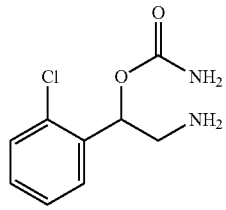 [SMILES: NCC(OC(N)=O)c1ccccc1Cl]

Analogously to Example 37A, 114 mg (0.42 mmol) of tert-butyl [2-(2-chlorophenyl)-2-hydroxy-ethyl]carbamate gave 46 mg (51% of theory) of the title compound.

LC/MS [Method 2]: $R_t$=0.88 min; m/z=215 (M+H)$^+$
$^1$H NMR (400 MHz, DMSO-d$_6$): δ [ppm]=2.73 (dd, 1H), 2.86 (dd, 1H), 5.71 (dd, 1H), 6.65 (br. s, 2H), 7.28-7.33 (m, 1H), 7.34-7.41 (m, 2H), 7.43 (dd, 1H).

Example 41A

2-Amino-1-(2,3-dichlorophenyl)ethanone hydrochloride

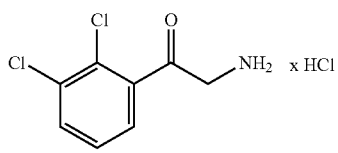 [SMILES: NCC(=O)c1cccc(Cl)c1Cl]

At RT, 411 mg (4.33 mmol) of sodium diformylamide were added to 1.0 g (3.73 mmol) of 2-bromo-1-(2,3-dichlorophenyl)ethanone [for the preparation, see for example U.S. Pat. No. 5,831,132] in 4 ml of acetonitrile, and the mixture was stirred at RT overnight. The mixture was then heated to 70° C. and filtered whilst still warm. The solid that remained was washed with 2 ml of hot acetonitrile. The combined filtrates were freed from the solvent on a rotary evaporator. 10 ml of a 5% strength ethanolic hydrogen chloride solution were added to the dark-brown oily residue, and the mixture was stirred at RT overnight. The volatile components were removed on a rotary evaporator and the yellow solid that remained was stirred in 20 ml of boiling diethyl ether. After cooling to RT, the solid was isolated by filtration, washed with diethyl ether and dried under high vacuum. This gave 410 mg (46% of theory) of the title compound.

LC/MS [Method 21]: $R_t$=0.78 min; m/z=204 (M+H)$^+$
$^1$H NMR (400 MHz, DMSO-d$_6$): δ [ppm]=4.51 (br. s, 2H), 7.57 (t, 1H), 7.88 (dd, 1H), 7.92 (dd, 1H), 8.52 (br. s, 3H).

Example 42A

2-Amino-1-(2,3-dichlorophenyl)ethanol

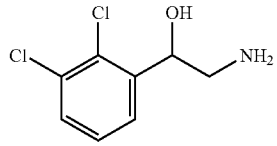 [SMILES: NCC(O)c1cccc(Cl)c1Cl]

Under argon, 300 mg (1.25 mmol) of the compound of Example 41A were initially charged in 2 ml of methanol. 189 mg (5.0 mmol) of sodium borohydride were added and the mixture was stirred overnight. 1 N hydrochloric acid was added slowly until the evolution of gas had ceased, and the methanol was then removed on a rotary evaporator. The aqueous residue was made alkaline by addition of sodium bicarbonate solution and extracted three times with ethyl acetate. The combined organic phases were dried over sodium sulphate and freed from the solvent on a rotary evaporator. The residue (189 mg, 74% of theory) corresponded to the title compound.

LC/MS [Method 4]: $R_t$=0.48 min; m/z=206 (M+H)$^+$
$^1$H NMR (400 MHz, DMSO-d$_6$): δ [ppm]=1.60-1.99 (br. s, 2H), 2.45-2.52 (dd, 1H), 2.77 (dd, 1H), 4.83 (dd, 1H), 5.62 (br. s, 1H), 7.34-7.40 (m, 1H), 7.53 (d, 2H).

Example 43A tert-Butyl [2-(2,3-dichlorophenyl)-2-hydroxyethyl]carbamate

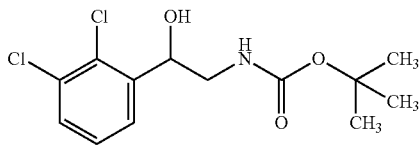 [SMILES: CC(C)(C)OC(=O)NCC(O)c1cccc(Cl)c1Cl]

At RT, 281 μl (1.22 mmol) of di-tert-butyl dicarbonate were added to a solution of 126 mg (0.61 mmol) of the compound of Example 42A in 5 ml of acetonitrile and 5 ml of dichloromethane, and the mixture was stirred overnight. The volatile components were removed on a rotary evaporator and the residue was purified by preparative HPLC [Method 9]. This gave 117 mg (62% of theory) of the title compound.

LC/MS [Method 4]: $R_t$=1.05 min; m/z=306 (M+H)$^+$ $^1$H NMR (400 MHz, DMSO-$d_6$): δ [ppm]=1.33 (s, 9H), 3.03-3.21 (m, 2H), 4.97-5.05 (m, 1H), 5.65 (d, 1H), 6.80 (t, 1H), 7.37 (t, 1H), 7.52 (d, 2H).

Example 44A

2-Amino-1-(2,3-dichlorophenyl)ethyl carbamate

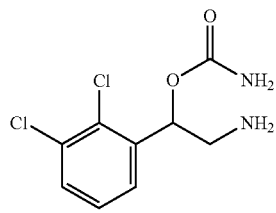 [SMILES: NCC(OC(N)=O)c1cccc(Cl)c1Cl]

Analogously to Example 37A, 117 mg (0.38 mmol) of the compound of Example 43A gave 62 mg (63% of theory) of the title compound.

LC/MS [Method 4]: $R_t$=0.52 min; m/z=263 (M+H)$^+$ $^1$H NMR (400 MHz, DMSO-$d_6$): δ [ppm]=1.57 (br. s, 2H), 2.72 (dd, 1H), 2.85 (dd, 1H), 5.69 (dd, 1H), 6.44-6.97 (2 br. s, 2H), 7.35 (dd, 1H), 7.40 (t, 1H), 7.58 (dd, 1H).

Example 45A (2R)-2-Amino-3-[3-(trifluoromethyl)phenyl]propan-1-ol hydrochloride

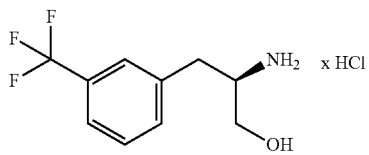 [SMILES: N[C@@H](CO)Cc1cccc(C(F)(F)F)c1]

At 0° C., 4.29 ml of lithium aluminium hydride solution (1 M in diethyl ether, 4.29 mmol) were added slowly to a suspension of 500 mg (2.14 mmol) of (2R)-2-amino-3-[(3-trifluoromethyl)-phenyl]propanecarboxylic acid in 20 ml of diethyl ether. The reaction mixture was stirred at 0° C. for 15 min and then heated under reflux overnight. After cooling to 0° C., 5 ml of a 5% strength aqueous sodium aluminium tartrate solution were added dropwise. The mixture was diluted with 40 ml of diethyl ether and 40 ml of 5% strength sodium aluminium tartrate solution and then extracted. The aqueous phase was extracted two more times with diethyl ether. The combined organic phases were dried over sodium sulphate, 3 ml of a 4 N solution of hydrogen chloride in dioxane were added and the mixture was freed from the volatile components on a rotary evaporator. The residue was dried under high vacuum. This gave 410 mg (67% of theory, about 90% pure according to LC/MS) of the title compound.

LC/MS [Method 1]: $R_t$=0.59 min; m/z=220 (M+H)$^+$ $^1$H NMR (400 MHz, DMSO-$d_6$): δ [ppm]=2.91-3.08 (m, 2H), 3.30-3.45 (m, 2H), 3.48-3.58 (m, 1H), 5.40 (br. s, 1H), 7.51-7.65 (m, 3H), 7.67 (s, 1H), 8.16 (br. m, 3H).

Example 46A (2S)-2-Amino-3-[3-(trifluoromethyl)phenyl]propan-1-ol hydrochloride

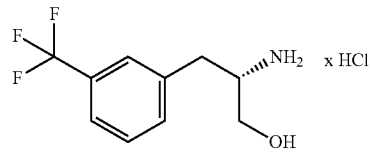 [SMILES: N[C@H](CO)Cc1cccc(C(F)(F)F)c1]

Analogously to Example 45A, 500 mg of (2S)-2-amino-3-[(3-trifluoromethyl)phenyl]propane-carboxylic acid were reacted. This gave 517 mg (89% of theory) of the title compound.

LC/MS [Method 1]: $R_t$=0.59 min; m/z=220 (M+H)$^+$ $^1$H NMR (400 MHz, DMSO-$d_6$): δ [ppm]=2.91-3.06 (m, 2H), 3.34-3.43 (m, 2H), 3.49-3.58 (m, 1H), 5.37 (br. s, 1H), 7.51-7.65 (m, 3H), 7.67 (s, 1H), 8.07-8.24 (br. m, 3H).

Example 47A (2R)-2-Amino-3-[3-(trifluoromethyl)phenyl]propyl carbamate hydrochloride

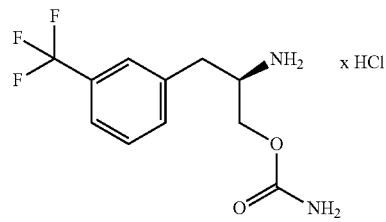 [SMILES: NC(=O)OC[C@H](N)Cc1cccc(C(F)(F)F)c1]

At −15° C., 38 μl (0.44 mmol) of chlorosulphonyl isocyanate were added slowly to a solution of 100 mg (0.31 mmol) of (2R)-tert-butyl {1-hydroxy-3-[3-(trifluoromethyl)phenyl]propan-2-yl}carbamate (for the preparation see US patent application 2008/0242694, Example [0440]) in 2 ml of acetonitrile. The reaction mixture was stirred at RT for 1 h, 3 ml of water were then added and the mixture was heated under reflux overnight. After cooling to RT, the mixture was purified directly by preparative HPLC [Method 9]. This gave a first fraction (21 mg) of the title compound (in part as formate salt) and a fraction (17 mg) of the corresponding compound which was still Boc-protected. The latter fraction was stirred for 30 min with 3 ml of a 4 N solution of hydrogen chloride in dioxane and then freed from the volatile components on a rotary evaporator and then under high vacuum. The residue (16 mg) corresponded to the pure title compound. Both fractions of the title compound were combined and used to prepare subsequent compounds.

LC/MS [Method 1]: $R_t$=0.76 min; m/z=263 (M+H)$^+$ $^1$H NMR (400 MHz, DMSO-d$_6$): δ [ppm]=2.91-3.11 (m, 2H), 3.63-3.75 (m, 1H), 3.90 (dd, 1H), 4.05 (dd, 1H), 6.64 (br. s, 2H), 7.55-7.70 (m, 4H), 8.19 (br. s, 3H).

Example 48A (2S)-2-Amino-3-[3-(trifluoromethyl)phenyl]propyl carbamate hydrochloride

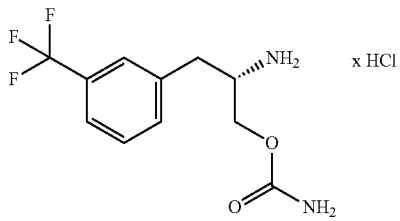 [SMILES: NC(=O)OC[C@@H](N)Cc1cccc(C(F)(F)F)c1]

At −15° C., 51 µl (0.70 mmol) of chlorosulphonyl isocyanate were added slowly to a solution of 160 mg (0.50 mmol) of (2S)-tert-butyl {1-hydroxy-3-[3-(trifluoromethyl)phenyl]propan-2-yl}carbamate (for the preparation see US patent application 2008/0242694, Example [0464]) in 7.6 ml of acetonitrile. The reaction mixture was stirred at RT for 1 h, 1 ml of water was then added and the mixture was heated at 60° C. overnight. An analytical sample showed complete conversion into the target product according to LC/MS. After cooling to RT, the volatile components were removed on a rotary evaporator and finally under high vacuum. The residue (80 mg, 53% of theory) corresponded to the title compound.

LC/MS [Method 3]: R$_t$=0.67 min; m/z=263 (M+H)$^+$.

Example 49A

2-[(5-Chloro-2-thienyl)carbonyl]-N-(2-methoxyethyl)hydrazinecarboxamide

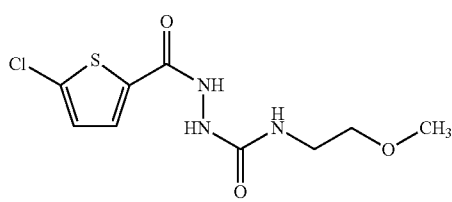 [SMILES: COCCNC(=O)NNC(=O)c1ccc(Cl)s1]

At 50° C., 3.1 g (17.55 mmol) of 5-chlorothiophene-2-carbohydrazide were substantially suspended in 30 ml of dry THF. 1.81 g (17.90 mmol) of 1-isocyanato-2-methoxyethane dissolved in 30 ml of THF were then added dropwise. The mixture was stirred at 50° C. for 2.5 h. After cooling to RT, the solvent was removed on a rotary evaporator and the residue was triturated with diethyl ether. The crystals were filtered off with suction, washed with diethyl ether and dried under high vacuum. This gave 4.87 g (100% of theory) of the title compound.

$^1$H NMR (400 MHz, DMSO-d$_6$): δ=3.14-3.21 (m, 2H), 3.28-3.36 (m, 5H), 6.52 (br. s, 1H), 7.22 (d, 1H), 7.70 (d, 1H), 7.97 (s, 1H), 10.24 (s, 1H).

Example 50A 5-(5-Chloro-2-thienyl)-4-(2-methoxyethyl)-2,4-dihydro-3H-1,2,4-triazol-3-one

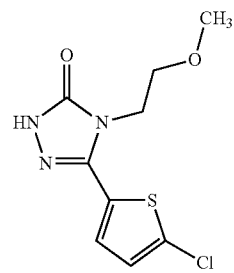 [SMILES: COCCn1c(-c2ccc(Cl)s2)n[nH]c1=O]

4.85 g (17.46 mmol) of the compound of Example 49A were dissolved in 17 ml (52.39 mmol) of 3 M aqueous sodium hydroxide solution and heated under reflux for 168 h. After 16, 40, 64 and 88 h, in each case a further 1.05 g (26.19 mmol, 104.76 mmol in total) of solid sodium hydroxide were added. Using 1M hydrochloric acid, the reaction was adjusted to pH 10, and the mixture was extracted twice with in each case 30 ml of ethyl acetate. The combined organic phases were dried over sodium sulphate, filtered and freed from the solvent on a rotary evaporator. The residue was dried under high vacuum. This gave 2.44 g (54% of theory) of the title compound.

$^1$H NMR (400 MHz, DMSO-d$_6$): δ=3.20 (s, 3H), 3.53 (t, 2H), 3.92 (t, 2H), 7.24 (d, 1H), 7.51 (d, 1H), 12.04 (s, 1H).

Example 51A

Ethyl [3-(5-chloro-2-thienyl)-4-(2-methoxyethyl)-5-oxo-4,5-dihydro-1H-1,2,4-triazol-1-yl]acetate

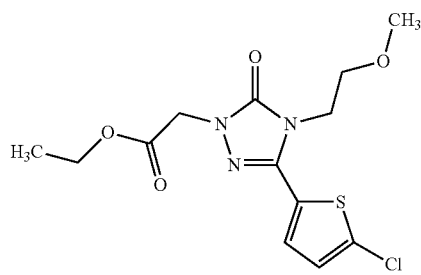 [SMILES: CCOC(=O)Cn1nc(-c2ccc(Cl)s2)n(CCOC)c1=O]

2.4 g (9.24 mmol) of the compound of Example 50A and 2.55 g (18.48 mmol) of potassium carbonate were suspended in 48 ml of acetonitrile. 1.08 ml (10.17 mmol) of ethyl chloroacetate were then added, and the mixture was heated under reflux at 80° C. for 4.5 h. Another 113 mg (0.92 mmol) of ethyl chloroacetate were then added, and the mixture was stirred at 80° C. for a further 2 h. The suspension was then filtered through a layer of silica gel and washed with ethyl acetate, the filtrate was evaporated on a rotary evaporator and the residue was dried under high vacuum. This gave 3.24 g (100% of theory) of the title compound.

LC/MS [Method 22]: R$_t$=2.42 min; m/z=346 (M+H)$^+$

¹H NMR (400 MHz, DMSO-d₆): δ=1.21 (t, 3H), 3.30 (s, 3H), 3.55 (t, 2H), 3.99 (t, 2H), 4.15 (q, 2H), 4.65 (s, 2H), 7.27 (d, 1H), 7.58 (d, 1H).

Example 52A

[3-(5-Chloro-2-thienyl)-4-(2-methoxyethyl)-5-oxo-4,5-dihydro-1H-1,2,4-triazol-1-yl]acetic acid

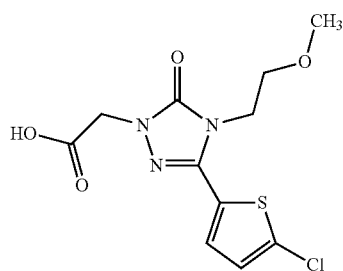 [SMILES: COCCn1c(-c2ccc(Cl)s2)nn(CC(=O)O)c1=O]

3.2 g (9.25 mmol) of the compound of Example 51A were dissolved in 28 ml of methanol. 2.82 ml of a 20% strength aqueous potassium hydroxide solution were then added. The mixture was stirred at RT for 2 h. On a rotary evaporator, the proportion of methanol was reduced by half. The mixture was then diluted with water and extracted once with 15 ml of ethyl acetate. The aqueous phase was acidified with 920 μl of concentrated hydrochloric acid and extracted twice with in each case 15 ml of ethyl acetate. The combined organic phases were dried over sodium sulphate, filtered and freed from the solvent on a rotary evaporator. Drying the residue under high vacuum gave 2.34 g (80% of theory) of the title compound.

LC/MS [Method 22]: R_f=2.05 min; m/z=318 (M+H)⁺

¹H NMR (400 MHz, DMSO-d₆): δ=3.20 (s, 3H), 3.55 (t, 2H), 3.99 (t, 2H), 4.53 (s, 2H), 7.27 (d, 1H), 7.58 (d, 1H), 13.14 (br. s, 1H).

Example 53A

N-{2-Amino-2-[3-(trifluoromethyl)phenyl]propyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydroformate (Diastereomer Mixture)

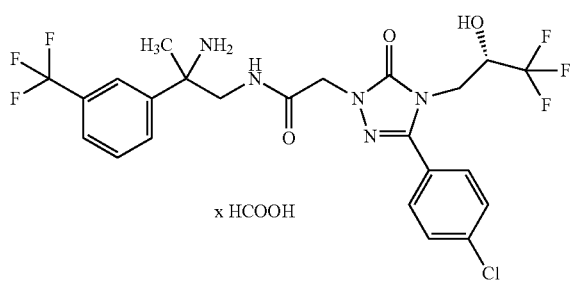 [SMILES: CC(N)(CNC(=O)Cn1nc(-c2ccc(Cl)cc2)n(C[C@H](O)C(F)(F)F)c1=O)c1cccc(C(F)(F)F)c1]

A mixture of 166 mg (0.45 mmol) of the compound of Example 8A, 131 mg (0.68 mmol) of EDC and 92 mg (0.68 mmol) of HOBt in 4 ml of DMF was initially stirred at RT for 10 min and then added dropwise to a solution of 152 mg of the compound of Example 35A (purity about 35%) and 158 μl (0.91 mmol) of N,N-diisopropylethylamine in 2 ml of DMF. The reaction mixture was stirred at RT for 5 min, 2 ml of 1 N hydrochloric acid were then added and the mixture was separated directly by preparative HPLC [Method 9]. This gave 84 mg (30% of theory) of the pure title compound.

LC/MS [Method 4]: R_f=0.88 min; m/z=566 (M+H)⁺

¹H NMR (400 MHz, DMSO-d₆): δ [ppm]=1.39 (s, 3H), 3.35-3.50 (m, 2H), 3.82 (dd, 1H), 3.92-4.00 (m, 1H), 4.28 (br. s, 1H), 4.35-4.49 (m, 2H), 7.51-7.67 (m, 4H), 7.74 (d, 2H), 7.79 (d, 1H), 7.90 (s, 1H), 8.08 (t, 1H), 8.18 (s, 1H).

Example 54A

N-[2-Amino-2-(2,3-dichlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (Diastereomer 1)

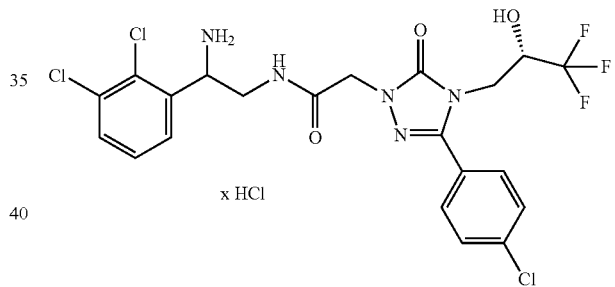

5 ml of a 4 N solution of hydrogen chloride in dioxane were added to a solution of 147 mg (0.23 mmol) of the compound of Example 19 in 5 ml of dichloromethane, and the mixture was stirred at RT for 2 h. The volatile components were then removed on a rotary evaporator. Another 5 ml of dichloromethane were added to the residue, and the mixture was once more freed from the solvent on a rotary evaporator and then purified by preparative HPLC [Method 8]. 10 ml of 1 M hydrochloric acid were added to the product-containing fraction and the mixture was then freed from all volatile components on a rotary evaporator. The residue was dried under high vacuum. This gave 127 mg (96% of theory) of the title compound.

LC/MS [Method 4]: R_f=0.85 min; m/z=552 (M+H)⁺

¹H NMR (400 MHz, DMSO-d₆): δ [ppm]=3.47-3.59 (m, 1H), 3.60-3.71 (m, 1H), 3.83 (dd, 1H), 3.97 (dd, 1H), 4.22-4.35 (m, 1H), 4.37-4.50 (m [AB], 2H), 4.80-4.91 (m, 1H), 6.92 (br. d, 1H), 7.51 (t, 1H), 7.64 (d, 2H), 7.67-7.80 (m, 4H), 8.45 (t, 1H), 8.67 (br. s, 3H).

Example 55A

N-[2-Amino-2-(2,3-dichlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (Diastereomer 2)

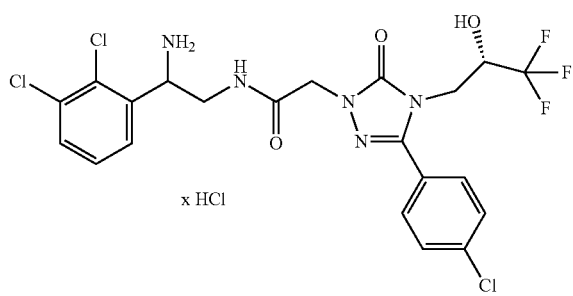 [SMILES: NC(CNC(=O)Cn1nc(-c2ccc(Cl)cc2)n(C[C@H](O)C(F)(F)F)c1=O)c1cccc(Cl)c1Cl]

Analogously to Example 54A, 147 mg (0.23 mmol) of the compound of Example 20 gave 115 mg (87% of theory) of the title compound.

$^1$H NMR (400 MHz, DMSO-d$_6$): δ [ppm]=3.51 (dt, 1H), 3.68 (dt, 1H), 3.83 (dd, 1H), 3.96 (dd, 1H), 4.22-4.34 (m, 1H), 4.43 (s, 2H), 4.81-4.91 (m, 1H), 6.93 (br. d, 1H), 7.51 (t, 1H), 7.64 (d, 2H), 7.70-7.76 (m, 4H), 8.44 (t, 1H), 8.69 (br. s, 3H).

Example 56A

N-{2-Amino-2-[2-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (Diastereomer 1)

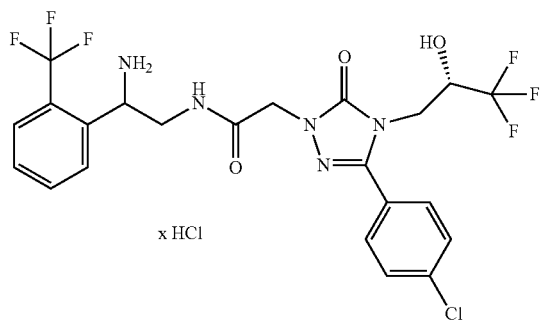 [SMILES: NC(CNC(=O)Cn1nc(-c2ccc(Cl)cc2)n(C[C@H](O)C(F)(F)F)c1=O)c1ccccc1C(F)(F)F]

5 ml of a 4 N solution of hydrogen chloride in dioxane were added to a solution of 145 mg (0.22 mmol) of the compound of Example 14 in 5 ml of dichloromethane, and the mixture was stirred at RT for 2 h. The volatile components were then removed on a rotary evaporator. Another 5 ml of dichloromethane were added to the residue, and once more the mixture was freed from the solvent on a rotary evaporator and then dried under high vacuum. This gave 130 mg (91% of theory) of the title compound (which still contained about 7% dioxane according to $^1$H NMR).

LC/MS [Method 3]: R$_t$=0.97 min; m/z=552 (M+H)$^+$ $^1$H NMR (400 MHz, DMSO-d$_6$): δ [ppm]=3.44-3.55 (m, 1H), 3.64-3.75 (m, 1H), 3.84 (dd, 1H), 3.97 (dd, 1H), 4.21-4.35 (m, 1H), 4.39-4.52 (m [AB], 2H), 4.54-4.67 (m, 1H), 6.91 (d, 1H), 7.61-7.68 (m, 3H), 7.72-7.78 (m, 2H), 7.79-7.88 (m, 2H), 8.00 (d, 1H), 8.50 (t, 1H), 8.76 (br. s, 3H).

Example 57A

N-{2-Amino-2-[2-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (Diastereomer 2)

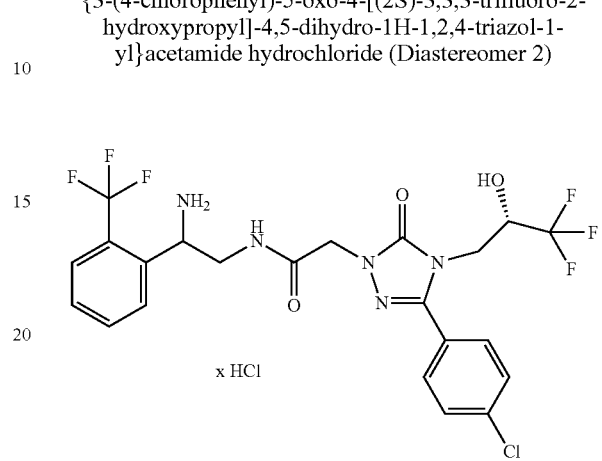

Analogously to Example 56A, 117 mg (0.18 mmol) of the compound of Example 15 gave 104 mg (93% of theory) of the title compound (which still contained about 5% dioxane according to $^1$H NMR).

LC/MS [Method 3]: R$_t$=0.97 min; m/z=552 (M+H)$^+$ $^1$H NMR (400 MHz, DMSO-d$_6$): δ [ppm]=3.44-3.54 (m, 1H), 3.64-3.74 (m, 1H), 3.83 (dd, 1H), 3.96 (dd, 1H), 4.22-4.34 (m, 1H), 4.39-4.50 (m [AB], 2H), 4.54-4.67 (m, 1H), 6.93 (d, 1H), 7.61-7.69 (m, 3H), 7.74 (d, 2H), 7.78-7.90 (m, 2H), 8.01 (d, 1H), 8.50 (t, 1H), 8.79 (br. s, 3H).

Example 58A

N-{2-Amino-2-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (Diastereomer Mixture)

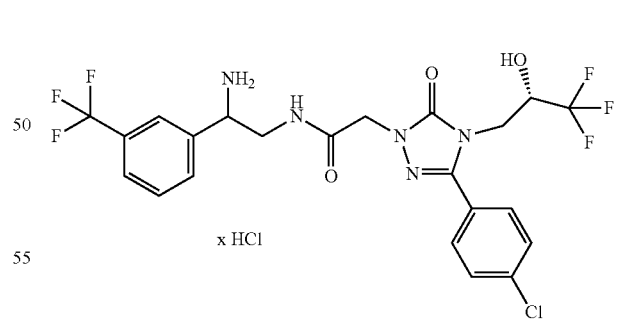

Analogously to Example 56A, 235 mg (0.36 mmol) of the compound of Example 34 gave 220 mg (99% of theory) of the title compound (which still contained about 5% dioxane according to $^1$H NMR).

LC/MS [Method 4]: R$_t$=0.87 min; m/z=552 (M+H)$^+$ $^1$H NMR (400 MHz, DMSO-d$_6$): δ [ppm]=3.50-3.61 (m, 1H), 3.62-3.73 (m, 1H), 3.83 (dd, 1H), 3.97 (br. d, 1H), 4.22-4.35 (m, 1H), 4.36-4.49 (m, 2H), 4.54 (br. t, 1H), 6.93

(dd, 1H), 7.61-7.71 (m, 3H), 7.72-7.82 (m, 4H), 7.93 (s, 1H), 8.42 (br. t, 1H), 8.60 (br. s, 3H).

Example 59A

N-{2-Amino-2-[2-(trifluoromethyl)phenyl]ethyl}-2-[3-(4-chlorophenyl)-4-cyclopropyl-5-oxo-4,5-dihydro-1H-1,2,4-triazol-1-yl]acetamide hydrochloride (Racemate)

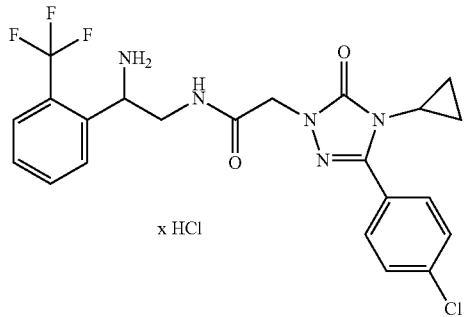 [SMILES: NC(CNC(=O)Cn1nc(-c2ccc(Cl)cc2)n(C2CC2)c1=O)c1ccccc1C(F)(F)F]

x HCl

Analogously to Example 56A, 44 mg (62 µmol) of the compound of Example 65 gave 40 mg (99% of theory) of the title compound (which still contained about 22% dioxane according to $^1$H NMR).

LC/MS [Method 4]: $R_t$=0.72 min; m/z=480 (M+H)$^+$ $^1$H NMR (400 MHz, DMSO-d$_6$): δ [ppm]=0.51-0.62 (m, 2H), 0.86-0.95 (m, 2H), 3.18 (tt, 1H), 3.42-3.53 (m, 1H), 3.62-3.74 (m, 1H), 4.39 (s, 2H), 4.55-4.62 (m, 1H), 7.57-7.69 (m, 3H), 7.75-7.89 (m, 4H), 7.98 (d, 1H), 8.44 (t, 1H), 8.72 (br. s, 3H).

Example 60A

N-{2-Amino-2-[2-(trifluoromethyl)phenyl]ethyl}-2-[3-(5-chloro-2-thienyl)-4-(2-methoxyethyl)-5-oxo-4,5-dihydro-1H-1,2,4-triazol-1-yl]acetamide hydrochloride (Racemate)

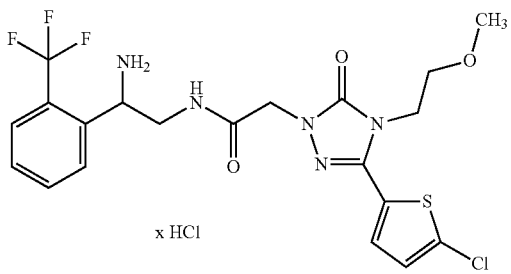 [SMILES: COCCn1c(-c2ccc(Cl)s2)nn(CC(=O)NCC(N)c2ccccc2C(F)(F)F)c1=O]

x HCl

Analogously to Example 56A, 44 mg (60 µmol) of the compound of Example 66 gave 40 mg (99% of theory) of the title compound (which still contained about 20% dioxane according to $^1$H NMR).

LC/MS [Method 4]: $R_t$=0.72 min; m/z=504 (M+H)$^+$ $^1$H NMR (400 MHz, DMSO-d$_6$): δ [ppm]=3.21 (s, 3H), 3.44-3.52 (m, 1H), 3.52-3.59 (m, 2H), 3.64-3.74 (m, 1H), 3.98 (t, 2H), 4.43 (s, 2H), 4.56-4.62 (m, 1H), 7.28 (d, 1H), 7.57 (d, 1H), 7.62-7.69 (m, 1H), 7.81-7.88 (m, 2H), 8.00 (d, 1H), 8.50 (t, 1H), 8.76 (br. s, 3H).

Example 61A

N-{2-Amino-2-[2-(trifluoromethyl)phenyl]ethyl}-2-[3-(5-chloro-2-thienyl)-4-(2-fluorobenzyl)-5-oxo-4,5-dihydro-1H-1,2,4-triazol-1-yl]acetamide hydrochloride (Racemate)

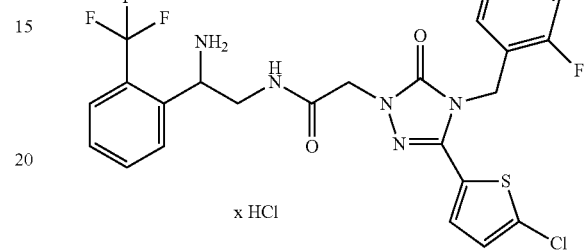

x HCl

Analogously to Example 56A, 49 mg (60 µmol) of the compound of Example 67 gave 47 mg (99% of theory) of the title compound (which still contained about 30% dioxane according to $^1$H NMR).

LC/MS [Method 4]: $R_t$=0.83 min; m/z=554 (M+H)$^+$ $^1$H NMR (400 MHz, DMSO-d$_6$): δ [ppm]=3.44-3.54 (m, 1H), 3.64-3.76 (m, 1H), 4.50 (s, 2H), 4.55-4.64 (m, 1H), 5.15 (s, 2H), 7.07 (t, 1H), 7.12-7.28 (m, 4H), 7.37 (q, 1H), 7.66 (t, 1H), 7.80-7.89 (m, 2H), 8.00 (d, 1H), 8.55 (t, 1H), 8.75 (br. s, 3H).

Working Examples

Example 1

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[2-(trifluoromethyl)phenyl]propyl carbamate (Diastereomer Mixture)

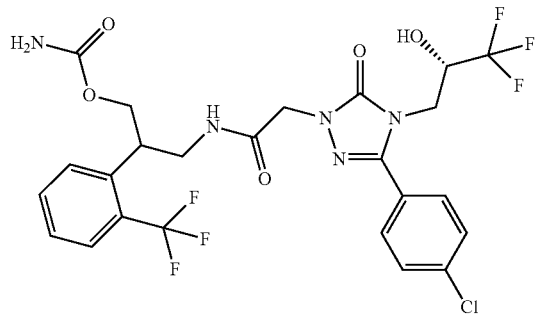 [SMILES: NC(=O)OCC(CNC(=O)Cn1nc(-c2ccc(Cl)cc2)n(C[C@H](O)C(F)(F)F)c1=O)c1ccccc1C(F)(F)F]

A mixture of 366 mg (1.00 mmol) of the compound of Example 8A, 299 mg (1.00 mmol) of the compound of Example 13A, 288 mg (1.50 mmol) of EDC, 203 mg (1.50 mmol) of HOBt and 348 µl (2.0 mmol) of N,N-diisopropylethylamine in 25 ml of DMF was stirred at RT overnight. 1 ml of 1 M hydrochloric acid was then added, and the mixture was separated directly into its components by preparative HPLC

[Method 8]. The product fraction was freed from the solvent on a rotary evaporator and the residue was dried under high vacuum. This gave 340 mg (56% of theory) of the title compound as a diastereomer mixture.

LC/MS [Method 4]: $R_t$=1.04 min; MS [ESIpos]: m/z=610 $(M+H)^+$.

By preparative HPLC on a chiral phase [Method 10a], it was possible to separate the two diastereomers, see Example 2 and Example 3.

Example 2

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[2-(trifluoromethyl)phenyl]propyl carbamate (Diastereomer 1)

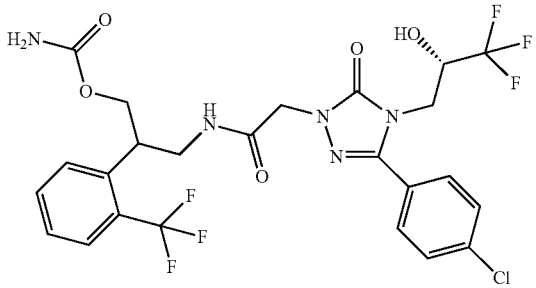 [SMILES: NC(=O)OCC(CNC(=O)Cn1nc(-c2ccc(Cl)cc2)n(C[C@H](O)C(F)(F)F)c1=O)c1ccccc1C(F)(F)F]

First-eluting diastereomer from the chromatographic separation of 340 mg of the compound of Example 1 according to Method 10a. The material obtained in this manner (170 mg) was once again subjected to fine purification by preparative HPLC [Method 8]. This gave 160 mg of the pure title compound.

Chiral analytical HPLC [Method 11]: $R_t$=2.30 min.
LC/MS [Method 4]: $R_t$=1.04 min; MS [ESIpos]: m/z=610 $(M+H)^+$ $^1$H NMR (400 MHz, DMSO-$d_6$): δ [ppm]=about 3.26-3.35 (m, 1H, partially obscured by the water signal), 3.43-3.54 (m, 1H), 3.54-3.64 (m, 1H), 3.82 (dd, 1H), 3.95 (dd, 1H), 4.10 (dd, 1H), 4.21-4.33 (m, 2H), 4.35 (s, 2H), 6.32-6.53 (br. s, 2H), 6.92 (d, 1H), 7.45 (t, 1H), 7.57-7.80 (m, 7H), 8.17 (t, 2H).

Example 3

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[2-(trifluoromethyl)phenyl]propyl carbamate (Diastereomer 2)

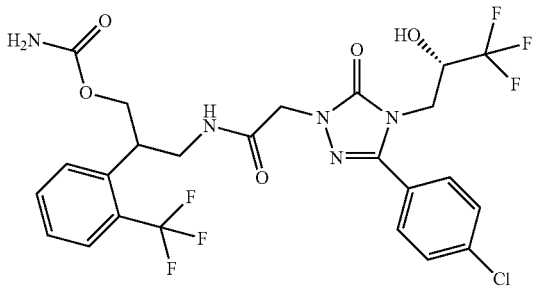 [SMILES: NC(=O)OCC(CNC(=O)Cn1nc(-c2ccc(Cl)cc2)n(C[C@H](O)C(F)(F)F)c1=O)c1ccccc1C(F)(F)F]

Last-eluting diastereomer from the chromatographic separation of 340 mg of the compound of Example 1 according to Method 10a. The material obtained in this manner (185 mg) was once again subjected to fine purification by preparative HPLC [Method 8]. This gave 160 mg of the pure title compound.

Chiral analytical HPLC [Method 11]: $R_t$=2.98 min.
LC/MS [Method 2]: $R_t$=2.16 min; MS [ESIpos]: m/z=610 $(M+H)^+$ $^1$H NMR (400 MHz, DMSO-$d_6$): δ [ppm]=about 3.29-3.35 (m, 1H, partially obscured by the water signal), 3.44-3.62 (m, 2H), 3.82 (dd, 1H), 3.95 (dd, 1H), 4.10 (dd, 1H), 4.24 (dd, 1H), 4.23-4.36 (m, 1H), 4.29-4.42 (m [AB], 2H), 6.33-6.53 (br. s, 2H), 6.93 (d, 1H), 7.45 (t, 1H), 7.60-7.78 (m, 7H), 8.19 (t, 1H).

Example 4

2-(2-Chlorophenyl)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]propyl carbamate (Diastereomer Mixture)

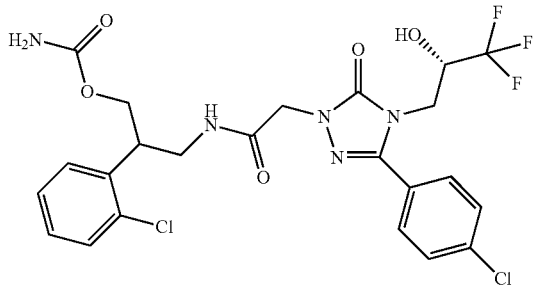 [SMILES: NC(=O)OCC(CNC(=O)Cn1nc(-c2ccc(Cl)cc2)n(C[C@H](O)C(F)(F)F)c1=O)c1ccccc1Cl]

185 mg (0.51 mmol) of the compound of Example 8A, 146 mg (0.76 mmol) of EDC and 108 mg (0.76 mmol) of HOBt in 5 ml of DMF were stirred at RT for 20 min. The resulting solution was then added dropwise to a solution of 116 mg (0.51 mmol) of the compound of Example 15A in 15 ml of acetonitrile. After 30 min at RT, the acetonitrile was removed on a rotary evaporator. 1 ml of 1 M hydrochloric acid was added to the remaining solution, and the mixture was separated directly into its components by preparative HPLC [Method 8]. The product fraction was freed from the solvent on a rotary evaporator and the residue was dried under high vacuum. This gave 150 mg (49% of theory) of the title compound as a diastereomer mixture.

LC/MS [Method 4]: $R_t$=0.99 min; MS [ESIpos]: m/z=576 $(M+H)^+$.

By preparative HPLC on a chiral phase [Method 5b], it was possible to separate the two diastereomers, see Example 5 and Example 6.

Example 5

2-(2-Chlorophenyl)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]propyl carbamate (Diastereomer 1)

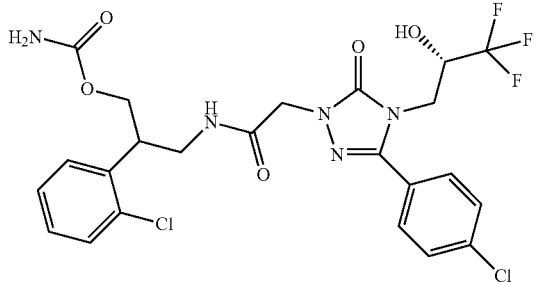 [SMILES: NC(=O)OCC(CNC(=O)Cn1nc(-c2ccc(Cl)cc2)n(C[C@H](O)C(F)(F)F)c1=O)c1ccccc1Cl]

First-eluting diastereomer from the chromatographic separation of 150 mg of the compound of Example 4 according to Method 5b. The material obtained in this manner (58 mg) was once again subjected to fine purification by preparative HPLC [Method 8]. This gave 46 mg of the pure title compound.

Chiral analytical HPLC [Method 6b]: $R_t$=2.51 min.

LC/MS [Method 4]: $R_t$=0.99 min; MS [ESIpos]: m/z=576 (M+H)$^+$ $^1$H NMR (400 MHz, DMSO-d$_6$): δ [ppm]=3.33-3.39 (m, 1H), 3.49 (dt, 1H), 3.66 (quin, 1H), 3.82 (dd, 1H), 3.96 (dd, 1H), 4.12-4.22 (m, 2H), 4.25-4.34 (m, 1H), 4.32-4.42 (m, 2H), 6.30-6.62 (br. s, 2H), 6.93 (d, 1H), 7.26 (td, 1H), 7.31 (td, 1H), 7.40-7.46 (m, 2H), 7.63 (d, 2H), 7.75 (d, 2H), 8.18 (t, 1H).

Example 6

2-(2-Chlorophenyl)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]propyl carbamate (Diastereomer 2)

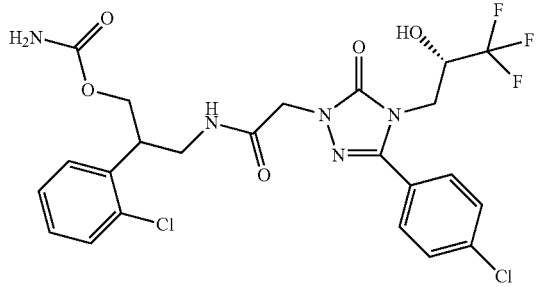 [SMILES: NC(=O)OCC(CNC(=O)Cn1nc(-c2ccc(Cl)cc2)n(C[C@H](O)C(F)(F)F)c1=O)c1ccccc1Cl]

Last-eluting diastereomer from the chromatographic separation of 150 mg of the compound of Example 4 according to Method 5b. The material obtained in this manner (63 mg) was once again subjected to fine purification by preparative HPLC [Method 8]. This gave 59 mg of the pure title compound.

Chiral analytical HPLC [Method 6b]: $R_t$=2.92 min.

LC/MS [Method 4]: $R_t$=1.00 min; MS [ESIpos]: m/z=576 (M+H)$^+$ $^1$H NMR (400 MHz, DMSO-d$_6$): δ [ppm]=3.32-3.40 (m, 1H), 3.47 (dt, 1H), 3.65 (quin, 1H), 3.82 (dd, 1H), 3.96 (dd, 1H), 4.12-4.22 (m, 2H), 4.24-4.35 (m, 1H), 4.31-4.43 (m [AB], 2H), 6.25-6.65 (br. s, 2H), 6.93 (d, 1H), 7.26 (dt, 1H), 7.31 (dt, 1H), 7.39-7.46 (m, 2H), 7.63 (d, 2H), 7.76 (d, 2H), 8.20 (t, 1H).

Example 7

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propyl carbamate (Diastereomer Mixture)

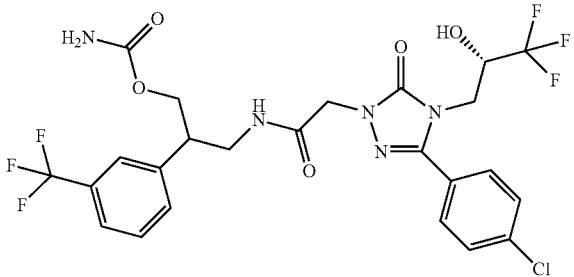 [SMILES: NC(=O)OCC(CNC(=O)Cn1nc(-c2ccc(Cl)cc2)n(C[C@H](O)C(F)(F)F)c1=O)c1cccc(C(F)(F)F)c1]

A mixture of 236 mg (0.64 mmol) of the compound of Example 8A, 385 mg (0.77 mmol) of the compound of Example 18A, 148 mg (0.77 mmol) of EDC, 110 mg (0.77 mmol) of HOBt and 225 µl (1.29 mmol) of N,N-diisopropylethylamine in 10 ml of DMF was stirred at RT overnight. 2 ml of 1 M hydrochloric acid were then added to the mixture, and the mixture was separated directly into its components by preparative HPLC [Method 8]. The product obtained was then re-purified by another preparative HPLC [Method 9]. The product fraction was freed from the solvent on a rotary evaporator and the residue was dried under high vacuum. This gave 140 mg (35% of theory) of the title compound as a diastereomer mixture.

LC/MS [Method 4]: $R_t$=1.04 min; MS [ESIpos]: m/z=610 (M+H)$^+$.

By preparative HPLC on a chiral phase [Method 5a], it was possible to separate the two diastereomers, see Example 8 and Example 9.

Example 8

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propyl carbamate (Diastereomer 1)

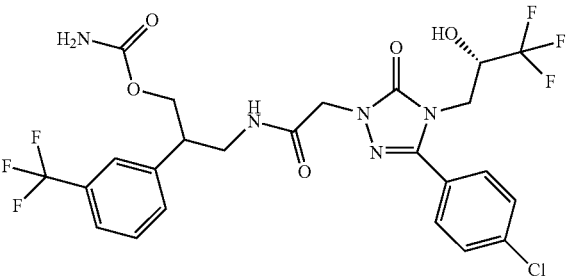 [SMILES: NC(=O)OCC(CNC(=O)Cn1nc(-c2ccc(Cl)cc2)n(C[C@H](O)C(F)(F)F)c1=O)c1cccc(C(F)(F)F)c1]

First-eluting diastereomer from the chromatographic separation of 140 mg of the compound of Example 7 according to Method 5a. The material obtained in this manner (82 mg) was once again subjected to fine purification by preparative HPLC [Method 8]. This gave 69 mg of the pure title compound.

Chiral analytical HPLC [Method 6a]: $R_t$=3.54 min.

LC/MS [Method 4]: $R_t$=1.04 min; MS [ESIpos]: m/z=610 (M+H)$^+$ $^1$H NMR (400 MHz, DMSO-d$_6$): δ [ppm]=3.20-3.29 (m, 1H), 3.33-3.42 (m, 1H), 3.42-3.52 (m, 1H), 3.82 (dd, 1H), 3.95 (dd, 1H), 4.17 (d, 2H), 4.23-4.41 (m, 3H), 6.25-6.70 (br. s, 2H), 6.92 (d, 1H), 7.50-7.66 (m, 6H), 7.71-7.77 (m, 2H), 8.16 (t, 1H).

Example 9

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propyl carbamate (Diastereomer 2)

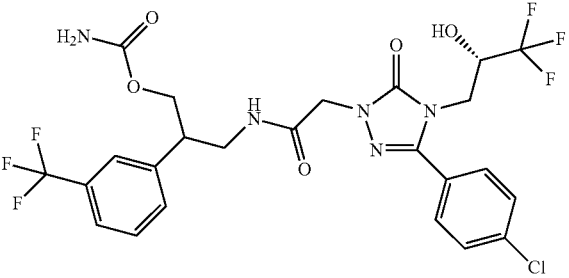 [SMILES: NC(=O)OCC(CNC(=O)Cn1nc(-c2ccc(Cl)cc2)n(C[C@H](O)C(F)(F)F)c1=O)c1cccc(C(F)(F)F)c1]

Last-eluting diastereomer from the chromatographic separation of 140 mg of the compound of Example 7 according to Method 5a. The product obtained in this manner (83 mg) was once again subjected to fine purification by preparative HPLC [Method 8]. This gave 67 mg of the pure title compound.

Chiral analytical HPLC [Method 6a]: $R_t$=4.29 min.

LC/MS [Method 4]: $R_t$=1.04 min; MS [ESIpos]: m/z=610 $(M+H)^+$ $^1$H NMR (400 MHz, DMSO-$d_6$): δ [ppm]=3.19-3.29 (m, 1H), 3.35-3.50 (m, 2H), 3.82 (dd, 1H), 3.95 (dd, 1H), 4.18 (br. d, 2H), 4.23-4.42 (m, 3H), 6.30-6.65 (br. s, 2H), 6.92 (d, 1H), 7.50-7.67 (m, 6H), 7.71-7.78 (m, 2H), 8.17 (t, 1H).

Example 10

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propyl ethylcarbamate (Diastereomer Mixture)

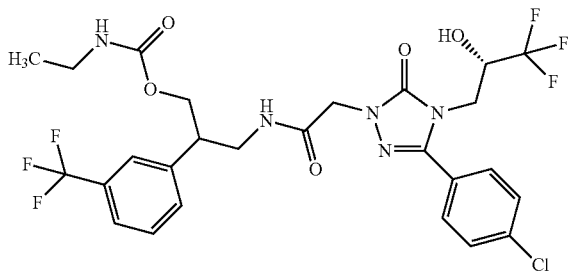 [SMILES: CCNC(=O)OCC(CNC(=O)Cn1nc(-c2ccc(Cl)cc2)n(C[C@H](O)C(F)(F)F)c1=O)c1cccc(C(F)(F)F)c1]

95 mg (0.26 mmol) of the compound of Example 8A, 75 mg (0.39 mmol) of EDC and 56 mg (0.39 mmol) of HOBt in 2.5 ml of DMF were stirred at RT for 5 min. The resulting solution was then added dropwise to a solution of 102 mg (0.26 mmol) of the compound of Example 20A in 7.5 ml of acetonitrile. After 30 min at RT, the acetonitrile was removed on a rotary evaporator. 1 ml of 1 M hydrochloric acid was added to the remaining solution, and the mixture was separated directly into its components by preparative HPLC [Method 8]. The product fraction was freed from the solvent on a rotary evaporator and the residue was dried under high vacuum. This gave 123 mg (73% of theory) of the title compound as a diastereomer mixture.

LC/MS [Method 4]: $R_t$=1.13 min; MS [ESIpos]: m/z=638 $(M+H)^+$.

By preparative HPLC on a chiral phase [Method 10b], it was possible to separate the two diastereomers, see Example 11 and Example 12.

Example 11

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propyl ethylcarbamate (Diastereomer 1)

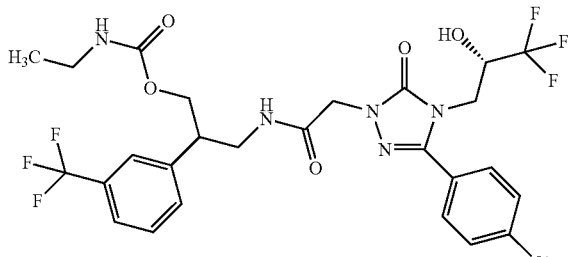

First-eluting diastereomer from the chromatographic separation of 120 mg of the compound of Example 10 according to Method 10b. The material obtained in this manner (62 mg) was once again subjected to fine purification by preparative HPLC [Method 8]. This gave 50 mg of the pure title compound.

Chiral analytical HPLC [Method 11]: $R_t$=1.77 min.

LC/MS [Method 3]: $R_t$=1.31 min; MS [ESIpos]: m/z=638 $(M+H)^+$ $^1$H NMR (400 MHz, DMSO-$d_6$): δ [ppm]=0.95 (t, 3H), 2.94 (quin, 2H), 3.19-3.29 (m, 1H), 3.34-3.52 (m, 2H), 3.82 (dd, 1H), 3.95 (dd, 1H), 4.14-4.42 (m, 5H), 6.92 (d, 1H), 7.07 (t, 1H), 7.50-7.67 (m, 6H), 7.74 (d, 2H), 8.17 (t, 1H).

Example 12

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propyl ethylcarbamate (Diastereomer 2)

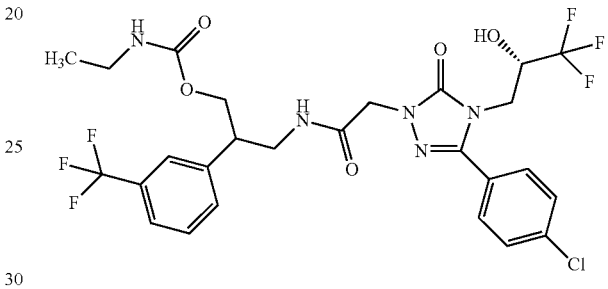

Last-eluting diastereomer from the chromatographic separation of 120 mg of the compound of Example 10 according to Method 10b. The material obtained in this manner (about 60 mg) was once again subjected to fine purification by preparative HPLC [Method 8]. This gave 52 mg of the pure title compound.

Chiral analytical HPLC [Method 11]: $R_t$=2.28 min.

LC/MS [Method 3]: $R_t$=1.31 min; MS [ESIpos]: m/z=638 $(M+H)^+$ $^1$H NMR (400 MHz, DMSO-$d_6$; signals of the main rotamer): δ [ppm]=0.95 (t, 3H), 2.89-2.99 (m, 2H), 3.19-3.29 (m, 1H), 3.35-3.53 (m, 2H), 3.83 (dd, 1H), 3.95 (dd, 1H), 4.15-4.42 (m, 5H), 6.92 (d, 1H), 7.07 (t, 1H), 7.49-7.67 (m, 6H), 7.75 (d, 2H), 8.18 (t, 1H).

Example 13 tert-Butyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-1-[2-(trifluoromethyl)phenyl]ethyl}carbamate (Diastereomer Mixture)

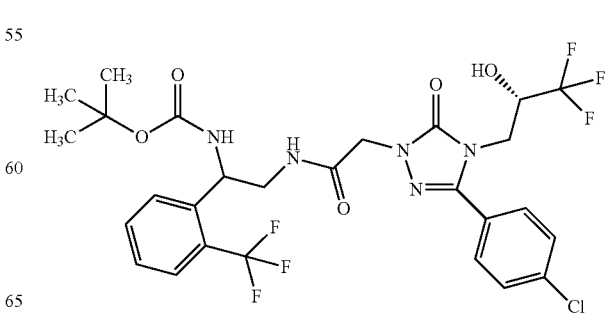

A mixture of 295 mg (0.81 mmol) of the compound of Example 8A, 270 mg (0.89 mmol) of tert-butyl {2-amino-1-[2-(trifluoromethyl)phenyl]ethyl}carbamate, 216 mg (1.13 mmol) of EDC and 153 mg (1.13 mmol) of HOBt in 7 ml of DMF was stirred at RT for 1 h. 1 ml of 1 M hydrochloric acid was added to the mixture, and the mixture was separated directly into its components by preparative HPLC [Method 8]. The product fraction was freed from the solvent on a rotary evaporator and the residue was dried under high vacuum. This gave 494 mg (94% of theory) of the title compound as a diastereomer mixture.

LC/MS [Method 4]: $R_t$=1.22 min; MS [ESIpos]: m/z=652 (M+H)$^+$.

By preparative HPLC on a chiral phase [Method 13a], it was possible to separate the two diastereomers, see Example 14 and Example 15.

Example 14 tert-Butyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-1-[2-(trifluoromethyl)phenyl]ethyl}carbamate (Diastereomer 1)

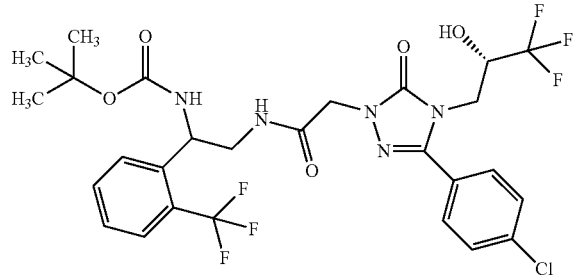 [SMILES: CC(C)(C)OC(=O)NC(CNC(=O)Cn1nc(-c2ccc(Cl)cc2)n(C[C@H](O)C(F)(F)F)c1=O)c1ccccc1C(F)(F)F]

First-eluting diastereomer (145 mg) from the chromatographic separation of 490 mg of the compound of Example 13 according to Method 13a.

Chiral analytical HPLC [Method 14]: $R_t$=5.25 min.
LC/MS [Method 4]: $R_t$=1.22 min; MS [ESIpos]: m/z=652 (M+H)$^+$ $^1$H NMR (400 MHz, DMSO-$d_6$; signals of the main rotamer): δ [ppm]=1.33 (s, 9H), 3.21-3.41 (m, 2H), 3.83 (dd, 1H), 3.97 (dd, 1H), 4.22-4.33 (m, 1H), 4.35-4.48 (m, 2H), 4.96-5.08 (m, 1H), 6.92 (d, 1H), 7.42-7.53 (m, 2H), 7.60-7.70 (m, 4H), 7.71-7.80 (m, 3H), 8.26 (br. t, 1H).

Example 15 tert-Butyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-1-[2-(trifluoromethyl)phenyl]ethyl}carbamate (Diastereomer 2)

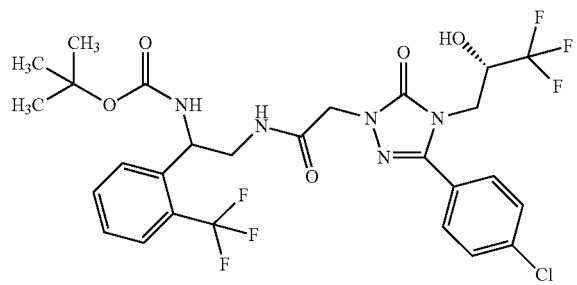 [SMILES: CC(C)(C)OC(=O)NC(CNC(=O)Cn1nc(-c2ccc(Cl)cc2)n(C[C@H](O)C(F)(F)F)c1=O)c1ccccc1C(F)(F)F]

Last-eluting diastereomer (117 mg) from the chromatographic separation of 490 mg of the compound of Example 13 according to Method 13a.

Chiral analytical HPLC [Method 14]: $R_t$=5.94 min.
LC/MS [Method 4]: $R_t$=1.22 min; MS [ESIpos]: m/z=652 (M+H)$^+$ $^1$H NMR (400 MHz, DMSO-$d_6$; signals of the main rotamer): δ [ppm]=1.33 (br. s, 9H), 3.20-3.41 (m, 2H), 3.84 (dd, 1H), 3.96 (dd, 1H), 4.23-4.34 (m, 1H), 4.41 (br. s, 2H), 4.97-5.07 (m, 1H), 6.93 (d, 1H), 7.43-7.52 (m, 2H), 7.61-7.70 (m, 4H), 7.71-7.79 (m, 3H), 8.21-8.30 (m, 1H).

Example 16

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(methylsulphonyl)amino]-2-[2-(trifluoromethyl)phenyl]ethyl}acetamide (Diastereomer 1)

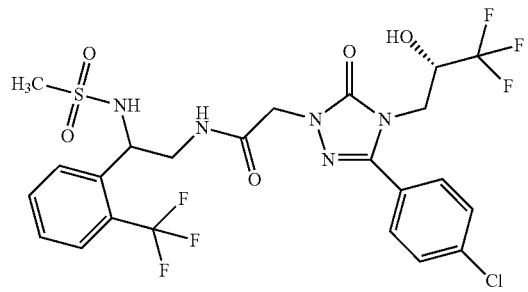 [SMILES: CS(=O)(=O)NC(CNC(=O)Cn1nc(-c2ccc(Cl)cc2)n(C[C@H](O)C(F)(F)F)c1=O)c1ccccc1C(F)(F)F]

At RT, 13 μl of methanesulphonyl chloride were added to a solution of 90 mg (0.15 mmol) of the compound of Example 56A in 1.5 ml of pyridine. The mixture was stirred at RT for 1 h, and another 12 ml of methanesulphonyl chloride were added (0.32 mmol, 2.1 eq. in total). After 1 h, the volatile components were removed on a rotary evaporator. The residue was dissolved in a little DMSO and purified by preparative HPLC [Method 8]. This gave 59 mg (61% of theory) of the title compound.

LC/MS [Method 4]: $R_t$=1.06 min; MS [ESIpos]: m/z=630 (M+H)$^+$ $^1$H NMR (400 MHz, DMSO-$d_6$): δ [ppm]=2.70 (s, 3H), 3.31-3.46 (m, 2H), 3.84 (dd, 1H), 3.98 (dd, 1H), 4.22-4.35 (m, 1H), 4.37-4.50 (m [AB], 2H), 4.75-4.84 (m, 1H), 6.93 (d, 1H), 7.51 (t, 1H), 7.60-7.66 (m, 2H), 7.68-7.79 (m, 4H), 7.87 (d, 1H), 7.98 (d, 1H), 8.29 (t, 1H).

Example 17

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(methylsulphonyl)amino]-2-[2-(trifluoromethyl)phenyl]ethyl}acetamide (Diastereomer 2)

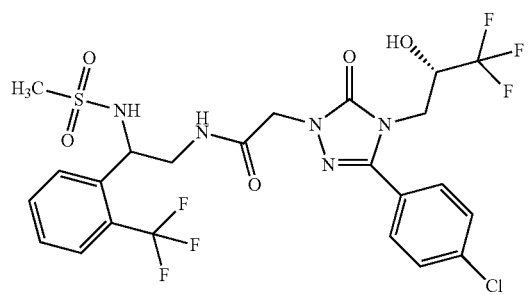 [SMILES: CS(=O)(=O)NC(CNC(=O)Cn1nc(-c2ccc(Cl)cc2)n(C[C@H](O)C(F)(F)F)c1=O)c1ccccc1C(F)(F)F]

Analogously to Example 16, treatment of 67 mg (0.114 mmol) of the compound of Example 57A with methane-sulphonyl chloride gave 40 mg (56% of theory) of the title compound.

LC/MS [Method 4]: $R_t$=1.06 min; MS [ESIpos]: m/z=630 (M+H)$^+$ $^1$H NMR (400 MHz, DMSO-d$_6$): δ [ppm]=2.70 (s, 3H), 3.27-3.37 (m, 1H), 3.37-3.47 (m, 1H), 3.84 (dd, 1H), 3.97 (dd, 1H), 4.23-4.35 (m, 1H), 4.44 (s, 2H), 4.76-4.85 (m, 1H), 6.92 (d, 1H), 7.51 (t, 1H), 7.64 (d, 2H), 7.68-7.78 (m, 4H), 7.86 (d, 1H), 7.98 (d, 1H), 8.28 (t, 1H).

Example 18 tert-Butyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-1-(2,3-dichlorophenyl)ethyl}carbamate (Diastereomer Mixture)

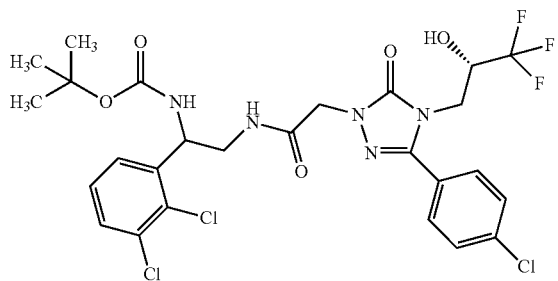 [SMILES: CC(C)(C)OC(=O)NC(CNC(=O)Cn1nc(-c2ccc(Cl)cc2)n(C[C@H](O)C(F)(F)F)c1=O)c1cccc(Cl)c1Cl]

185 mg (0.51 mmol) of the compound of Example 8A and 170 mg (0.56 mmol) of the compound of Example 24A were reacted analogously to Example 13. This gave 300 mg (88% of theory) of the title compound as a diastereomer mixture.

LC/MS [Method 4]: $R_t$=1.24 min; MS [ESIpos]: m/z=652 (M+H)$^+$ $^1$H NMR (400 MHz, DMSO-d$_6$): δ [ppm]=1.34 (s, 9H), 3.27-3.42 (m, 2H), 3.83 (dd, 1H), 3.97 (2 dd, tog. 1H), 4.23-4.48 (m, 3H), 5.03-5.14 (m, 1H), 6.92 (2 d, tog. 1H), 7.36 (t, 1H), 7.41-7.47 (m, 1H), 7.50-7.58 (m, 2H), 7.63 (d, 2H), 7.75 (d, 2H), 8.22 (2 t, tog. 1H).

By preparative HPLC on a chiral phase [Method 15a], it was possible to separate the two diastereomers, see Example 19 and Example 20.

Example 19 tert-Butyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-1-(2,3-dichlorophenyl)ethyl}carbamate (Diastereomer 1)

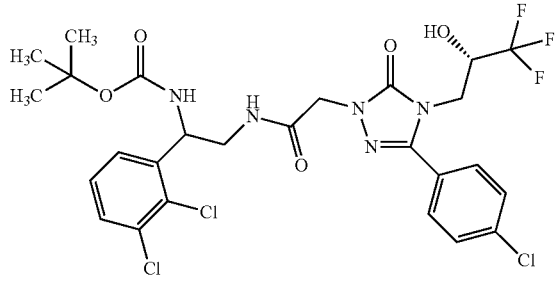 [SMILES: CC(C)(C)OC(=O)NC(CNC(=O)Cn1nc(-c2ccc(Cl)cc2)n(C[C@H](O)C(F)(F)F)c1=O)c1cccc(Cl)c1Cl]

First-eluting diastereomer (150 mg) from the chromatographic separation of 300 mg of the compound of Example 18 according to Method 15a.

Chiral analytical HPLC [Method 16]: $R_t$=2.15 min.

LC/MS [Method 3]: $R_t$=1.43 min; MS [ESIneg]: m/z=650 (M–H)$^-$.

Example 20 tert-Butyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-1-(2,3-dichlorophenyl)ethyl}carbamate (Diastereomer 2)

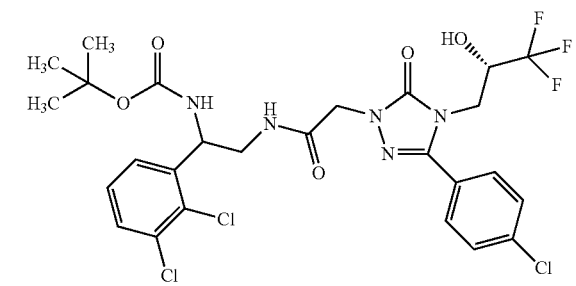 [SMILES: CC(C)(C)OC(=O)NC(CNC(=O)Cn1nc(-c2ccc(Cl)cc2)n(C[C@H](O)C(F)(F)F)c1=O)c1cccc(Cl)c1Cl]

Last-eluting diastereomer (150 mg) from the chromatographic separation of 300 mg of the compound of Example 18 according to Method 15a.

Chiral analytical HPLC [Method 16]: $R_t$=5.33 min.

LC/MS [Method 3]: $R_t$=1.43 min; MS [ESIneg]: m/z=650 (M–H)$^-$.

Example 21

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(2,3-dichlorophenyl)-2-[(methylsulphonyl)amino]ethyl}acetamide (Diastereomer 1)

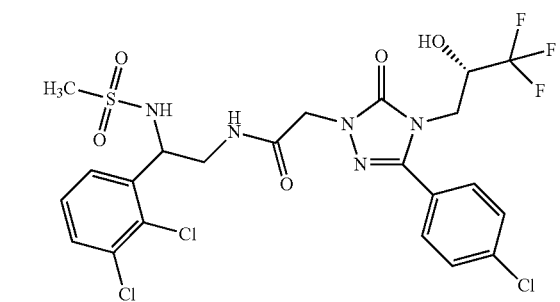 [SMILES: CS(=O)(=O)NC(CNC(=O)Cn1nc(-c2ccc(Cl)cc2)n(C[C@H](O)C(F)(F)F)c1=O)c1cccc(Cl)c1Cl]

Analogously to Example 16, treatment of 77 mg (0.131 mmol) of the compound of Example 54A with methane-sulphonyl chloride gave 55 mg (67% of theory) of the title compound.

LC/MS [Method 4]: $R_t$=1.08 min; MS [ESIpos]: m/z=630 (M+H)$^+$ $^1$H NMR (400 MHz, DMSO-d$_6$): δ [ppm]=2.83 (s, 3H), 3.31-3.43 (m, 2H), 3.84 (dd, 1H), 3.98 (dd, 1H), 4.23-4.35 (m, 1H), 4.36-4.49 (m [AB], 2H), 4.94-5.02 (m, 1H), 6.93 (d, 1H), 7.42 (t, 1H), 7.56-7.67 (m, 4H), 7.73-7.80 (m, 2H), 7.98 (d, 1H), 8.30 (t, 1H).

Example 22

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(2,3-dichlorophenyl)-2-[(methylsulphonyl)amino]ethyl}acetamide (Diastereomer 2)

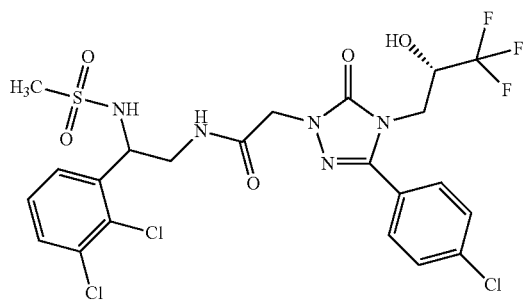 [SMILES: CS(=O)(=O)NC(CNC(=O)Cn1nc(-c2ccc(Cl)cc2)n(C[C@H](O)C(F)(F)F)c1=O)c1cccc(Cl)c1Cl]

Analogously to Example 16, treatment of 76 mg (0.13 mmol) of the compound of Example 55A with methanesulphonyl chloride gave 59 mg (73% of theory) of the title compound.

LC/MS [Method 4]: $R_t$=1.08 min; MS [ESIpos]: m/z=630 (M+H)$^+$ $^1$H NMR (400 MHz, DMSO-d$_6$): δ [ppm]=2.83 (s, 3H), 3.34-3.44 (m, 2H), 3.84 (dd, 1H), 3.97 (dd, 1H), 4.29 (d, 1H), 4.43 (s, 2H), 4.94-5.02 (m, 1H), 6.93 (d, 1H), 7.42 (t, 1H), 7.57-7.62 (m, 2H), 7.62-7.67 (m, 2H), 7.72-7.78 (m, 2H), 7.99 (d, 1H), 8.28 (t, 1H).

Example 23

N-[2-(Carbamoylamino)-2-(2,3-dichlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 1)

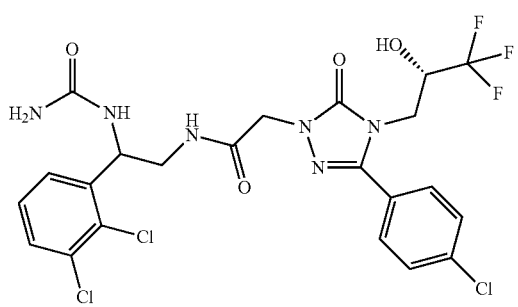 [SMILES: NC(=O)NC(CNC(=O)Cn1nc(-c2ccc(Cl)cc2)n(C[C@H](O)C(F)(F)F)c1=O)c1cccc(Cl)c1Cl]

12 mg of potassium cyanate (153 μmol) were added to a mixture of 30 mg (51 μmol) of the compound of Example 54A, 1 ml of water and 1 ml of methanol, and the mixture was stirred at 40° C. for 1.5 h. An additional 6 mg (75 μmol) of potassium cyanate were added, and stirring of the reaction mixture was continued at RT overnight. A few ml of DMSO were added, and the entire solution was separated by preparative HPLC [Method 8]. The product fraction was freed from the solvent on a rotary evaporator and the residue was dried under high vacuum. This gave 17 mg (56% of theory) of the title compound.

LC/MS [Method 4]: $R_t$=0.98 min; MS [ESIpos]: m/z=595 (M+H)$^+$ $^1$H NMR (400 MHz, DMSO-d$_6$): δ [ppm]=3.28-3.38 (m, 2H), 3.83 (dd, 1H), 3.96 (dd, 1H), 4.24-4.35 (m, 1H), 4.34-4.46 (m [AB], 2H), 5.14 (q, 1H), 5.64 (s, 2H), 6.69 (d, 1H), 6.94 (d, 1H), 7.33-7.40 (m, 2H), 7.50-7.57 (m, 1H), 7.64 (d, 2H), 7.76 (d, 2H), 8.29 (t, 1H).

Example 24

N-[2-(Carbamoylamino)-2-(2,3-dichlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 2)

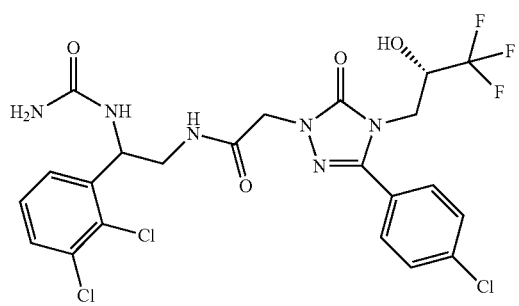 [SMILES: NC(=O)NC(CNC(=O)Cn1nc(-c2ccc(Cl)cc2)n(C[C@H](O)C(F)(F)F)c1=O)c1cccc(Cl)c1Cl]

Analogously to Example 23, 30 mg (51 μmol) of the compound of Example 55A and potassium cyanate gave 19 mg (63% of theory) of the title compound.

LC/MS [Method 4]: $R_t$=0.99 min; MS [ESIpos]: m/z=595 (M+H)$^+$ $^1$H NMR (400 MHz, DMSO-d$_6$): δ [ppm]=3.27-3.42 (m, 2H), 3.83 (dd, 1H), 3.96 (dd, 1H), 4.24-4.35 (m, 1H), 4.34-4.46 (m [AB], 2H), 5.10-5.18 (m, 1H), 5.63 (s, 2H), 6.69 (d, 1H), 6.92 (d, 1H), 7.32-7.41 (m, 2H), 7.54 (dd, 1H), 7.64 (d, 2H), 7.76 (d, 2H), 8.28 (t, 1H).

Example 25

N-{2-(2-Chlorophenyl)-2-[(methylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer Mixture)

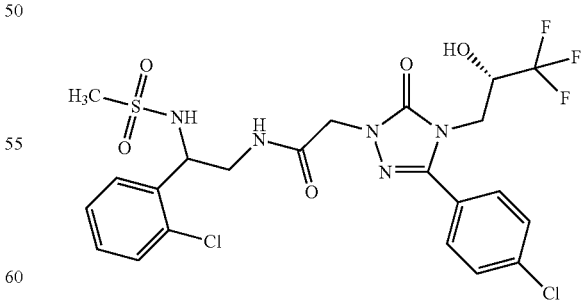

A mixture of 249 mg (0.68 mmol) of the compound of Example 8A, 186 mg (0.75 mmol) of the compound of Example 27A, 195 mg (1.02 mmol) of EDC and 138 mg (1.02 mmol) of HOBt in 6.5 ml of DMF was stirred at RT for 2 h. The mixture was then separated directly into its components by preparative HPLC [Method 8]. The product fraction was freed from the solvent on a rotary evaporator and the residue was dried under high vacuum. This gave 356 mg (83% of theory) of the title compound as a diastereomer mixture.

LC/MS [Method 4]: $R_t$=1.01 min; MS [ESIpos]: m/z=596 (M+H)$^+$.

By preparative HPLC on a chiral phase [Method 17a], it was possible to separate the two diastereomers, see Example 26 and Example 27.

Example 26

N-{2-(2-Chlorophenyl)-2-[(methylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 1)

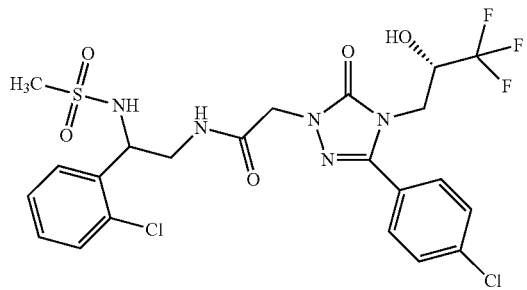 [SMILES: CS(=O)(=O)NC(CNC(=O)Cn1nc(-c2ccc(Cl)cc2)n(C[C@H](O)C(F)(F)F)c1=O)c1ccccc1Cl]

First-eluting diastereomer from the chromatographic separation of 356 mg of the compound of Example 25 according to Method 17a. The material obtained in this manner (150 mg) was once again subjected to fine purification by preparative HPLC [Method 8]. This gave 100 mg of the pure title compound.

Chiral analytical HPLC [Method 18a]: $R_t$=4.10 min.
LC/MS [Method 4]: $R_t$=1.01 min; MS [ESIpos]: m/z=596 (M+H)$^+$ $^1$H NMR (400 MHz, DMSO-d$_6$): δ [ppm]=2.78 (s, 3H), 3.31-3.38 (m, 2H), 3.84 (dd, 1H), 3.98 (dd, 1H), 4.22-4.36 (m, 1H), 4.37-4.49 (m [AB], 2H), 4.89-4.97 (m, 1H), 6.93 (d, 1H), 7.31 (dt, 1H), 7.36-7.46 (m, 2H), 7.60-7.67 (m, 3H), 7.76 (d, 2H), 7.91 (d, 1H), 8.29 (t, 1H).

Example 27

N-{2-(2-Chlorophenyl)-2-[(methylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 2)

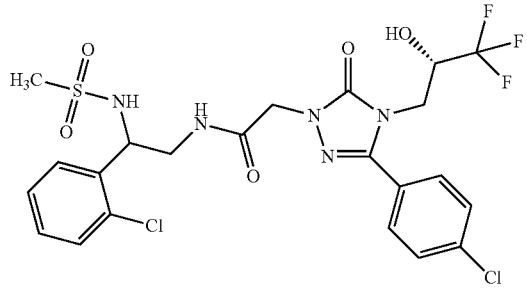 [SMILES: CS(=O)(=O)NC(CNC(=O)Cn1nc(-c2ccc(Cl)cc2)n(C[C@H](O)C(F)(F)F)c1=O)c1ccccc1Cl]

Last-eluting diastereomer from the chromatographic separation of 356 mg of the compound of Example 25 according to Method 17a. The material obtained in this manner (160 mg) was once again subjected to fine purification by preparative HPLC [Method 8]. This gave 120 mg of the pure title compound.

Chiral analytical HPLC [Method 18a]: $R_t$=4.94 min.
LC/MS [Method 4]: $R_t$=1.02 min; MS [ESIpos]: m/z=596 (M+H)$^+$ $^1$H NMR (400 MHz, DMSO-d$_6$): δ [ppm]=2.78 (s, 3H), 3.29-3.42 (m, 2H), 3.84 (dd, 1H), 3.97 (dd, 1H), 4.23-4.35 (m, 1H), 4.43 (s, 2H), 4.89-4.99 (m, 1H), 6.93 (d, 1H), 7.32 (dt, 1H), 7.36-7.46 (m, 2H), 7.61-7.67 (m, 3H), 7.76 (d, 2H), 7.92 (d, 1H), 8.28 (t, 1H).

Example 28

N-{2-(2-Chlorophenyl)-2-[(ethylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer Mixture)

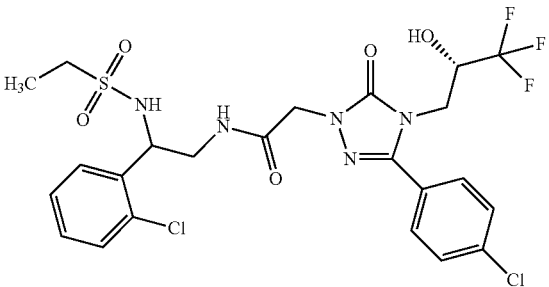 [SMILES: CCS(=O)(=O)NC(CNC(=O)Cn1nc(-c2ccc(Cl)cc2)n(C[C@H](O)C(F)(F)F)c1=O)c1ccccc1Cl]

Analogously to Example 25, 216 mg (0.59 mmol) of the compound of Example 8A and 190 mg (90% pure, 0.65 mmol) of the compound of Example 29A gave 274 mg (73% of theory) of the title compound.

LC/MS [Method 2]: $R_t$=2.24 min; MS [ESIpos]: m/z=610 (M+H)$^+$.

By preparative HPLC on a chiral phase [Method 17b], it was possible to separate the two diastereomers, see Example 29 and Example 30.

Example 29

N-{2-(2-Chlorophenyl)-2-[(ethylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 1)

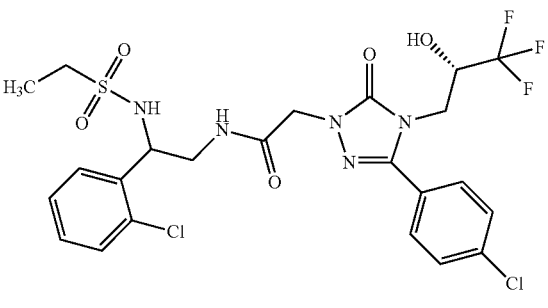 [SMILES: CCS(=O)(=O)NC(CNC(=O)Cn1nc(-c2ccc(Cl)cc2)n(C[C@H](O)C(F)(F)F)c1=O)c1ccccc1Cl]

First-eluting diastereomer from the chromatographic separation of 274 mg of the compound of Example 28 according to Method 17b. The material obtained in this manner (123 mg) was once again subjected to fine purification by preparative HPLC [Method 19]. This gave 92 mg of the pure title compound.

Chiral analytical HPLC [Method 18a]: $R_t$=4.27 min.
LC/MS [Method 4]: $R_t$=1.04 min; MS [ESIpos]: m/z=610 (M+H)$^+$
$^1$H NMR (400 MHz, DMSO-d$_6$): δ [ppm]=1.08 (t, 3H), 2.68-2.80 (m, 1H), 2.88 (dq, 1H), 3.30-3.44 (m, 2H), 3.84 (dd, 1H), 3.97 (dd, 1H), 4.24-4.35 (m, 1H), 4.35-4.46 (m [AB], 2H), 4.93 (q, 1H), 6.91 (d, 1H), 7.27-7.34 (m, 1H), 7.36-7.45 (m, 2H), 7.60-7.68 (m, 3H), 7.76 (d, 2H), 7.91 (d, 1H), 8.24 (t, 1H).

Example 30

N-{2-(2-Chlorophenyl)-2-[(ethylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 2)

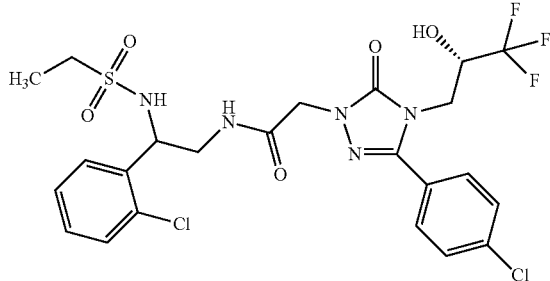 [SMILES: CCS(=O)(=O)NC(CNC(=O)Cn1nc(-c2ccc(Cl)cc2)n(C[C@H](O)C(F)(F)F)c1=O)c1ccccc1Cl]

Last-eluting diastereomer from the chromatographic separation of 274 mg of the compound of Example 28 according to Method 17b. The material obtained in this manner (109 mg) was once again subjected to fine purification by preparative HPLC [Method 19]. This gave 82 mg of the pure title compound.
Chiral analytical HPLC [Method 18a]: $R_t$=5.02 min.
LC/MS [Method 4]: $R_t$=1.04 min; MS [ESIpos]: m/z=610 (M+H)$^+$
$^1$H NMR (500 MHz, DMSO-d$_6$): δ [ppm]=1.08 (t, 3H), 2.74 (dq, 1H), 2.88 (dq, 1H), 3.27-3.35 (m, 1H), 3.35-3.44 (m, 1H), 3.84 (dd, 1H), 3.96 (dd, 1H), 4.24-4.34 (m, 1H), 4.35-4.45 (m [AB], 2H), 4.90-4.99 (m, 1H), 6.88 (d, 1H), 7.27-7.34 (m, 1H), 7.36-7.45 (m, 2H), 7.60-7.68 (m, 3H), 7.75 (d, 2H), 7.88 (d, 1H), 8.20 (br. t, 1H).

Example 31

N-[2-(Carbamoylamino)-2-(2-chlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer Mixture)

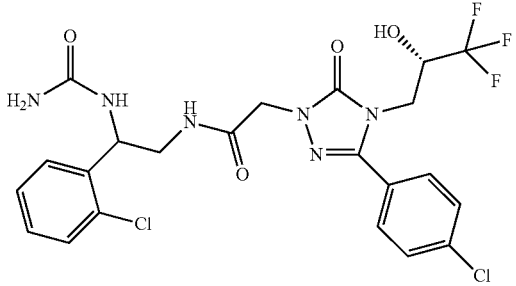 [SMILES: NC(=O)NC(CNC(=O)Cn1nc(-c2ccc(Cl)cc2)n(C[C@H](O)C(F)(F)F)c1=O)c1ccccc1Cl]

Analogously to Example 25, 118 mg (0.32 mmol) of the compound of Example 8A and 94 mg (81% pure, 0.36 mmol) of the compound of Example 31A gave 138 mg (73% of theory) of the title compound.

LC/MS [Method 2]: $R_t$=2.02 min; MS [ESIpos]: m/z=561 (M+H)$^+$.

By preparative HPLC on a chiral phase [Method 17c], it was possible to separate the two diastereomers, see Example 32 and Example 33.

Example 32

N-[2-(Carbamoylamino)-2-(2-chlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 1)

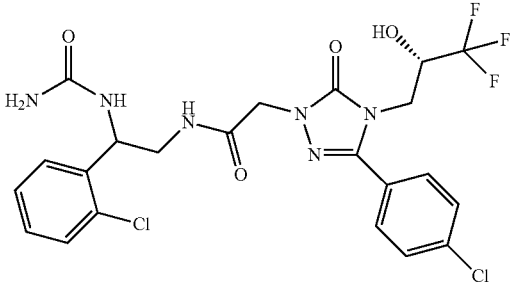 [SMILES: NC(=O)NC(CNC(=O)Cn1nc(-c2ccc(Cl)cc2)n(C[C@H](O)C(F)(F)F)c1=O)c1ccccc1Cl]

First-eluting diastereomer from the chromatographic separation of 138 mg of the compound of Example 31 according to Method 17c. The material obtained in this manner (31 mg) was once again subjected to fine purification by preparative HPLC [Method 19]. This gave 21 mg of the pure title compound.
Chiral analytical HPLC [Method 18b]: $R_t$=6.80 min.
LC/MS [Method 4]: $R_t$=0.94 min; MS [ESIpos]: m/z=561 (M+H)$^+$
$^1$H NMR (500 MHz, DMSO-d$_6$): δ [ppm]=3.31-3.37 (m, 2H), 3.84 (dd, 1H), 3.96 (dd, 1H), 4.25-4.35 (m, 1H), 4.35-4.45 (m [AB], 2H), 5.13 (q, 1H), 5.56 (s, 2H), 6.58 (d, 1H), 6.89 (d, 1H), 7.25-7.30 (m, 1H), 7.33 (t, 1H), 7.38-7.45 (m, 2H), 7.63 (d, 2H), 7.76 (d, 2H), 8.21 (br. t, 1H).

Example 33

N-[2-(Carbamoylamino)-2-(2-chlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 2)

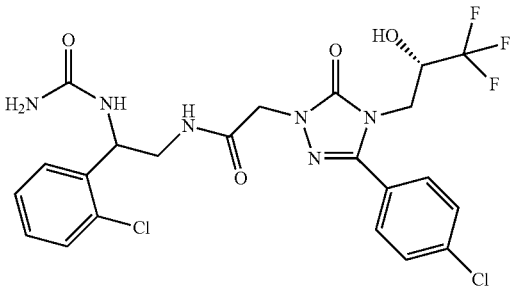 [SMILES: NC(=O)NC(CNC(=O)Cn1nc(-c2ccc(Cl)cc2)n(C[C@H](O)C(F)(F)F)c1=O)c1ccccc1Cl]

Last-eluting diastereomer from the chromatographic separation of 138 mg of the compound of Example 31 according to Method 17c. The material obtained in this manner (40 mg) was once again subjected to fine purification by preparative HPLC [Method 19]. This gave 24 mg of the pure title compound.

Chiral analytical HPLC [Method 18b]: $R_t$=8.50 min.

LC/MS [Method 4]: $R_t$=0.93 min; MS [ESIpos]: m/z=561 (M+H)$^+$ $^1$H NMR (500 MHz, DMSO-d$_6$): δ [ppm]=3.28-3.37 (m, 2H), 3.83 (dd, 1H), 3.97 (dd, 1H), 4.25-4.35 (m, 1H), 4.35-4.45 (m [AB], 2H), 5.12 (q, 1H), 5.57 (br. s, 2H), 6.58 (d, 1H), 6.90 (d, 1H), 7.25-7.30 (m, 1H), 7.34 (t, 1H), 7.38-7.44 (m, 2H), 7.63 (d, 2H), 7.76 (d, 2H), 8.22 (br. t, 1H).

Example 34 tert-Butyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-1-[3-(trifluoromethyl)phenyl]ethyl}carbamate (Diastereomer Mixture)

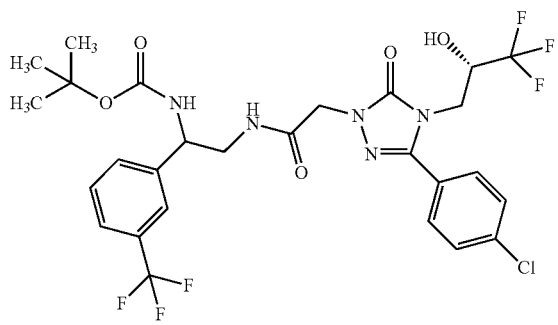 [SMILES: CC(C)(C)OC(=O)NC(CNC(=O)Cn1nc(-c2ccc(Cl)cc2)n(C[C@H](O)C(F)(F)F)c1=O)c1cccc(C(F)(F)F)c1]

Analogously to Example 25, 152 mg (0.42 mmol) of the compound of Example 8A and 150 mg (0.46 mmol) of tert-butyl {2-amino-1-[3-(trifluoromethyl)phenyl]ethyl}carbamate gave 240 mg (88% of theory) of the title compound.

LC/MS [Method 4]: $R_t$=1.23 min; MS [ESIpos]: m/z=652 (M+H)$^+$ $^1$H NMR (400 MHz, DMSO-d$_6$): δ [ppm]=1.35 (s, 9H), 3.27-3.42 (m, 2H), 3.83 (dd, 1H), 3.91-4.01 (m, 1H), 4.22-4.44 (m, 3H), 4.68-4.78 (m, 1H), 6.92 (2 d, tog. 1H), 7.49-7.68 (m, 7H), 7.72-7.78 (m, 2H), 8.22 (2 t, tog. 1H).

Example 35

N-{2-Acetamido-2-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer Mixture)

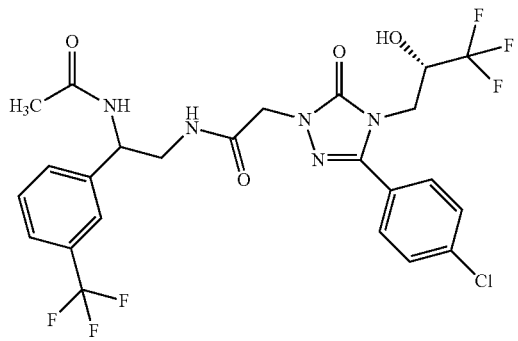 [SMILES: CC(=O)NC(CNC(=O)Cn1nc(-c2ccc(Cl)cc2)n(C[C@H](O)C(F)(F)F)c1=O)c1cccc(C(F)(F)F)c1]

20 µl (0.11 mmol) of N,N-diisopropylethylamine were added to a solution of 60 mg (0.10 mmol) of the compound of Example 58A in 1 ml of dichloromethane. The mixture was cooled to 0° C., 10 µl (0.10 mmol) of acetic anhydride were then added and stirring was continued at 0° C. for 1 h. The volatile components were then removed on a rotary evaporator. The residue was dissolved in a little DMSO and separated by preparative HPLC [Method 8]. The product-containing fraction was freed from the solvent on a rotary evaporator and the residue was dried under high vacuum. This gave 50 mg (83% of theory) of the title compound.

LC/MS [Method 2]: $R_t$=2.19 min; MS [ESIpos]: m/z=594 (M+H)$^+$ $^1$H NMR (400 MHz, DMSO-d$_6$): δ [ppm]=1.86 (s, 3H), 3.30-3.47 (m, 2H), 3.83 (dd, 1H), 3.96 (br. d, 1H), 4.26-4.43 (m, 3H), 5.02 (q, 1H), 6.91 (d, 1H), 7.51-7.69 (m, 6H), 7.75 (d, 2H), 8.19 (br. t, 1H), 8.39 (d, 1H).

Example 36

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-formamido-2-[3-(trifluoromethyl)phenyl]ethyl}acetamide (Diastereomer Mixture)

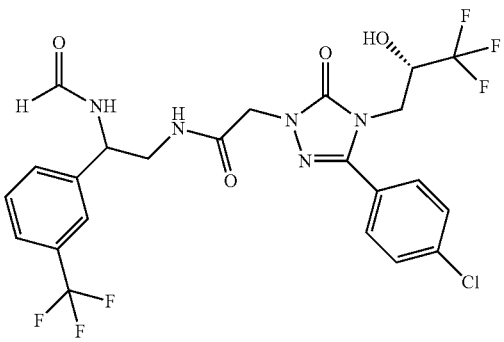 [SMILES: O=CNC(CNC(=O)Cn1nc(-c2ccc(Cl)cc2)n(C[C@H](O)C(F)(F)F)c1=O)c1cccc(C(F)(F)F)c1]

20 µl (112 µmol) of N,N-diisopropylethylamine were added to a solution of 60 mg (102 µmol) of the compound of Example 58A in 1 ml of THF. The mixture was cooled to 0° C., 18 mg (107 µmol) of 4-nitrophenyl formate were then added a little at a time and stirring was continued at 0° C. for 1 h. Since LC/MS analysis of the reaction mixture indicated the additional formation of an O-formylated byproduct, 408 µl of a 1 N solution of lithium hydroxide in water were added to the reaction mixture. Stirring of the mixture was then continued at RT overnight. The volatile components were then removed on a rotary evaporator. The residue was dissolved in a little DMSO and separated by preparative HPLC [Method 8]. The product-containing fraction was freed from the solvent on a rotary evaporator and the residue was dried under high vacuum. This gave 35 mg (59% of theory) of the title compound.

LC/MS [Method 2]: $R_t$=2.17 min; MS [ESIpos]: m/z=580 (M+H)$^+$ $^1$H NMR (400 MHz, DMSO-d$_6$): δ [ppm]=3.32-3.51 (m, 2H), 3.83 (dd, 1H), 3.96 (br. d, 1H), 4.25-4.46 (m, 3H), 5.11 (q, 1H), 6.90 (d, 1H), 7.53-7.71 (m, 6H), 7.75 (d, 2H), 8.11 (s, 1H), 8.23 (br. t, 1H), 8.65 (d, 1H).

Example 37

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(methylsulphonyl)amino]-2-[3-(trifluoromethyl)phenyl]ethyl}acetamide (Diastereomer Mixture)

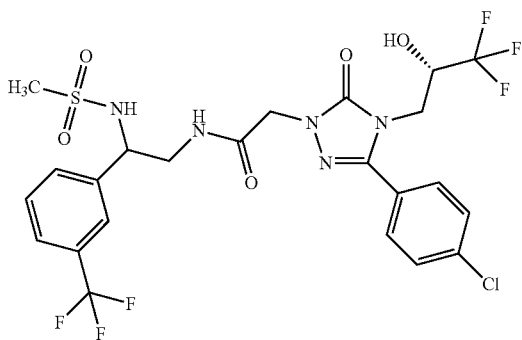 [SMILES: CS(=O)(=O)NC(CNC(=O)Cn1nc(-c2ccc(Cl)cc2)n(C[C@H](O)C(F)(F)F)c1=O)c1cccc(C(F)(F)F)c1]

4 μl (56 μmol) of methanesulphonyl chloride were added to a solution of 30 mg (51 μmol) of the compound of Example 58A in 0.5 ml of pyridine, and the mixture was stirred at RT overnight. Since HPLC analysis showed a lot of remaining starting material, further equivalents of methane-sulphonyl chloride (3.1 eq. in total) were added a little at a time until complete conversion had been achieved. 100 μl each of water and methanol were then added. After 5 min of stirring, the reaction mixture was diluted with about 3 ml of DMSO and separated by preparative HPLC [Method 8]. The product-containing fraction was freed from the solvent on a rotary evaporator and the residue was dried under high vacuum. This gave 22 mg (68% of theory) of the title compound.

LC/MS [Method 4]: $R_t$=1.08 min; MS [ESIpos]: m/z=630 (M+H)$^+$ $^1$H NMR (400 MHz, DMSO-d$_6$): δ [ppm]=2.79 (s, 3H), 3.34-3.44 (m, 2H), 3.84 (dd, 1H), 3.97 (2 dd, tog. 1H), 4.23-4.34 (m, 1H), 4.34-4.47 (m, 2H), 4.57 (q, 1H), 6.92 (d, 1H), 7.55-7.69 (m, 5H), 7.72-7.78 (m, 3H), 7.92 (d, 1H), 8.28 (2 t, tog. 1H).

Example 38

N-{2-Acetamido-2-[3-(trifluoromethyl)phenyl]propyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 1)

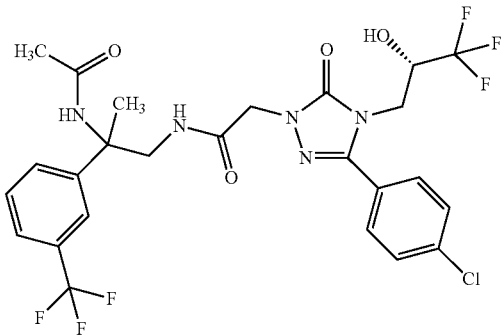 [SMILES: CC(=O)NC(C)(CNC(=O)Cn1nc(-c2ccc(Cl)cc2)n(C[C@H](O)C(F)(F)F)c1=O)c1cccc(C(F)(F)F)c1]

At RT, 12 μl (68 μmol) of N,N-diisopropylethylamine and then 6 μl (62 μmol) of acetic anhydride were added to a solution of 38 mg (62 μmol) of the compound of Example 53A in 0.96 ml of dichloromethane, and the mixture was stirred for 1 h. The volatile components were then removed on a rotary evaporator. Since LC/MS analysis of the crude product indicated additional formation of an O-acetylated byproduct, the residue was dissolved in 2 ml of methanol and 800 μl of 2 N aqueous sodium hydroxide solution were added. After 72 h, the mixture was acidified with 1 N hydrochloric acid and separated by preparative HPLC [Method 8]. In this step, the two product diastereomers were obtained in separated form. This gave 6 mg (16% of theory) of the title compound (Diastereomer 1) and 7 mg (19% of theory) of the second diastereomer (see Example 39).

LC/MS [Method 3]: $R_t$=1.26 min; MS [ESIpos]: m/z=608 (M+H)$^+$ $^1$H NMR (400 MHz, DMSO-d$_6$): δ [ppm]=1.50 (s, 3H), 1.84 (s, 3H), 3.57-3.72 (m, 2H), 3.82 (dd, 1H), 3.96 (dd, 1H), 4.21-4.34 (m, 1H), 4.45 (m [AB], 2H), 6.91 (d, 1H), 7.49-7.66 (m, 6H), 7.69-7.75 (m, 2H), 8.12 (s, 1H), 8.16 (t, 1H).

Example 39

N-{2-Acetamido-2-[3-(trifluoromethyl)phenyl]propyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (Diastereomer 2)

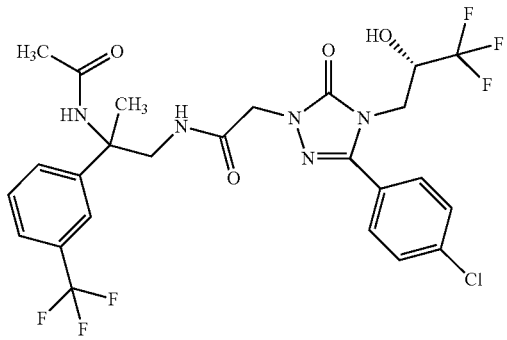 [SMILES: CC(=O)NC(C)(CNC(=O)Cn1nc(-c2ccc(Cl)cc2)n(C[C@H](O)C(F)(F)F)c1=O)c1cccc(C(F)(F)F)c1]

Second diastereomer (7 mg, 19% of theory) isolated from the reaction of the compound of Example 53A with acetic anhydride (see under Example 38).

LC/MS [Method 3]: $R_t$=1.27 min; MS [ESIpos]: m/z=608 (M+H)$^+$ $^1$H NMR (400 MHz, DMSO-d$_6$): δ [ppm]=1.50 (s, 3H), 1.85 (s, 3H), 3.65 (br. d, 2H), 3.82 (dd, 1H), 3.96 (dd, 1H), 4.22-4.35 (m, 1H), 4.40-4.53 (m [AB], 2H), 6.91 (d, 1H), 7.49-7.66 (m, 6H), 7.69-7.77 (m, 2H), 8.12 (s, 1H), 8.15 (t, 1H).

Example 40

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-formamido-2-[3-(trifluoromethyl)phenyl]propyl}acetamide (Diastereomer Mixture)

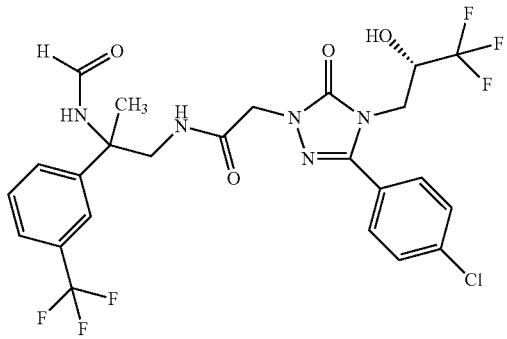 [SMILES: CC(CNC(=O)Cn1nc(-c2ccc(Cl)cc2)n(C[C@H](O)C(F)(F)F)c1=O)(NC=O)c1cccc(C(F)(F)F)c1]

At RT, 12 µl (68 µmol) of N,N-diisopropylethylamine and then 11 mg (65 µmol) of 4-nitrophenyl formate were added to a solution of 38 mg (62 µmol) of the compound of Example 53A in 1 ml of THF, and the mixture was stirred at RT. After 1 h, another 10 mg (62 µmol) of 4-nitrophenyl formate were added and stirring of the reaction mixture was continued overnight. Since LC/MS analysis indicated additional formation of an O-formylated byproduct, 248 µl of a 1 N solution of lithium hydroxide in water were added to the reaction mixture. After 1 h, the mixture was acidified with 1 N hydrochloric acid and separated by preparative HPLC [Method 8]. This gave 30 mg (81% of theory) of the title compound as a diastereomer mixture.

LC/MS [Method 4]: $R_t$=1.07 min; MS [ESIpos]: m/z=594 (M+H)$^+$ $^1$H NMR (400 MHz, DMSO-$d_6$): δ [ppm]=1.56 (s, 3H), 3.58-3.72 (m, 2H), 3.82 (dd, 1H), 3.96 (dd, 1H), 4.22-4.36 (m, 1H), 4.38-4.53 (m, 2H), 6.91 (d, 1H), 7.52-7.67 (m, 6H), 7.68-7.78 (m, 2H), 8.03 (br. s, 1H), 8.15-8.25 (m, 1H), 8.36 (br. d, 1H).

Example 41

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-[2-(trifluoromethyl)phenyl]ethylcarbamate (Diastereomer Mixture)

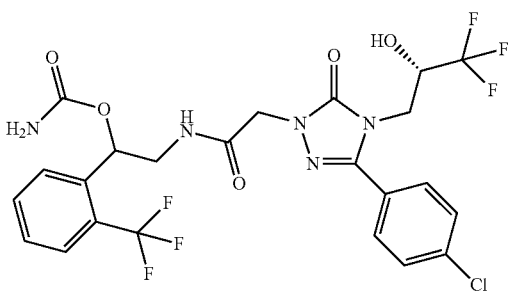 [SMILES: NC(=O)OC(CNC(=O)Cn1nc(-c2ccc(Cl)cc2)n(C[C@H](O)C(F)(F)F)c1=O)c1ccccc1C(F)(F)F]

371 mg (1.02 mmol) of the compound of Example 8A, 292 mg (1.52 mmol) of EDC and 206 mg (1.52 mmol) of HOBt in 10 ml of DMF were stirred at RT for 5 min. The resulting solution was then added dropwise to a solution of 280 mg (90% pure, 1.02 mmol) of the compound of Example 37A in 40 ml of acetonitrile. After 30 min at RT, acetonitrile was removed on a rotary evaporator. 1 ml of 1 M hydrochloric acid was added to the remaining solution, and the mixture was separated directly into its components by preparative HPLC [Method 8]. The product fraction was freed from the solvent on a rotary evaporator and the residue was dried under high vacuum. This gave 481 mg (80% of theory) of the title compound as a diastereomer mixture.

LC/MS [Method 4]: $R_t$=1.03 min; MS [ESIpos]: m/z=596 (M+H)$^+$.

By preparative HPLC on a chiral phase [Method 15a], it was possible to separate the two diastereomers, see Example 42 and Example 43.

Example 42

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-[2-(trifluoromethyl)phenyl]ethyl carbamate (Diastereomer 1)

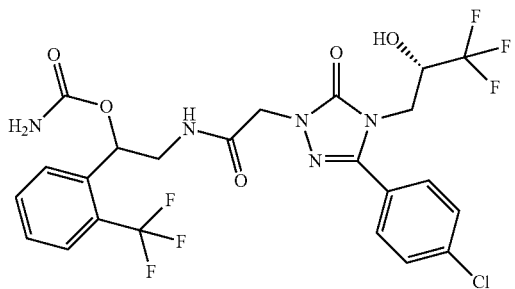 [SMILES: NC(=O)OC(CNC(=O)Cn1nc(-c2ccc(Cl)cc2)n(C[C@H](O)C(F)(F)F)c1=O)c1ccccc1C(F)(F)F]

First-eluting diastereomer from the chromatographic separation of 480 mg of the compound of Example 41 according to Method 15a. The material obtained in this manner (254 mg) was once again subjected to fine purification by preparative HPLC [Method 8]. This gave 220 mg of the pure title compound.

Chiral analytical HPLC [Method 16]: $R_t$=2.26 min.
LC/MS [Method 4]: $R_t$=1.03 min; MS [ESIpos]: m/z=596 (M+H)$^+$ $^1$H NMR (400 MHz, DMSO-$d_6$): δ [ppm]=3.40-3.52 (m, 2H), 3.83 (dd, 1H), 3.96 (dd, 1H), 4.23-4.34 (m, 1H), 4.34-4.47 (m [AB], 2H), 5.66 (t, 1H), 6.53-6.90 (br. d, 2H), 6.93 (d, 1H), 7.55-7.71 (m, 6H), 7.76 (d, 2H), 8.35 (t, 1H).

Example 43

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-[2-(trifluoromethyl)phenyl]ethyl carbamate (Diastereomer 2)

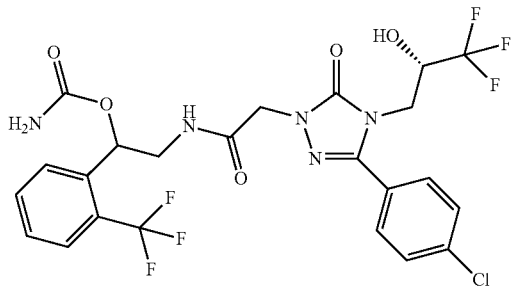 [SMILES: NC(=O)OC(CNC(=O)Cn1nc(-c2ccc(Cl)cc2)n(C[C@H](O)C(F)(F)F)c1=O)c1ccccc1C(F)(F)F]

Last-eluting diastereomer from the chromatographic separation of 480 mg of the compound of Example 41 according to Method 15a. The material obtained in this manner (258 mg) was once again subjected to fine purification by preparative HPLC [Method 8]. This gave 220 mg of the pure title compound.

Chiral analytical HPLC [Method 16]: $R_t$=4.33 min.
LC/MS [Method 4]: $R_t$=1.03 min; MS [ESIpos]: m/z=596 (M+H)$^+$ ¹H NMR (400 MHz, DMSO-d₆): δ [ppm]=3.39-3.53 (m, 2H), 3.83 (dd, 1H), 3.96 (dd, 1H), 4.23-4.35 (m, 1H), 4.40 (s, 2H), 5.66 (t, 1H), 6.51-6.90 (br. d, 2H), 6.92 (d, 1H), 7.58-7.71 (m, 6H), 7.76 (d, 2H), 8.35 (t, 1H).

Example 44

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-[3-(trifluoromethyl)phenyl]ethyl carbamate (Diastereomer Mixture)

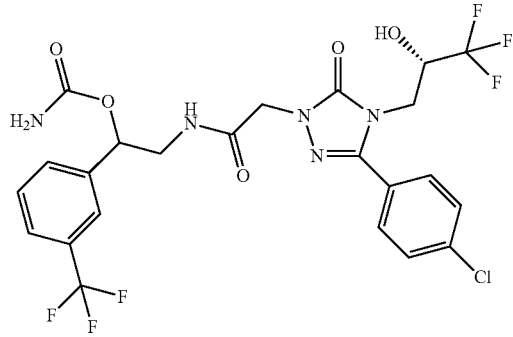 [SMILES: NC(=O)OC(CNC(=O)Cn1nc(-c2ccc(Cl)cc2)n(C[C@H](O)C(F)(F)F)c1=O)c1cccc(C(F)(F)F)c1]

78 mg (0.21 mmol) of the compound of Example 8A, 73 mg (0.26 mmol) of the compound of Example 39A, 43 mg (0.26 mmol) of EDC, 36 mg (0.26 mmol) of HOBt and 56 µl (0.32 mmol) of N,N-diisopropylethylamine in 2 ml of DMF were stirred at RT for 30 min. 1 ml of 1 M hydrochloric acid was then added to the solution, and the mixture was separated directly into its components by preparative HPLC [Method 8]. The product fraction was freed from the solvent on a rotary evaporator and the residue was dried under high vacuum. This gave 95 mg (75% of theory) of the title compound as a diastereomer mixture.

LC/MS [Method 4]: $R_t$=1.05 min; MS [ESIpos]: m/z=596 (M+H)⁺.

By preparative HPLC on a chiral phase [Method 15a], it was possible to separate the two diastereomers, see Example 45 and Example 46.

Example 45

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-[3-(trifluoromethyl)phenyl]ethyl carbamate (Diastereomer 1)

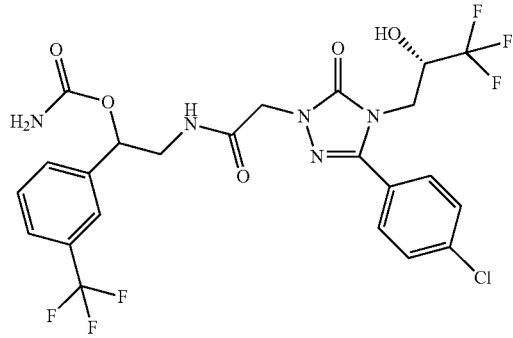 [SMILES: NC(=O)OC(CNC(=O)Cn1nc(-c2ccc(Cl)cc2)n(C[C@H](O)C(F)(F)F)c1=O)c1cccc(C(F)(F)F)c1]

First-eluting diastereomer from the chromatographic separation of 95 mg of the compound of Example 44 according to Method 15a. The material obtained in this manner (44 mg) was once again subjected to fine purification by preparative HPLC [Method 8]. This gave 33 mg of the pure title compound.

Chiral analytical HPLC [Method 16]: $R_t$=2.27 min.
LC/MS [Method 2]: $R_t$=2.27 min; MS [ESIpos]: m/z=596 (M+H)⁺

¹H NMR (400 MHz, DMSO-d₆): δ [ppm]=3.39-3.53 (m, 2H), 3.83 (dd, 1H), 3.96 (dd, 1H), 4.23-4.36 (m, 1H), 4.40 (s, 2H), 5.66 (t, 1H), 6.56-6.89 (br. d, 2H), 6.92 (d, 1H), 7.57-7.71 (m, 6H), 7.72-7.79 (m, 2H), 8.34 (t, 1H).

Example 46

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-[3-(trifluoromethyl)phenyl]ethyl carbamate (Diastereomer 2)

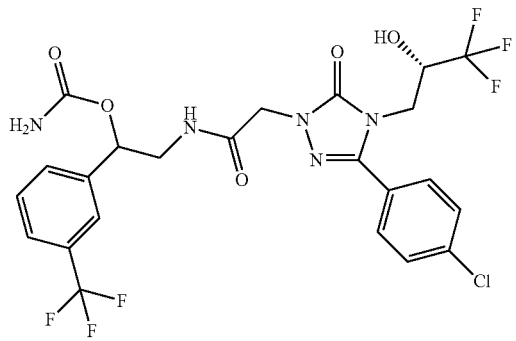 [SMILES: NC(=O)OC(CNC(=O)Cn1nc(-c2ccc(Cl)cc2)n(C[C@H](O)C(F)(F)F)c1=O)c1cccc(C(F)(F)F)c1]

Last-eluting diastereomer from the chromatographic separation of 95 mg of the compound of Example 44 according to Method 15a. The material obtained in this manner (44 mg) was once again subjected to fine purification by preparative HPLC [Method 8]. This gave 35 mg of the pure title compound.

Chiral analytical HPLC [Method 16]: $R_t$=4.33 min.
LC/MS [Method 3]: $R_t$=1.21 min; MS [ESIpos]: m/z=596 (M+H)⁺

¹H NMR (400 MHz, DMSO-d₆): δ [ppm]=3.40-3.52 (m, 2H), 3.83 (dd, 1H), 3.96 (dd, 1H), 4.23-4.35 (m, 1H), 4.33-4.48 (m [AB], 2H), 5.66 (t, 1H), 6.55-6.88 (br. d, 2H), 6.92 (d, 1H), 7.57-7.71 (m, 6H), 7.73-7.79 (m, 2H), 8.34 (t, 1H).

Example 47

1-(2-Chlorophenyl)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]ethyl carbamate (Diastereomer Mixture)

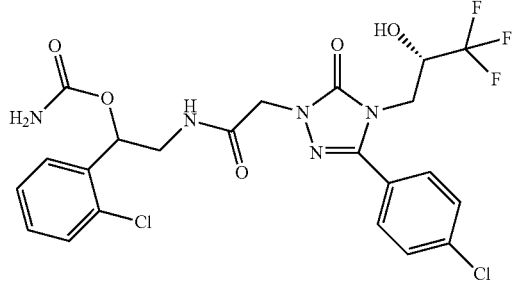 [SMILES: NC(=O)OC(CNC(=O)Cn1nc(-c2ccc(Cl)cc2)n(C[C@H](O)C(F)(F)F)c1=O)c1ccccc1Cl]

78 mg (0.21 mmol) of the compound of Example 8A, 61 mg (0.32 mmol) of EDC and 46 mg (0.32 mmol) of HOBt in 2 ml of DMF were stirred at RT for 20 min. The resulting solution was then added dropwise to a solution of 46 mg (0.21 mmol) of the compound of Example 40A in 8 ml of acetonitrile. After 30 min at RT, the acetonitrile was removed on a rotary evaporator. 1 ml of 1 M hydrochloric acid was added to the remaining solution, and the mixture was separated directly into its components by preparative HPLC [Method 8]. The product fraction was freed from the solvent on a rotary evaporator and the residue was dried under high vacuum. This gave 59 mg (49% of theory) of the title compound as a diastereomer mixture.

LC/MS [Method 2]: $R_t$=2.10 min; MS [ESIpos]: m/z=562 $(M+H)^+$.

By preparative HPLC on a chiral phase [Method 15a], it was possible to separate the two diastereomers, see Example 48 and Example 49.

Example 48

1-(2-Chlorophenyl)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]ethyl carbamate (Diastereomer 1)

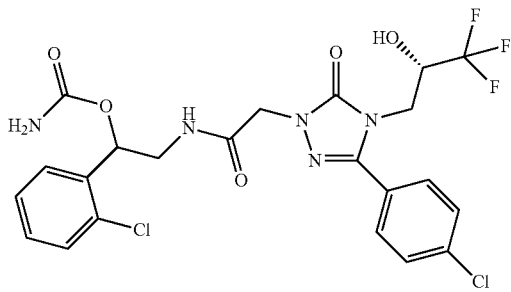 [SMILES: NC(=O)OC(CNC(=O)Cn1nc(-c2ccc(Cl)cc2)n(C[C@H](O)C(F)(F)F)c1=O)c1ccccc1Cl]

First-eluting diastereomer from the chromatographic separation of 59 mg of the compound of Example 47 according to Method 15a. The material obtained in this manner (28 mg) was once again subjected to fine purification by preparative HPLC [Method 8]. This gave 22 mg of the pure title compound.

Chiral analytical HPLC [Method 16]: $R_t$=2.75 min.
LC/MS [Method 3]: $R_t$=1.13 min; MS [ESIpos]: m/z=562 $(M+H)^+$ $^1$H NMR (400 MHz, DMSO-$d_6$): δ [ppm]=3.35-3.50 (m, 2H), 3.83 (dd, 1H), 3.96 (dd, 1H), 4.23-4.36 (m, 1H), 4.42 (s, 2H), 5.90 (dd, 1H), 6.53-6.89 (br. d, 2H), 6.93 (d, 1H), 7.31-7.42 (m, 2H), 7.42-7.48 (m, 2H), 7.63 (d, 2H), 7.76 (d, 2H), 8.38 (t, 1H).

Example 49

1-(2-Chlorophenyl)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]ethyl carbamate (Diastereomer 2)

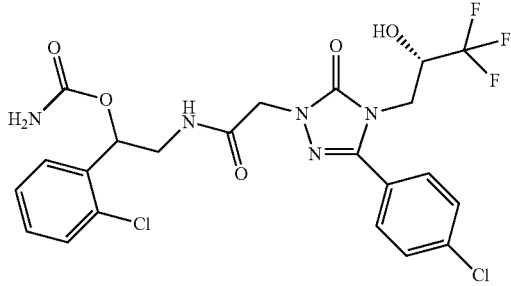 [SMILES: NC(=O)OC(CNC(=O)Cn1nc(-c2ccc(Cl)cc2)n(C[C@H](O)C(F)(F)F)c1=O)c1ccccc1Cl]

Last-eluting diastereomer from the chromatographic separation of 59 mg of the compound of Example 47 according to Method 15a. The material obtained in this manner (30 mg) was once again subjected to fine purification by preparative HPLC [Method 8]. This gave 19 mg of the pure title compound.

Chiral analytical HPLC [Method 16]: $R_t$=5.11 min.
LC/MS [Method 4]: $R_t$=0.98 min; MS [ESIpos]: m/z=562 $(M+H)^+$ $^1$H NMR (400 MHz, DMSO-$d_6$): δ [ppm]=3.33-3.42 (m, 1H), 3.43-3.53 (m, 1H), 3.83 (dd, 1H), 3.97 (dd, 1H), 4.23-4.35 (m, 1H), 4.35-4.49 (m [AB], 2H), 5.90 (dd, 1H), 6.53-6.87 (br. s, 2H), 6.93 (d, 1H), 7.30-7.42 (m, 2H), 7.42-7.48 (m, 2H), 7.63 (d, 2H), 7.76 (d, 2H), 8.38 (t, 1H).

Example 50

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-(2,3-dichlorophenyl)ethyl carbamate (Diastereomer Mixture)

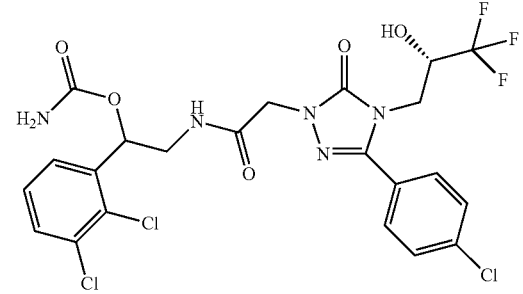 [SMILES: NC(=O)OC(CNC(=O)Cn1nc(-c2ccc(Cl)cc2)n(C[C@H](O)C(F)(F)F)c1=O)c1cccc(Cl)c1Cl]

73 mg (0.20 mmol) of the compound of Example 8A, 60 mg (0.24 mmol) of the compound of Example 44A, 46 mg (0.24 mmol) of EDC and 34 mg (0.24 mmol) of HOBt in 2 ml of DMF were stirred at RT overnight. 1 ml of 1 M hydrochloric acid was then added to the solution, and the mixture was separated directly into its components by preparative HPLC [Method 8]. The product fraction was freed from the solvent on a rotary evaporator and the residue was dried under high vacuum. This gave 100 mg (83% of theory) of the title compound as a diastereomer mixture.

LC/MS [Method 4]: $R_t$=1.03 min; MS [ESIpos]: m/z=596 $(M+H)^+$.

By preparative HPLC on a chiral phase [Method 15a], it was possible to separate the two diastereomers, see Example 51 and Example 52.

Example 51

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-(2,3-dichlorophenyl)ethyl carbamate (Diastereomer 1)

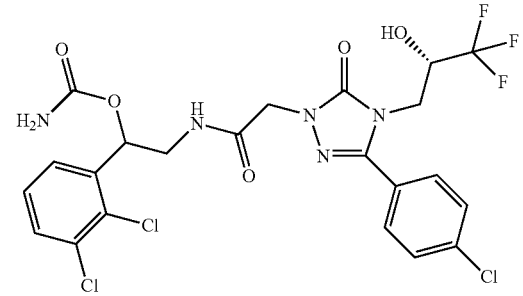 [SMILES: NC(=O)OC(CNC(=O)Cn1nc(-c2ccc(Cl)cc2)n(C[C@H](O)C(F)(F)F)c1=O)c1cccc(Cl)c1Cl]

First-eluting diastereomer from the chromatographic separation of 100 mg of the compound of Example 50 according to Method 15a. The material obtained in this manner (47 mg) was once again subjected to fine purification by preparative HPLC [Method 8]. This gave 32 mg of the pure title compound.

Chiral analytical HPLC [Method 16]: $R_t$=3.20 min.
LC/MS [Method 4]: $R_t$=1.03 min; MS [ESIpos]: m/z=596 $(M+H)^+$
$^1$H NMR (400 MHz, DMSO-$d_6$): δ [ppm]=3.44 (t, 2H), 3.83 (dd, 1H), 3.96 (dd, 1H), 4.22-4.35 (m, 1H), 4.41 (s, 2H), 5.91 (t, 1H), 6.59-6.89 (br. d, 2H), 6.93 (d, 1H), 7.38-7.44 (m, 2H), 7.58-7.67 (m, 3H), 7.76 (d, 2H), 8.39 (t, 1H).

Example 52

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-1-(2,3-dichlorophenyl)ethyl carbamate (Diastereomer 2)

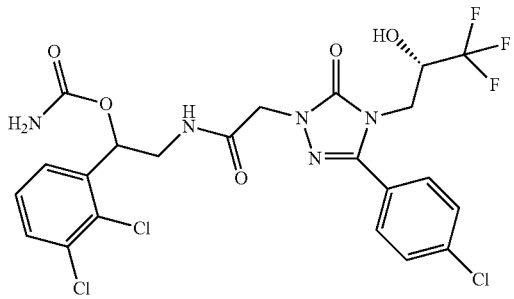 [SMILES: NC(=O)OC(CNC(=O)Cn1nc(-c2ccc(Cl)cc2)n(C[C@H](O)C(F)(F)F)c1=O)c1cccc(Cl)c1Cl]

Last-eluting diastereomer from the chromatographic separation of 100 mg of the compound of Example 50 according to Method 15a. The material obtained in this manner (50 mg) was once again subjected to fine purification by preparative HPLC [Method 8]. This gave 39 mg of the pure title compound.

Chiral analytical HPLC [Method 16]: $R_t$=6.05 min.
LC/MS [Method 4]: $R_t$=1.03 min; MS [ESIpos]: m/z=596 $(M+H)^+$
$^1$H NMR (400 MHz, DMSO-$d_6$): δ [ppm]=3.37-3.52 (m, 2H), 3.83 (dd, 1H), 3.96 (dd, 1H), 4.23-4.34 (m, 1H), 4.35-4.48 (m [AB], 2H), 5.90 (dd, 1H), 6.59-6.88 (br. d, 2H), 6.93 (d, 1H), 7.38-7.45 (m, 2H), 7.57-7.67 (m, 3H), 7.76 (d, 2H), 8.39 (t, 1H).

Example 53

2-{3-(4-Chlorophenyl)-5-oxo-4-[(2S)-3,3,3-trifluoro-2-hydroxypropyl]-4,5-dihydro-1H-1,2,4-triazol-1-yl}-N-{(2R)-1-hydroxy-3-[3-(trifluoromethyl)phenyl]propan-2-yl}acetamide

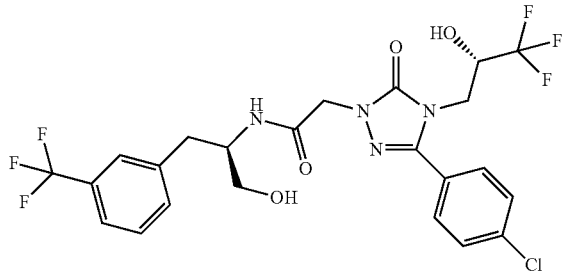 [SMILES: O=C(Cn1nc(-c2ccc(Cl)cc2)n(C[C@H](O)C(F)(F)F)c1=O)N[C@@H](CO)Cc1cccc(C(F)(F)F)c1]

48 μl of N,N-diisopropylethylamine were added to a mixture of 50 mg (137 μmol) of the compound of Example 8A, 42 mg (164 μmol) of the compound of Example 45A, 39 mg (205 μmol) of EDC and 28 mg (205 μmol) of HOBt in 1.36 ml of DMF. The resulting mixture was stirred at RT overnight and then separated directly into its components by preparative HPLC [Method 9]. This gave 61 mg (79% of theory) of the title compound.

LC/MS [Method 1]: $R_t$=2.01 min; MS [ESIpos]: m/z=567 $(M+H)^+$
$^1$H NMR (400 MHz, DMSO-$d_6$): δ [ppm]=2.75 (dd, 1H), 2.96 (dd, 1H), 3.37 (dq, 2H), 3.83 (dd, 1H), 3.87-4.00 (m, 2H), 4.21-4.32 (m, 1H), 4.31 (d, 1H), 4.43 (s, 1H), 4.90 (t, 1H), 6.90 (d, 1H), 7.45-7.59 (m, 4H), 7.63 (d, 2H), 7.74 (d, 2H), 8.12 (d, 1H).

Example 54

2-{3-(4-Chlorophenyl)-5-oxo-4-[(2S)-3,3,3-trifluoro-2-hydroxypropyl]-4,5-dihydro-1H-1,2,4-triazol-1-yl}-N-{(2S)-1-hydroxy-3-[3-(trifluoromethyl)phenyl]propan-2-yl}acetamide

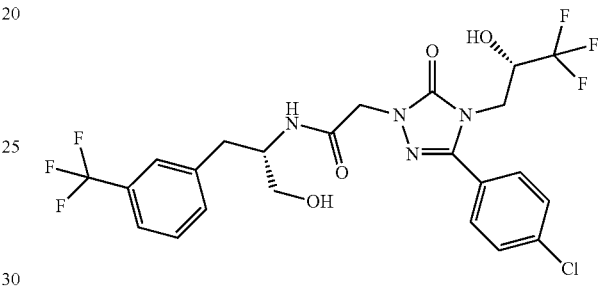

Analogously to Example 53, 50 mg (137 μmol) of the compound of Example 8A and 42 mg (164 μmol) of the compound of Example 46A gave 53 mg (68% of theory) of the title compound.

LC/MS [Method 3]: $R_t$=1.26 min; MS [ESIpos]: m/z=567 $(M+H)^+$
$^1$H NMR (400 MHz, DMSO-$d_6$): δ [ppm]=2.75 (dd, 1H), 2.95 (dd, 1H), 3.38 (dq, 2H), 3.82 (dd, 1H), 3.87-4.00 (m, 2H), 4.22-4.33 (m, 1H), 4.30-4.43 (m, 2H), 4.91 (t, 1H), 6.91 (d, 1H), 7.44-7.59 (m, 4H), 7.60-7.66 (m, 2H), 7.74 (d, 2H), 8.11 (d, 1H).

Example 55

(2R)-2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propyl carbamate

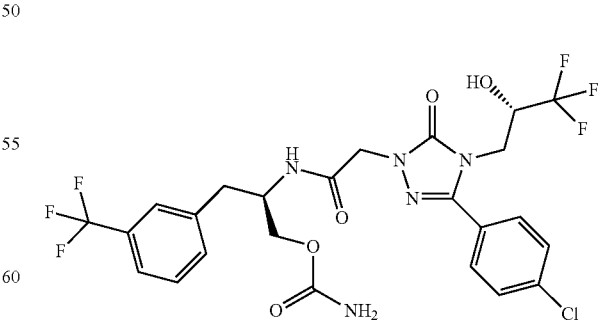

37 μl (210 μmol) of N,N-diisopropylethylamine were added to a mixture of 38 mg (105 μmol) of the compound of Example 8A, 42 mg (115 μmol) of the compound of Example 47A, 28 mg (147 μmol) of EDC and 21 mg (147 μmol) of HOBt in 1.39 ml of DMF. The resulting mixture was stirred at RT for 2 h, 1 ml of 1 M hydrochloric acid was then added and the mixture was separated directly into its components by preparative HPLC [Method 9]. This gave 61 mg (79% of theory) of the title compound.

LC/MS [Method 1]: $R_t$=2.01 min; MS [ESIpos]: m/z=610 (M+H)$^+$ $^1$H NMR (400 MHz, DMSO-d$_6$): δ [ppm]=2.80 (dd, 1H), 2.93 (dd, 1H), 3.78-3.89 (m, 2H), 3.90-4.00 (m, 2H), 4.06-4.18 (m, 1H), 4.22-4.43 (m, 3H), 6.44-6.73 (br. s, 2H), 6.91 (d, 1H), 7.47-7.60 (m, 4H), 7.63 (d, 2H), 7.74 (d, 2H), 8.26 (d, 1H).

Example 56

(2S)-2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propyl carbamate

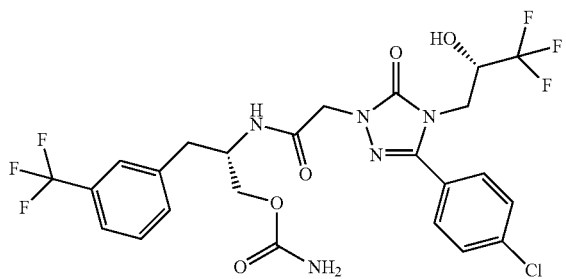 [SMILES: NC(=O)OC[C@H](Cc1cccc(C(F)(F)F)c1)NC(=O)Cn1nc(-c2ccc(Cl)cc2)n(C[C@H](O)C(F)(F)F)c1=O]

67 μl (383 μmol) of N,N-diisopropylethylamine were added to a mixture of 70 mg (191 μmol) of the compound of Example 8A, 79 mg (264 μmol) of the compound of Example 48A, 44 mg (230 μmol) of EDC and 33 mg (230 μmol) of HOBt in 3 ml of DMF. The resulting mixture was stirred at RT overnight, 1 ml of 1 M hydrochloric acid was then added and the mixture was separated directly into its components by preparative HPLC [Method 9]. This gave 64 mg (55% of theory) of the title compound.

LC/MS [Method 1]: $R_t$=2.03 min; MS [ESIpos]: m/z=610 (M+H)$^+$ $^1$H NMR (400 MHz, DMSO-d$_6$): δ [ppm]=2.80 (dd, 1H), 2.93 (dd, 1H), 3.78-3.89 (m, 2H), 3.90-4.00 (m, 2H), 4.06-4.18 (m, 1H), 4.22-4.32 (m, 1H), 4.35 (s, 2H), 6.42-6.72 (br. s, 2H), 6.91 (d, 1H), 7.46-7.59 (m, 4H), 7.60-7.66 (m, 2H), 7.72-7.77 (m, 2H), 8.25 (d, 1H).

Example 57

1-(2-Chlorophenyl)-2-({[3-(4-chlorophenyl)-4-(2-fluorobenzyl)-5-oxo-4,5-dihydro-1H-1,2,4-triazol-1-yl]acetyl}amino)ethyl carbamate (Racemate)

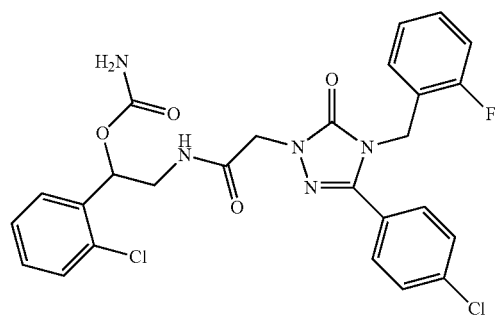 [SMILES: NC(=O)OC(CNC(=O)Cn1nc(-c2ccc(Cl)cc2)n(Cc2ccccc2F)c1=O)c1ccccc1Cl]

A mixture of 66 mg (182 μmol) of [3-(4-chlorophenyl)-4-(2-fluorobenzyl)-5-oxo-4,5-dihydro-1H-1,2,4-triazol-1-yl]acetic acid [for the preparation see Example 156A in WO 2007/134862], 47 mg (219 μmol) of the compound of Example 40A, 42 mg (219 μmol) of EDC and 35 mg (219 μmol) of HOBt in 4 ml of DMF was stirred at RT overnight, 1 ml of 1 M hydrochloric acid was then added and the mixture was separated directly into its components by preparative HPLC [Method 23]. This gave 64 mg (63% of theory) of the title compound.

LC/MS [Method 1]: $R_t$=1.25 min; MS [ESIpos]: m/z=558 (M+H)$^+$ $^1$H NMR (400 MHz, DMSO-d$_6$): δ [ppm]=3.36-3.51 (m, 2H), 4.40-4.52 (m [AB], 2H), 5.03 (br. s, 2H), 5.90 (dd, 1H), 6.55-6.91 (2 br. s, 2H), 7.04-7.19 (m, 3H), 7.27-7.42 (m, 3H), 7.42-7.48 (m, 2H), 7.54 (s, 4H), 8.43 (t, 1H).

Example 58

1-(2-Chlorophenyl)-2-[({3-(4-chlorophenyl)-5-oxo-4-[(1E)-3,3,3-trifluoroprop-1-en-1-yl]-4,5-dihydro-1H-1,2,4-triazol-1-yl}acetyl)amino]ethyl carbamate (Racemate)

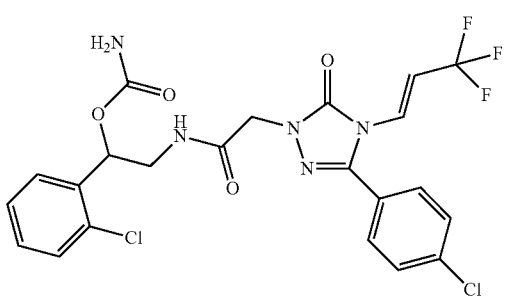 [SMILES: NC(=O)OC(CNC(=O)Cn1nc(-c2ccc(Cl)cc2)n(/C=C/C(F)(F)F)c1=O)c1ccccc1Cl]

A mixture of 128 mg (369 μmol) of the compound of Example 33A, 95 mg (443 μmol) of the compound of Example 40A, 85 mg (443 μmol) of EDC and 71 mg (443 μmol) of HOBt in 4 ml of DMF was stirred at RT overnight, 1 ml of 1 M hydrochloric acid was then added and the mixture was separated directly into its components by preparative HPLC [Method 23]. This gave 130 mg (65% of theory) of the title compound.

LC/MS [Method 3]: $R_t$=1.30 min; MS [ESIpos]: m/z=544 (M+H)$^+$ $^1$H NMR (400 MHz, DMSO-d$_6$): δ [ppm]=3.36-3.51 (m, 2H), 4.40-4.52 (m [AB], 2H), 5.91 (dd, 1H), 6.50-6.95 (2 br. s, 2H), 6.87 (dq, 1H), 7.18 (dq, 1H), 7.30-7.41 (m, 2H), 7.45 (d, 2H), 7.62-7.72 (m, 4H), 8.44 (t, 1H).

Example 59

1-(2-Chlorophenyl)-2-({[3-(4-chlorophenyl)-5-oxo-4-(3,3,3-trifluoropropyl)-4,5-dihydro-1H-1,2,4-triazol-1-yl]acetyl}amino)ethyl carbamate (Racemate)

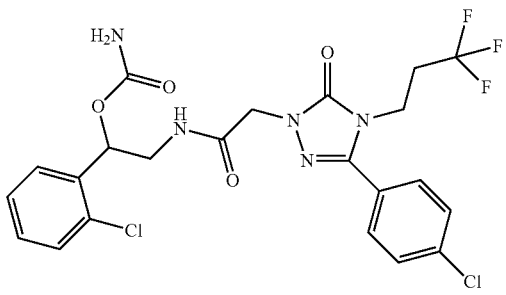 [SMILES: NC(=O)OC(CNC(=O)Cn1nc(-c2ccc(Cl)cc2)n(CCC(F)(F)F)c1=O)c1ccccc1Cl]

A solution of 50 mg (92 μmol) of the compound of Example 58 in 20 ml of methanol was hydrogenated in a continuous-flow hydrogenation apparatus fitted with a 5% Pt/C cartridge (H-Cube, from Thales Nano, Budapest, Model HC-2-SS) at a flow rate of 1 ml/min, a temperature of 60° C. and at standard pressure. After the reaction had ended, the solution was freed from the methanol on a rotary evaporator and the residue was purified by preparative HPLC [Method 23]. This gave 22 mg (44% of theory) of the title compound.

LC/MS [Method 3]: $R_t$=1.20 min; MS [ESIpos]: m/z=546 $(M+H)^+$ $^1$H NMR (400 MHz, DMSO-$d_6$): δ [ppm]=2.57-2.67 (m, 2H), 3.30-3.50 (m, 2H), 3.99 (t, 2H), 4.36-4.47 (m [AB], 2H), 5.89 (dd, 1H), 6.48-6.89 (2 br. s, 2H), 7.30-7.41 (m, 2H), 7.42-7.48 (m, 2H), 7.61-7.71 (m, 4H), 8.38 (t, 1H).

Example 60

2-({[3-(4-Chlorophenyl)-4-(2-fluorobenzyl)-5-oxo-4,5-dihydro-1H-1,2,4-triazol-1-yl]acetyl}-amino)-1-[2-(trifluoromethyl)phenyl]ethyl carbamate (Racemate)

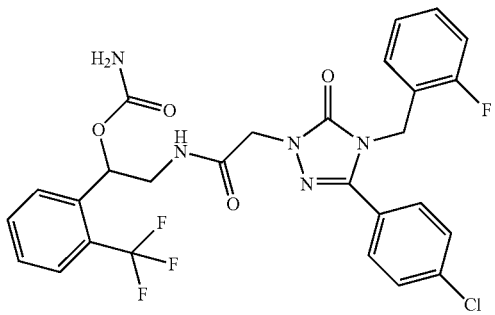 [SMILES: NC(=O)OC(CNC(=O)Cn1nc(-c2ccc(Cl)cc2)n(Cc2ccccc2F)c1=O)c1ccccc1C(F)(F)F]

A mixture of 40 mg (111 µmol) of [3-(4-chlorophenyl)-4-(2-fluorobenzyl)-5-oxo-4,5-dihydro-1H-1,2,4-triazol-1-yl]acetic acid [for the preparation see Example 156A in WO 2007/134862], 33 mg (133 µmol) of the compound of Example 37A, 25 mg (133 µmol) of EDC and 21 mg (133 µmol) of HOBt in 2.4 ml of DMF was stirred at RT overnight, 1 ml of 1 M hydrochloric acid was then added and the mixture was separated directly by preparative HPLC [Method 20] into its components. This gave 53 mg (81% of theory) of the title compound.

LC/MS [Method 4]: $R_t$=1.04 min; MS [ESIpos]: m/z=592 $(M+H)^+$ $^1$H NMR (400 MHz, DMSO-$d_6$): δ [ppm]=3.37-3.52 (m, 2H), 4.39-4.52 (m [AB], 2H), 5.03 (s, 2H), 5.92 (dd, 1H), 6.45-6.88 (2 br. s, 2H), 7.03-7.20 (m, 3H), 7.27-7.35 (m, 1H), 7.50-7.57 (m, 5H), 7.66-7.77 (m, 3H), 8.46 (t, 1H).

Example 61

2-[({3-(4-Chlorophenyl)-5-oxo-4-[(1E)-3,3,3-trifluoroprop-1-en-1-yl]-4,5-dihydro-1H-1,2,4-triazol-1-yl}acetyl)amino]-1-[2-(trifluoromethyl)phenyl]ethyl carbamate (Racemate)

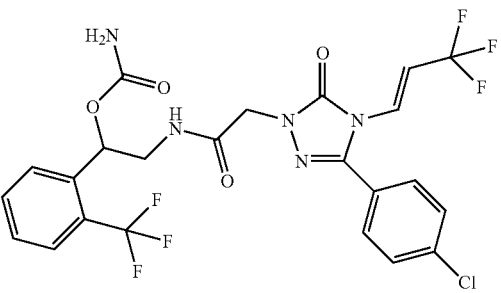 [SMILES: NC(=O)OC(CNC(=O)Cn1nc(-c2ccc(Cl)cc2)n(/C=C/C(F)(F)F)c1=O)c1ccccc1C(F)(F)F]

A mixture of 39 mg (111 µmol) of the compound of Example 33A, 33 mg (133 µmol) of the compound of 37A, 25 mg (133 µmol) of EDC and 21 mg (133 µmol) of HOBt in 1.2 ml of DMF was stirred at RT overnight, 1 ml of 1 M hydrochloric acid was then added and the mixture was separated directly into its components via preparative HPLC [Method 20]. This gave 52 mg (81% of theory) of the title compound.

LC/MS [Method 3]: $R_t$=1.34 min; MS [ESIpos]: m/z=578 $(M+H)^+$ $^1$H NMR (400 MHz, DMSO-$d_6$): δ [ppm]=3.36-3.51 (m, 2H), 4.40-4.51 (m [AB], 2H), 5.89-5.96 (m, 1H), 6.47-6.82 (br. s, 2H), 6.86 (dq, 1H), 7.18 (dq, 1H), 7.54 (br. t, 1H), 7.62-7.75 (m, 7H), 8.46 (t, 1H).

Example 62

2-({[3-(4-Chlorophenyl)-5-oxo-4-(3,3,3-trifluoropropyl)-4,5-dihydro-1H-1,2,4-triazol-1-yl]acetyl}-amino)-1-[2-(trifluoromethyl)phenyl]ethyl carbamate (Racemate)

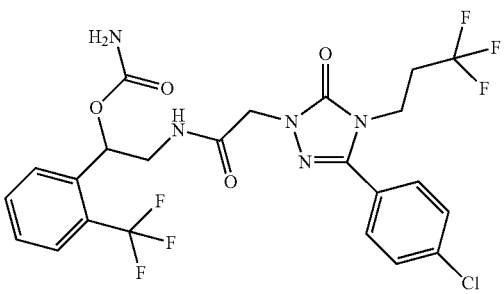 [SMILES: NC(=O)OC(CNC(=O)Cn1nc(-c2ccc(Cl)cc2)n(CCC(F)(F)F)c1=O)c1ccccc1C(F)(F)F]

A solution of 30 mg (52 µmol) of the compound of Example 61 in 15 ml of methanol was hydrogenated in a continuous-flow hydrogenation apparatus fitted with a 5% Pt/C cartridge (H-Cube, from Thales Nano, Budapest, Model HC-2-SS) at a flow rate of 1 ml/min, a temperature of 60° C. and at standard pressure. After the reaction had ended, the solution was freed from the methanol on a rotary evaporator and the residue was purified by preparative HPLC [Method 23]. This gave 15 mg (50% of theory) of the title compound.

LC/MS [Method 3]: $R_t$=1.24 min; MS [ESIpos]: m/z=580 $(M+H)^+$ $^1$H NMR (400 MHz, DMSO-$d_6$): δ [ppm]=2.57-2.67 (m, 2H), 3.36-3.50 (m, 2H), 3.98 (t, 2H), 4.34-4.47 (m [AB], 2H), 5.86-5.94 (m, 1H), 6.45-6.86 (br. s, 2H), 7.53 (br. t, 1H), 7.60-7.76 (m, 7H), 8.40 (t, 1H).

Example 63

2-(2-Chlorophenyl)-3-[({3-(4-chlorophenyl)-5-oxo-4-[(1E)-3,3,3-trifluoroprop-1-en-1-yl]-4,5-dihydro-1H-1,2,4-triazol-1-yl}acetyl)amino]propyl carbamate (Racemate)

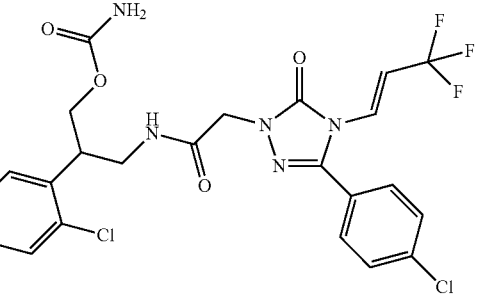

A mixture of 47 mg (135 µmol) of the compound of Example 33A, 34 mg (176 µmol) of EDC and 24 mg (176 µmol) of HOBt in 1 ml of DMF was stirred at RT for 1 h, and 34 mg (149 µmol) of the compound of Example 15A were then added. The mixture was stirred at RT for 16 h and then separated directly by preparative HPLC [Method 9] into its components. This gave 28 mg (37% of theory) of the title compound.

LC/MS [Method 3]: R$_t$=1.31 min; MS [ESIpos]: m/z=558 (M+H)$^+$ $^1$H NMR (400 MHz, DMSO-d$_6$): δ [ppm]=3.30-3.40 (m, 1H), 3.48 (dt, 1H), 3.66 (quin, 1H), 4.12-4.22 (m, 2H), 4.36-4.46 (m, 2H), 6.48 (br. s, 2H), 6.86 (dq, 1H), 7.13-7.21 (m, 1H), 7.23-7.34 (m, 2H), 7.39-7.46 (m, 2H), 7.60-7.71 (m, 4H), 8.24 (t, 1H).

Example 64

2-(2-Chlorophenyl)-3-({[3-(4-chlorophenyl)-4-(2-fluorobenzyl)-5-oxo-4,5-dihydro-1H-1,2,4-triazol-1-yl]acetyl}amino)propyl carbamate (Racemate)

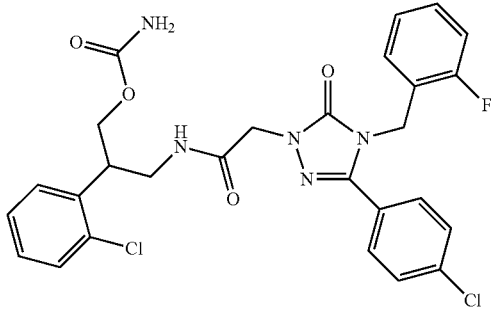 [SMILES: NC(=O)OCC(CNC(=O)Cn1nc(-c2ccc(Cl)cc2)n(Cc2ccccc2F)c1=O)c1ccccc1Cl]

Analogously to the procedure of Example 63, 49 mg (135 µmol) of [3-(4-chlorophenyl)-4-(2-fluorobenzyl)-5-oxo-4,5-dihydro-1H-1,2,4-triazol-1-yl]acetic acid [for the preparation see Example 156A in WO 2007/134862] were reacted with 34 mg (149 µmol) of the compound of Example 15A. This gave 27 mg (35% of theory) of the title compound.

LC/MS [Method 3]: R$_t$=1.26 min; MS [ESIpos]: m/z=572/574 (M+H)$^+$ $^1$H NMR (400 MHz, DMSO-d$_6$): δ [ppm]=3.31-3.41 (m, 1H), 3.45-3.55 (m, 1H), 3.66 (quin, 1H), 4.12-4.22 (m, 2H), 4.35-4.46 (m, 2H), 5.02 (s, 2H), 6.48 (br. s, 2H), 7.02-7.20 (m, 3H), 7.22-7.35 (m, 3H), 7.39-7.46 (m, 2H), 7.49-7.56 (m, 4H), 8.23 (t, 1H).

Example 65 tert-Butyl {2-({[3-(4-chlorophenyl)-4-cyclopropyl-5-oxo-4,5-dihydro-1H-1,2,4-triazol-1-yl]-acetyl}amino)-1-[2-(trifluoromethyl)phenyl]ethyl}carbamate (Racemate)

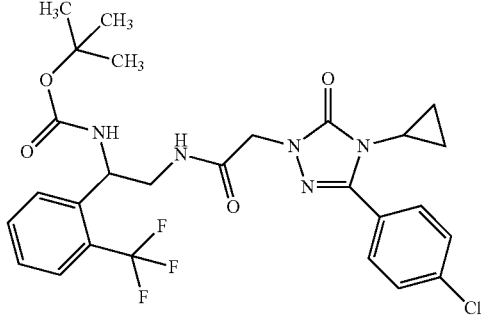 [SMILES: CC(C)(C)OC(=O)NC(CNC(=O)Cn1nc(-c2ccc(Cl)cc2)n(C2CC2)c1=O)c1ccccc1C(F)(F)F]

Analogously to the procedure of Example 63, 43 mg (146 µmol) of [3-(4-chlorophenyl)-4-cyclopropyl-5-oxo-4,5-dihydro-1H-1,2,4-triazol-1-yl]acetic acid [for the preparation see Example 88A in WO 2007/134862] were reacted with 49 mg (161 µmol) of tert-butyl {2-amino-1-[2-(trifluoromethyl)phenyl]ethyl}carbamate. This gave 59 mg (69% of theory) of the title compound.

LC/MS [Method 4]: R$_t$=1.14 min; MS [ESIpos]: m/z=580 (M+H)$^+$ $^1$H NMR (400 MHz, DMSO-d$_6$): δ [ppm]=0.54-0.61 (m, 2H), 0.87-0.94 (m, 2H), 1.33 (s, 9H), 3.18 (tt, 1H), 3.22-3.33 (m, 2H), 4.29-4.39 (m, 2H), 5.01 (br. s, 1H), 7.47 (q, 2H), 7.60 (d, 2H), 7.63-7.75 (m, 3H), 7.81 (d, 2H), 8.20 (m, 1H).

Example 66 tert-Butyl {2-({[3-(5-chloro-2-thienyl)-4-(2-methoxyethyl)-5-oxo-4,5-dihydro-1H-1,2,4-triazol-1-yl]acetyl}amino)-1-[2-(trifluoromethyl)phenyl]ethyl}carbamate (Racemate)

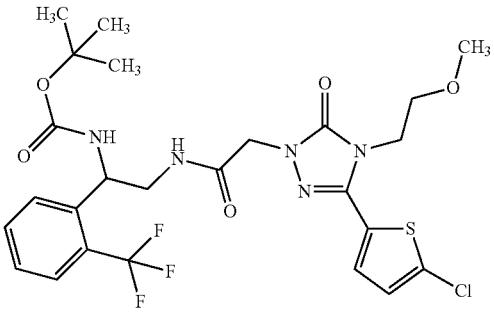 [SMILES: COCCn1c(-c2ccc(Cl)s2)nn(CC(=O)NCC(NC(=O)OC(C)(C)C)c2ccccc2C(F)(F)F)c1=O]

Analogously to the procedure of Example 63, 47 mg (146 µmol) of the compound of Example 52A were reacted with 49 mg (161 µmol) of tert-butyl {2-amino-1-[2-(trifluoromethyl)phenyl]-ethyl}carbamate. This gave 60 mg (68% of theory) of the title compound.

LC/MS [Method 4]: R$_t$=1.13 min; MS [ESIpos]: m/z=604 (M+H)$^+$ $^1$H NMR (400 MHz, DMSO-d$_6$): δ [ppm]=1.35 (s, 9H), 3.21 (s, 3H), 3.23-3.28 (m, 1H), 3.35-3.42 (m, 1H), 3.55 (t, 2H), 3.98 (t, 2H), 4.37 (s, 2H), 5.00 (br. s, 1H), 7.27 (d, 1H), 7.43-7.54 (m, 2H), 7.58 (d, 1H), 7.63-7.76 (m, 3H), 8.26 (m, 1H).

Example 67 tert-Butyl {2-({[3-(5-chloro-2-thienyl)-4-(2-fluorobenzyl)-5-oxo-4,5-dihydro-1H-1,2,4-triazol-1-yl]acetyl}amino)-1-[2-(trifluoromethyl)phenyl]ethyl}carbamate (Racemate)

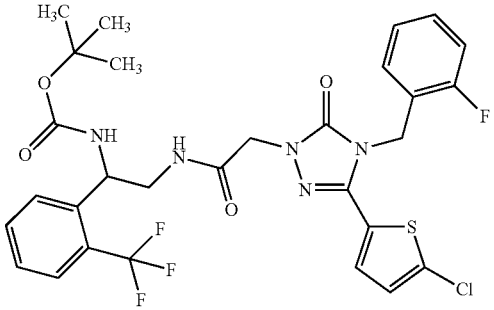 [SMILES: CC(C)(C)OC(=O)NC(CNC(=O)Cn1nc(-c2ccc(Cl)s2)n(Cc2ccccc2F)c1=O)c1ccccc1C(F)(F)F]

Analogously to the procedure of Example 63, 54 mg (146 µmol) of [3-(5-chloro-2-thienyl)-4-(2-fluorobenzyl)-5-oxo- 4,5-dihydro-1H-1,2,4-triazol-1-yl]acetic acid [for the preparation see Example 154A in WO 2007/134862] were reacted with 49 mg (161 μmol) of tert-butyl {2-amino-1-[2-(trifluoromethyl)phenyl]ethyl}carbamate. This gave 64 mg (67% of theory) of the title compound.

LC/MS [Method 3]: $R_t$=1.52 min; MS [ESIpos]: m/z=654 (M+H)$^+$ $^1$H NMR (400 MHz, DMSO-d$_6$): δ [ppm]=1.35 (s, 9H), 3.20-3.41 (m, 2H), 4.38-4.49 (m, 2H), 4.96-5.08 (m, 1H), 5.15 (s, 2H), 7.03-7.10 (m, 1H), 7.12-7.28 (m, 4H), 7.31-7.39 (m, 1H), 7.42-7.49 (m, 1H), 7.53 (d, 1H), 7.63-7.78 (m, 3H), 8.28-8.36 (m, 1H).

Example 68

2-[3-(4-Chlorophenyl)-4-cyclopropyl-5-oxo-4,5-dihydro-1H-1,2,4-triazol-1-yl]-N-{2-[(methyl-sulphonyl)amino]-2-[2-(trifluoromethyl)phenyl]ethyl}acetamide (Racemate)

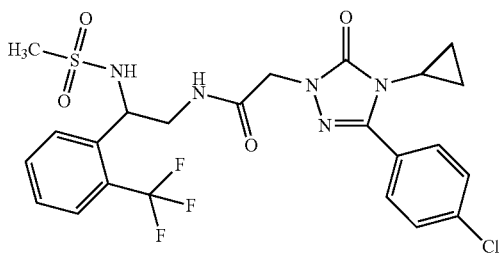 [SMILES: CS(=O)(=O)NC(CNC(=O)Cn1nc(-c2ccc(Cl)cc2)n(C2CC2)c1=O)c1ccccc1C(F)(F)F]

At RT, 4.1 μl of methanesulphonyl chloride were added to a solution of 29 mg (48 μmol) of the compound of Example 59A in 0.5 ml of pyridine. The mixture was stirred at RT for 1 h, and another 4.1 ml of methanesulphonyl chloride were added. The mixture was stirred at RT for another 18 h, and another 12.3 μl of methanesulphonyl chloride were added over a period of 3 h (265 μmol, 5.5 eq., in total). After 1 h, the volatile components were removed on a rotary evaporator. The residue was dissolved in a little DMSO and purified by preparative HPLC [Method 9]. This gave 17 mg (65% of theory) of the title compound.

LC/MS [Method 3]: $R_t$=1.19 min; MS [ESIpos]: m/z=558 (M+H)$^+$ $^1$H NMR (400 MHz, DMSO-d$_6$): δ [ppm]=0.53-0.64 (m, 2H), 0.87-0.95 (m, 2H), 2.70 (s, 3H), 3.18 (tt, 1H), 3.27-3.44 (m, 2H), 4.31-4.42 (m, 2H), 4.74-4.84 (m, 1H), 7.51 (t, 1H), 7.60 (d, 2H), 7.67-7.76 (m, 2H), 7.81 (d, 2H), 7.85 (d, 1H), 7.96 (d, 1H), 8.22 (t, 1H).

Example 69

2-[3-(5-Chloro-2-thienyl)-4-(2-methoxyethyl)-5-oxo-4,5-dihydro-1H-1,2,4-triazol-1-yl]-N-{2-[(methylsulphonyl)amino]-2-[2-(trifluoromethyl)phenyl]ethyl}acetamide (Racemate)

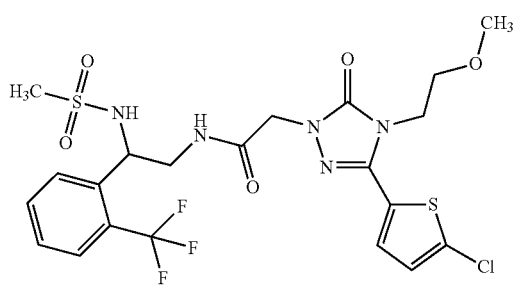 [SMILES: COCCn1c(-c2ccc(Cl)s2)nn(CC(=O)NCC(NS(C)(=O)=O)c2ccccc2C(F)(F)F)c1=O]

Analogously to the procedure of Example 68, 29 mg (46 μmol) of the compound of Example 60A were reacted with methanesulphonyl chloride. This gave 25 mg (92% of theory) of the title compound.

LC/MS [Method 3]: $R_t$=1.18 min; MS [ESIpos]: m/z=582 (M+H)$^+$ $^1$H NMR (400 MHz, DMSO-d$_6$): δ [ppm]=2.72 (s, 3H), 3.21 (s, 3H), 3.25-3.46 (m, 2H), 3.55 (t, 2H), 3.98 (t, 2H), 4.35-4.45 (m, 2H), 4.75-4.84 (m, 1H), 7.28 (d, 1H), 7.51 (t, 1H), 7.58 (d, 1H), 7.67-7.79 (m, 2H), 7.86 (d, 1H), 7.93-8.05 (m, 1H), 8.30 (t, 1H).

Example 70

2-[3-(5-Chloro-2-thienyl)-4-(2-fluorobenzyl)-5-oxo-4,5-dihydro-1H-1,2,4-triazol-1-yl]-N-{2-[(methyl-sulphonyl)amino]-2-[2-(trifluoromethyl)phenyl]ethyl}acetamide (Racemate)

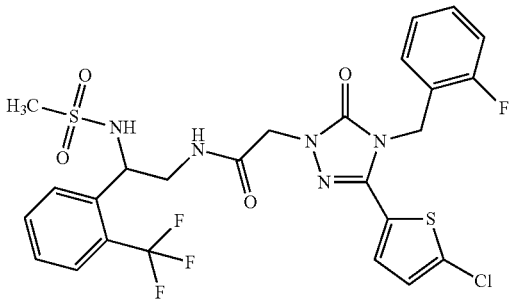 [SMILES: CS(=O)(=O)NC(CNC(=O)Cn1nc(-c2ccc(Cl)s2)n(Cc2ccccc2F)c1=O)c1ccccc1C(F)(F)F]

Analogously to the procedure of Example 68, 35 mg (52 μmol) of the compound of Example 61A were reacted with methanesulphonyl chloride. This gave 14 mg (41% of theory) of the title compound.

LC/MS [Method 3]: $R_t$=1.33 min; MS [ESIpos]: m/z=632 (M+H)$^+$ $^1$H NMR (400 MHz, DMSO-d$_6$): δ [ppm]=2.72 (s, 3H), 3.30-3.48 (m, 2H), 4.41-4.53 (m, 2H), 4.76-4.83 (m, 1H), 5.14 (s, 2H), 7.04-7.11 (m, 1H), 7.13-7.28 (m, 4H), 7.31-7.41 (m, 1H), 7.51 (t, 1H), 7.68-7.78 (m, 2H), 7.87 (d, 1H), 8.01 (m, 1H), 8.36 (t, 1H).

B. EVALUATION OF THE PHARMACOLOGICAL ACTIVITY

The pharmacological action of the compounds according to the invention can be shown in the following assays:
Abbreviations:
EDTA ethylenediaminetetraacetic acid
DMEM Dulbecco's Modified Eagle Medium
FCS foetal calf serum
HEPES 4-(2-hydroxyethyl)-1-piperazineethanesulphonic acid
SmGM Smooth Muscle Cell Growth Media
Tris-HCl 2-amino-2-(hydroxymethyl)-1,3-propanediol hydrochloride B-1. Cellular in vitro Assay for Determining the Vasopressin Receptor Activity The identification of agonists and antagonists of the V1a and V2 vasopressin receptors from humans and rats and also the quantification of the activity of the compounds of the invention takes place using recombinant cell lines. These cells derive originally from a hamster's ovary epithelial cell (Chinese Hamster Ovary, CHO K1, ATCC: American Type Culture Collection, Manassas, Va. 20108, USA). The test cell lines constitutively express a modified form of the calciumsensitive photoprotein aequorin, which, after reconstitution with the cofactor coelenterazine, emits light when there are increases in the free calcium concentrations [Rizzuto R, Simpson A W, Brini M, Pozzan T, *Nature* 358, 325-327 (1992)]. In addition, the cells are stably transfected with the human or rat V1a or V2 receptors. In the case of the Gs-coupling V2 receptors, the cells are stably transfected with a further gene, which codes for the promiscuous $G_{\alpha 16}$ protein [Amatruda T T, Steele D A, Slepak V Z, Simon M I, *Proceedings in the National Academy of Science USA* 88, 5587-5591 (1991)], either independently or as a fusion gene. The resulting vasopressin receptor test cells react to stimulation of the recombinantly expressed vasopressin receptors by intracellular release of calcium ions, which can be quantified by the resulting aequorin luminescence using a suitable luminometer [Milligan G, Marshall F, Rees S, *Trends in Pharmacological Sciences* 17, 235-237 (1996)].

Test Procedure:

On the day before the assay, the cells are plated out in culture medium (DMEM, 10% FCS, 2 mM glutamine, 10 mM HEPES) in 384-well microtitre plates and kept in a cell incubator (96% humidity, 5% v/v $CO_2$, 37° C.). On the day of the assay, the culture medium is replaced by a Tyrode solution (140 mM NaCl, 5 mM KCl, 1 mM $MgCl_2$, 2 mM $CaCl_2$, 20 mM glucose, 20 mM HEPES), which additionally contains the cofactor coelenterazine (50 µM), and the microtitre plate is then incubated for a further 3-4 hours. The test substances in various concentrations are placed for 10 to 20 minutes in the wells of the microtitre plate before the agonist [$Arg^8$]-vasopressin is added, and the resulting light signal is measured immediately in the luminometer. The $IC_{50}$ values are calculated using the GraphPad PRISM computer program (Version 3.02).

The table below lists representative $IC_{50}$ values for the compounds of the invention on the cell line transfected with the human V1a or V2 receptor:

TABLE

| Example No. | $IC_{50}$ hV1a [µM] | $IC_{50}$ hV2 [µM] |
|---|---|---|
| 2 | 0.001 | 0.016 |
| 6 | 0.012 | 0.001 |
| 9 | 0.063 | 0.005 |
| 10 | 0.024 | 0.009 |
| 13 | 0.004 | 0.070 |
| 19 | 0.013 | 0.011 |
| 25 | 0.008 | 0.005 |
| 33 | 0.017 | 0.008 |
| 36 | 0.019 | 0.013 |
| 39 | 0.025 | 0.010 |
| 42 | 0.008 | 0.003 |
| 47 | 0.005 | 0.002 |
| 52 | 0.007 | 0.002 |
| 53 | 0.004 | 0.015 |
| 57 | 0.010 | 0.022 |
| 59 | 0.014 | 0.048 |
| 66 | 0.051 | 1.2 |
| 67 | 0.018 | 0.30 |
| 69 | 0.13 | 3.5 |

B-2. Cellular in vitro Assay for Detecting the Action of Vasopressin V1a Receptor Antagonists on the Regulation of Profibrotic Genes The cell line H9C2 described as a cardiomyocyte type (American Type Culture Collection ATCC No. CRL-1446), isolated from rat cardiac tissue, endogenously expresses the vasopressin V1A receptor AVPR1A in high copy number, whereas the AVPR2 expression cannot be detected. For cell assays for the inhibition of the AVPR1A-dependent regulation of gene expression by receptor antagonists, the procedure is as follows:

H9C2 cells are seeded in 12-well microtitre plates for cell culture, at a cell density of 100 000 cells/well, in 1.0 ml of Opti-MEM medium (Invitrogen Corp., Carlsbad Calif., USA, Cat. No. 11058-021) with 2% FCS and 1% penicillin/streptomycin solution (Invitrogen, Cat. No. 10378-016), and held in a cell incubator (96% humidity, 5% v/v carbon dioxide, 37° C.). After 24 hours, sets of three wells (triplicate) are charged with vehicle solution (negative control), vasopressin solution ([$Arg^8$]-vasopressin acetate, Sigma, Cat. No. V9879) or test substance (dissolved in vehicle: water with 20% by volume ethanol) and vasopressin solution. In the cell culture, the final vasopressin concentration is 0.05 µM. The test substance solution is added to the cell culture in small volumes, and so a final concentration of 0.1% of ethanol in the cell assay is not exceeded. After an incubation time of 6 hours, the culture supernatant is drawn off under suction, the adherent cells are lysed in 250 µl of RLT buffer (Qiagen, Ratingen, Cat. No. 79216), and the RNA is isolated from this lysate using the RNeasy kit (Qiagen, Cat. No. 74104). This is followed by DNAse digestion (Invitrogen, Cat. No. 18068-015), cDNA synthesis (ImProm-II Reverse Transcription System, Promega, Cat. No. A3800) and RTPCR (pPCR MasterMix RT-QP2X-03-075 from Eurogentec, Seraing, Belgium). All procedures take place in accordance with the working protocols of the test reagents' manufacturers. The primer sets for the RTPCR are selected on the basis of the mRNA gene sequences (NCBI Genbank Entrez Nucleotide Data Base) using the Primer3Plus program with 6-FAM TAMRA-labelled probes. The RTPCR for determining the relative mRNA expression in the cells of the various assay batches is carried out using the Applied Biosystems ABI Prism 7700 Sequence Detector in 96-well or 384-well microtitre plate format in accordance with the instrument operating instructions. The relative gene expression is represented by the delta-delta Ct value [Applied Biosystems, User Bulletin No. 2 ABI Prism 7700 SDS Dec. 11, 1997 (updated October 2001)] with reference to the level of expression of the ribosomal protein L-32 gene (Genbank Acc. No. NM_013226) and the threshold Ct value of 35.

B-3. In vivo Assay for Detecting the Cardiovascular Effect: Blood Pressure Measurement on Anaesthetized Rats ('Vasopressin Challenge Model')

In male Sprague-Dawley rats (250-350 g body weight) under ketamine/xylazine/pentobarbital injection anaesthesia, polyethylene tubes (PE-50; Intramedic®), which are prefilled with heparin-containing (500 IU/ml) isotonic sodium chloride solution, are introduced into the jugular vein and the femoral vein and then tied in. Via one venous access, with the aid of a syringe, Arg-vasopressin is injected; the test substance is administered via the second venous access. For determination of the systolic blood pressure, a pressure catheter (Millar SPR-320 2F) is tied into the carotid artery. The arterial catheter is connected to a pressure transducer which feeds its signals to a recording computer equipped with suitable recording software. In a typical experiment the experimental animal is administered 3-4 successive bolus injections at intervals of 10-15 min with a defined amount of Arg-vasopressin (30 ng/kg) in isotonic sodium chloride solution and, when the blood pressure has reached initial levels again, the substance under test is administered as a bolus, with subsequent ongoing infusion, in a suitable solvent. After this, at defined intervals (10-15 min), the same amount of Arg-vasopressin as at the start is administered again. On the basis of the blood pressure values, a determination is made of the extent to which the test substance counteracts the hypertensive effect of the Arg-vasopressin. Control animals receive only solvent instead of the test substance.

Following intravenous administration, the compounds of the invention, in comparison to the solvent controls, bring about an inhibition in the blood pressure increase caused by Arg-vasopressin.

B-4. In vivo Assay for Detecting the Cardiovascular Effect: Diuresis Investigations on Conscious Rats in Metabolism Cages Wistar rats (300-450 g body weight) are kept with free access to feed (Altromin) and drinking water. During the experiment, the animals are kept with free access to drinking water for 4 to 8 hours individually in metabolism cages suitable for rats of this weight class (Tecniplast Deutschland GmbH, D-82383 Hohenpeißenberg). At the beginning of the experiment, the animals are administered the substance under test in a volume of 1 to 3 ml/kg body weight of a suitable solvent by means of a gavage into the stomach. Control animals receive only solvent. Controls and substance tests are carried out in parallel on the same day. Control groups and substance-dose groups each consist of 4 to 8 animals. During the experiment, the urine excreted by the animals is collected continuously in a receiver at the base of the cage. The volume of urine per unit time is determined separately for each animal, and the concentration of the sodium and potassium ions excreted in the urine is measured by standard methods of flame photometry. To obtain a sufficient volume of urine, the animals are given a defined amount of water by gavage at the beginning of the experiment (typically 10 ml per kilogram of body weight). Before the beginning of the experiment and after the end of the experiment, the body weight of the individual animals is determined.

Following oral administration, in comparison with solvent control applications, the compounds of the invention bring about an increased excretion of urine, which is based essentially on an increased excretion of water (aquaresis).

B-5. In vivo Assay for Detecting the Cardiovascular Effect: Haemodynamic Investigations on Anaesthetized Dogs Male or female mongrel dogs (Mongrels, Marshall BioResources, USA) with a weight of between 20 and 30 kg are anaesthetized with pentobarbital (30 mg/kg iv, Narcoren®, Merial, Germany) for the surgical interventions and the haemodynamic and functional investigation termini. Alcuronium chloride (3 mg/animal iv, Alloferin®, ICN Pharmaceuticals, Germany) serves additionally as a muscle relaxant. The dogs are intubated and ventilated with an oxygen/ambient air mixture (40/60%, about 5-6 L/min) Ventilation takes place using a ventilator from Draeger (Sulla 808) and is monitored using a carbon dioxide analyser (Engström). The anaesthesia is maintained by continual infusion of pentobarbital (50 µg/kg/min); fentanyl is used as an analgesic (10 µg/kg/h). One alternative to pentobarbital is to use isoflurane (1-2% by volume).

In preparatory interventions, the dogs are fitted with a cardiac pacemaker. At a time of 21 days before the first drug testing (i.e. start of experiment), a cardiac pacemaker from Biotronik (Logos®) is implanted into a subcutaneous skin pocket and is contacted with the heart via a pacemaker electrode which is advanced through the external jugular vein, with illumination, into the right ventricle.

At the same time as the implanting of the pacemaker, through retrograde advancing of 7F biopsy forceps (Cordis) via a sheath introducer (Avanti+®; Cordis) in the femoral artery, and after atraumatic passage through the aortic valve, there is defined lesion of the mitral valve, with monitoring by echocardiography and illumination. Thereafter all of the accesses are removed and the dog wakes spontaneously from the anaesthesia. After a further 7 days (i.e. 14 days before the first drug testing), the above-described pacemaker is activated and the heart is stimulated at a frequency of 220 beats per minute.

The actual drug testing experiments take place 14 and 28 days after the beginning of pacemaker stimulation, using the following instrumentation:

Introduction of a bladder catheter for bladder relief and for measuring the flow of urine;

Attachment of ECG leads to the extremities for ECG measurement;

Introduction of a Fluidmedic® PE-300 tube filled with sodium chloride solution into the femoral artery. This tube is connected to a pressure sensor (Braun Melsungen, Germany) for measuring the systemic blood pressure;

Introduction of a Millar Tip catheter (type 350 PC, Millar Instruments, Houston, USA) through the left atrium or through a port secured in the carotid artery, for measuring cardiac haemodynamics;

Introduction of a Swan-Ganz catheter (CCOmbo 7.5F, Edwards, Irvine, USA) via the jugular vein into the pulmonary artery, for measuring the cardiac output, oxygen saturation, pulmonary arterial pressures and central venous pressure;

Siting of a venous catheter in the cephalic vein, for infusing pentobarbital, for liquid replacement and for blood sampling (for determination of the plasma levels of substance or other clinical blood values);

Siting of a venous catheter in the saphenous vein, for infusing fentanyl and for administration of substance;

Infusion of vasopressin (Sigma) in increasing dosage, up to a dose of 4 mU/kg/min. The pharmacological substances are then tested with this dosage.

The primary signals are amplified if necessary (Gould amplifier, Gould Instrument Systems, Valley View, USA or Edwards-Vigilance-Monitor, Edwards, Irvine, USA) and subsequently fed into the Ponemah system (DataSciences Inc, Minneapolis, USA) for evaluation. The signals are recorded continuously throughout the experimental period, and are further processed digitally by said software, and averaged over 30 seconds.

C. EXEMPLARY EMBODIMENTS OF PHARMACEUTICAL COMPOSITIONS

The compounds according to the invention can be converted into pharmaceutical preparations in the following ways:

Tablet:
Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.
10 ml of oral suspension correspond to a single dose of 100 mg of the compound according to the invention.
Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400.20 g of oral solution correspond to a single dose of 100 mg of the compound according to the invention.
Production:
The compound according to the invention is suspended in the mixture of polyethylene glycol and polysorbate with stirring. The stirring process is continued until the compound according to the invention has completely dissolved.

i.v. Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of formula (I)

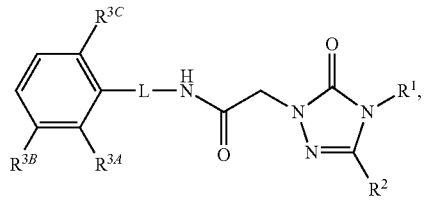

in which
R$^1$ represents (C$_1$-C$_4$)-alkyl or (C$_2$-C$_4$)-alkenyl, each of which may be mono- or disubstituted by identical or different radicals selected from the group consisting of fluorine, trifluoromethyl, hydroxy, methoxy and ethoxy, or
represents benzyl which may be substituted in the phenyl ring by a radical selected from the group consisting of fluorine, chlorine, methyl, trifluoromethyl and methoxy, or
represents cyclopropyl,
R$^2$ represents phenyl or thienyl which are substituted by a radical selected from the group consisting of fluorine and chlorine,
R$^{3A}$ and R$^{3B}$ independently of one another represent hydrogen, fluorine, chlorine, methyl, trifluoromethyl, methoxy or trifluoromethoxy,
but where at least one of the radicals R$^{3A}$ and R$^{3B}$ is different from hydrogen,
R$^{3C}$ represents hydrogen, and
L represents a group of the formula

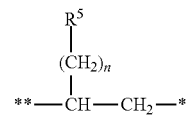

in which
* represents the point of attachment to the adjacent nitrogen atom and
** represents the point of attachment to the phenyl ring,
n represents the number 0 or 1, and
R$^5$ represents a group of the formula —O—C(=O)—NHR$^{7B}$, —NH—C(=O)—NHR$^{7B}$, —NH—C(=O)—R$^9$, —NH—SO$_2$—R$^{10}$ or —NH—C(=O)—OR$^{10}$ in which
R$^{7B}$ represents hydrogen or (C$_1$-C$_4$)-alkyl,
R$^9$ represents hydrogen or (C$_1$-C$_4$)-alkyl, and
R$^{10}$ represents (C$_1$-C$_4$)-alkyl,
or a salt thereof.

2. A pharmaceutical composition comprising a compound of claim 1 and one or more inert non-toxic pharmaceutically suitable auxiliaries.

3. A pharmaceutical composition comprising a compound of claim 1 and at least one active substance selected from the group consisting of a diuretic, an angiotensin AII antagonist, an ACE inhibitor, a beta-receptor blocker, a mineralocorticoid receptor antagonist, an organic nitrate, an NO donor and a positive-inotropic active substance.

* * * * *